United States Patent
Bender et al.

(10) Patent No.: US 7,456,166 B2
(45) Date of Patent: *Nov. 25, 2008

(54) CYCLOPROPYL FUSED INDOLOBENZAZEPINE HCV NS5B INHIBITORS

(75) Inventors: John A. Bender, Middletown, CT (US); Min Ding, Glastonbury, CT (US); Robert G. Gentles, Wallingford, CT (US); Piyasena Hewawasam, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/743,921

(22) Filed: May 3, 2007

(65) Prior Publication Data

US 2007/0270405 A1 Nov. 22, 2007

Related U.S. Application Data

(60) Provisional application No. 60/894,757, filed on Mar. 14, 2007, provisional application No. 60/852,084, filed on Oct. 16, 2006, provisional application No. 60/802,005, filed on May 19, 2006, provisional application No. 60/801,125, filed on May 17, 2006.

(51) Int. Cl.
*A61K 31/55* (2006.01)
*A61P 31/00* (2006.01)

(52) U.S. Cl. .............................. 514/214.01; 540/576
(58) Field of Classification Search ............ 514/214.01; 540/576

See application file for complete search history.

(56) References Cited

U.S. PATENT DOCUMENTS

| 7,153,848 B2 | 12/2006 | Hudyma et al. ......... 514/214.01 |
| 2006/0166964 A1 | 7/2006 | Hudyma et al. ......... 514/211.09 |
| 2007/0060565 A1 | 3/2007 | Meanwell et al. ....... 514/214.01 |
| 2007/0078122 A1 | 4/2007 | Bergstrom et al. ...... 514/214.01 |
| 2007/0185083 A1 | 8/2007 | Bergstrom, et al. .... 514/214.01 |

FOREIGN PATENT DOCUMENTS

| WO | WO2005/080399 | 9/2005 |
| WO | WO2006040039 | 4/2006 |
| WO | WO2006/046030 | 5/2006 |
| WO | WO2007029029 | 3/2007 |

OTHER PUBLICATIONS

U.S. Appl. No. 11/752,354, filed May 23, 2007, Robert G. Gentles, et al.
U.S. Appl. No. 11/753,137, filed May 24, 2007, Carl P. Bergstrom.
U.S. Appl. No. 11/756,203, filed May 31, 2007, Kap-Sun Yeung, et al.

*Primary Examiner*—Brenda L Coleman
(74) *Attorney, Agent, or Firm*—James Epperson

(57) ABSTRACT

The invention encompasses compounds of formula I as well as compositions and methods of using the compounds. The compounds have activity against hepatitis C virus (HCV) and are useful in treating those infected with HCV.

17 Claims, No Drawings

CYCLOPROPYL FUSED INDOLOBENZAZEPINE HCV NS5B INHIBITORS

CROSS REFERENCE TO RELATED APPLICATIONS

This application claims the benefit of U.S. Provisional Application Ser. No. 60/801,125, filed May 17, 2006; Ser. No. 60/802,005, filed May 19, 2006; Ser. No. 60/852,084, filed Oct. 16, 2006; and Ser. No. 60/894,757, filed Mar. 14, 2007.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. N. Engl. J. Med. 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., Journal of Virology 2002, 3482-3492; and Defrancesco and Rice, Clinics in Liver Disease 2003, 7, 211-242.

Currently, the most effective HCV therapy employs a combination of alpha-interferon and ribavirin, leading to sustained efficacy in 40% of patients (Poynard, T. et al. Lancet 1998, 352, 1426-1432). Recent clinical results demonstrate that pegylated alpha-interferon is superior to unmodified alpha-interferon as monotherapy (Zeuzem, S. et al. N. Engl J. Med. 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

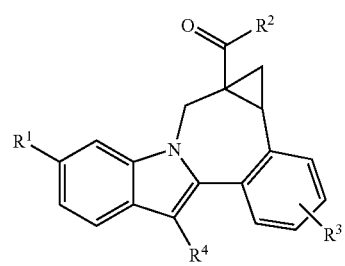

where:
$R^1$ is $CO_2R^5$ or $CONR^6R^7$;
$R^2$ is

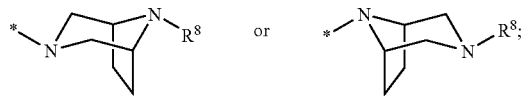

$R^3$ is hydrogen, halo, alkyl, alkenyl, hydroxy, benzyloxy, alkoxy, or haloalkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, $(R^9)_2NSO_2$, or $(R^{10})SO_2$;
$R^7$ is hydrogen or alkyl;
$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;
$R^9$ is hydrogen, alkyl, or cycloalkyl; and
$R^{10}$ is azetidinyl, pyrrolidinyl, piperidinyl, piperazinyl, morpholinyl, thiomorpholinyl, homopiperidinyl, or homomorpholinyl and is substituted with 0-3 alkyl substituents;

or a pharmaceutically acceptable salt thereof.
Another aspect of the invention is a compound of formula I where
$R^1$ is $CO_2R^5$ or $CONR^6R^7$;
$R^2$ is a

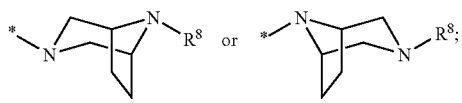

$R^3$ is hydrogen, halo, alkyl, alkenyl, hydroxy, benzyloxy, or alkoxy;
$R^4$ is cycloalkyl;

$R^5$ is hydrogen or alkyl;
$R^6$ is hydrogen, alkyl, alkylSO$_2$, cycloalkylSO$_2$, haloalkylSO$_2$, $(R^9)_2$NSOO$_2$, or $(R^{10})$SO$_2$;
$R^7$ is hydrogen or alkyl;
$R^8$ is hydrogen, alkyl, cycloalkyl, (cycloalkyl)alkyl, alkylcarbonyl, alkoxycarbonyl, benzyl, benzyloxycarbonyl, or pyridinyl;
$R^9$ is hydrogen or alkyl; and
$R^{10}$ is azetidinyl, pyrrolidinyl, piperidinyl, piperazinyl, N-(alkyl)piperazinyl, morpholinyl, thiomorpholinyl, homopiperidinyl, or homomorpholinyl;

or a pharmaceutically acceptable salt thereof.

Another aspect of the invention is a compound of formula I where $R^1$ is CONR$^6$R$^7$;
$R^6$ is alkylSO$_2$, cycloalkylSO$_2$, haloalkylSO$_2$, $(R^9)_2$NSO$_2$, or $(R^{10})$SO$_2$; and $R^7$ is hydrogen.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $(R^9)_2$NSO$_2$ or $(R^{10})$SO$_2$.

Another aspect of the invention is a compound of formula I where $R^6$ is (dimethylamino)SO$_2$.

Another aspect of the invention is a compound of formula I where $R^6$ is alkylSO$_2$.

Another aspect of the invention is a compound of formula I where $R^6$ is isopropylSO$_2$.

Another aspect of the invention is a compound of formula I according to the following stereochemistry.

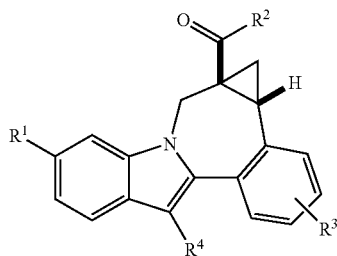

Another aspect of the invention is a compound of formula I according to the following stereochemistry.

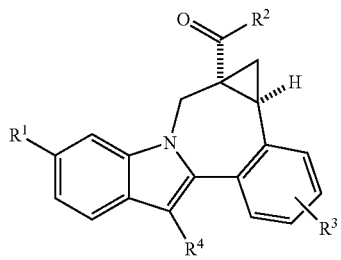

Any scope of any variable, including $R^1$, $R^2$, $R^3$, $R^4$, $R^5$, $R^6$, $R^7$, $R^8$, $R^9$, or $R^{10}$, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

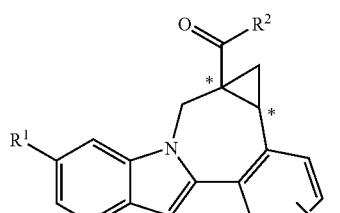

Synthetic Methods

The compounds may be made by methods known in the art including those described below. Some reagents and intermediates are known in the art. Other reagents and intermediates can be made by methods known in the art using readily available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Methyl 2-bromo-3-cyclohexyl-1H-indole-6-carboxylate can be hydrolyzed to 2-bromo-3-cyclohexyl-1H-indole-6-carboxylic acid (See Scheme 1). This compound can be condensed with a variety of sulfonyl ureas, using for example, 1,1'-carbonyldiimidazole in combination with 1,8-diazabicyclo[5.4.0]undec-7-ene in anhydrous THF. The resultant acyl sulfamides can be subjected to known coupling reactions with a diversity of 2-formyl boronic acids or esters, using for example, Suzuki coupling conditions, to provide cyclic hemiaminal intermediates of the type depicted. These compounds can be converted to indolobenzazepines derivatives by treatment with methyl 2-(dimethoxyphosphoryl)acrylate under the influence of cesium carbonate in DMF via consecutive Michael and Horner Emmons reactions.

Related fused cyclopropyl ester derivatives can be generated by methods known in the art, including treatment of the indolobenzazepine esters with trimethyl sulfoxonium iodide under strongly basic conditions in DMSO. The residual aliphatic ester moiety in the resultant fused cyclopropanes can be hydrolyzed and the product acids can be condensed with a variety of alkyl-bridged piperazines. For example, O-(1H-benzotriazol-1-yl)-N,N,N',N'-tetramethyluronium tetrafluoroborate and diisopropyl ethyl amine in DMSO can give alkyl bridged piperazine carboxamides.

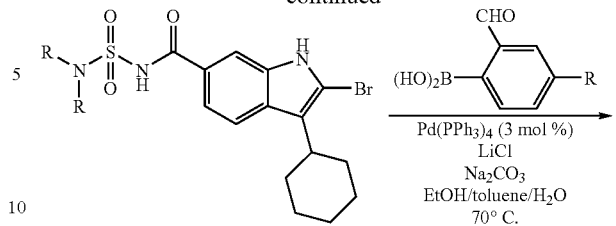

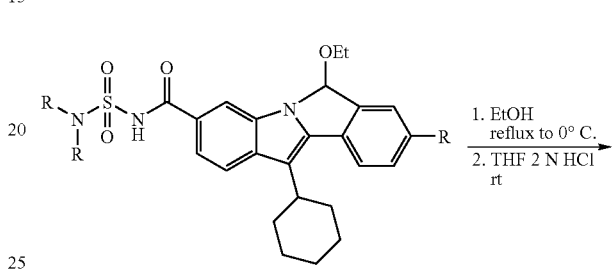

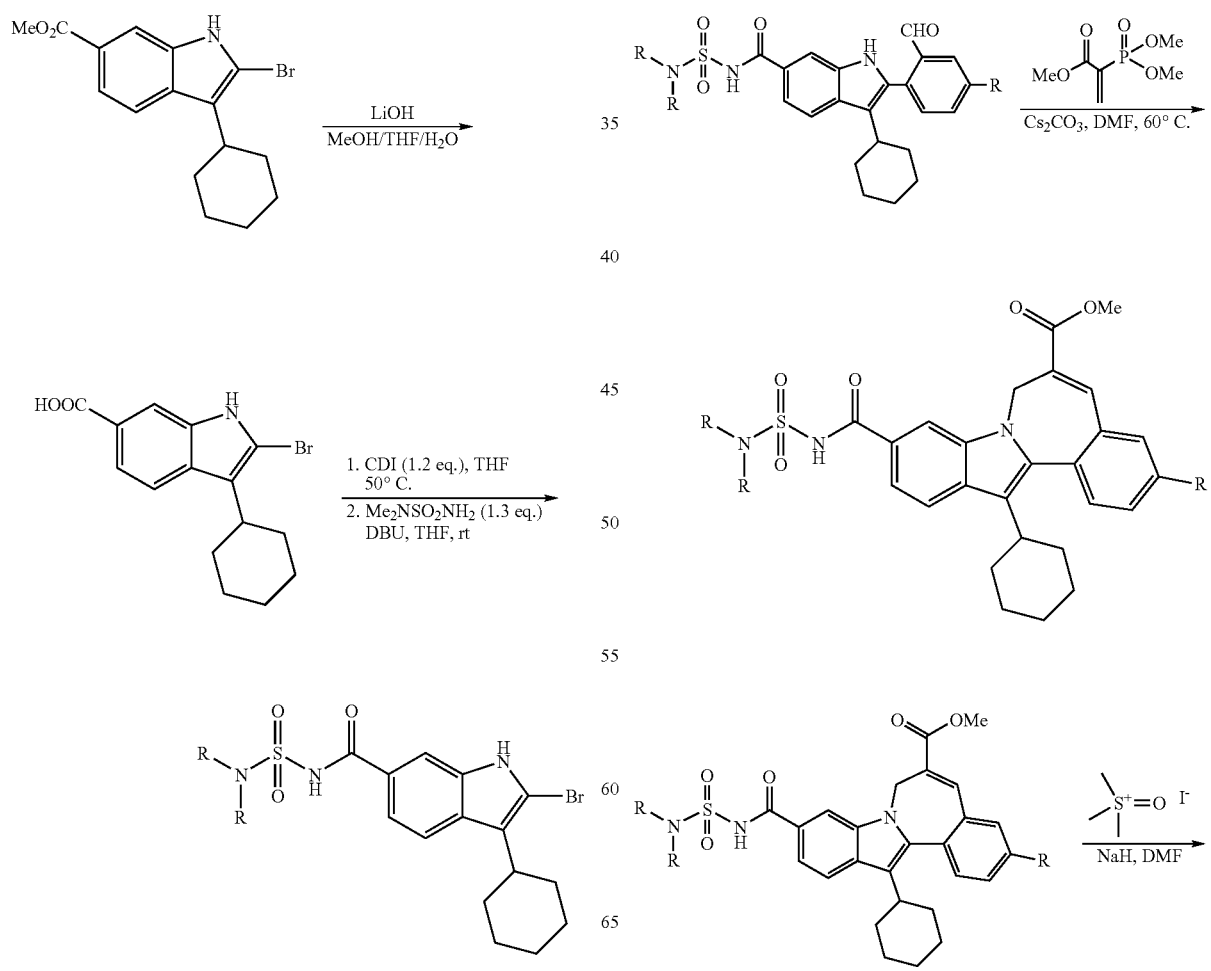

Scheme 1.

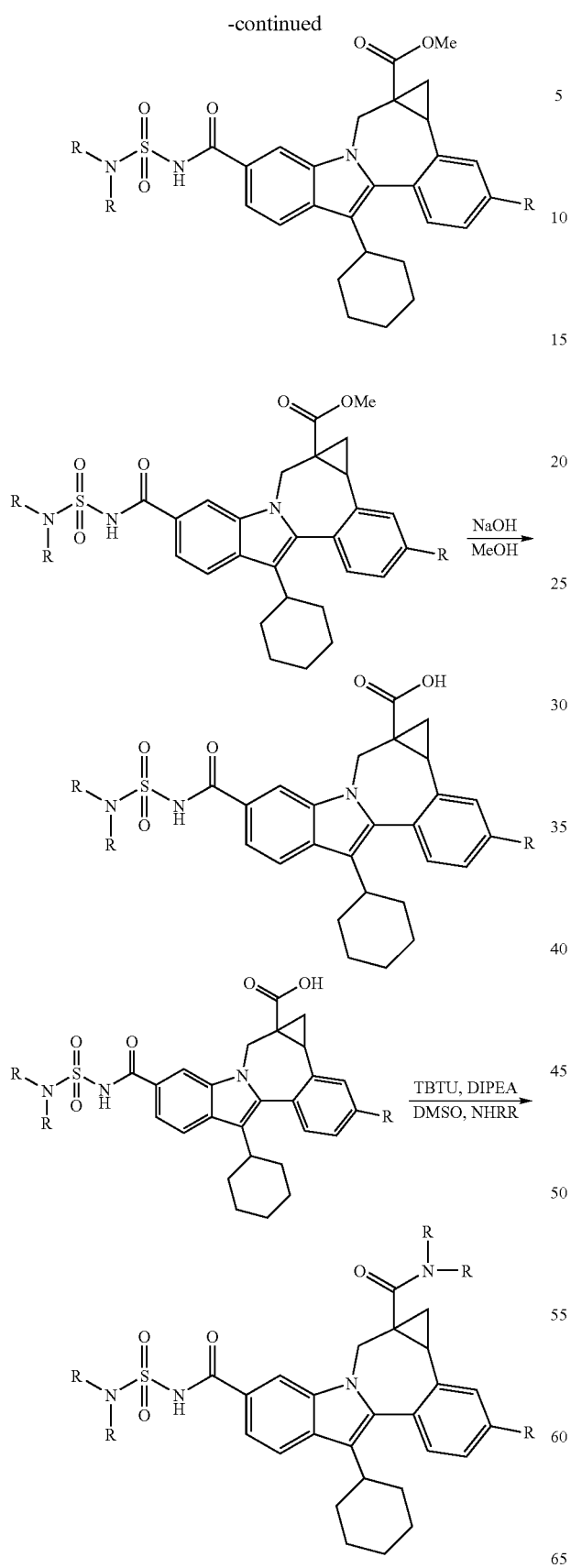
N-protected piperazines can also be coupled to the intermediate indolobenzazepine acids and the resultant piperazine carboxamides can be deprotected using methods known in the art and derivatized using a variety of synthetic protocols, some illustrative examples of which are shown below (See Scheme 2).
Scheme 2.
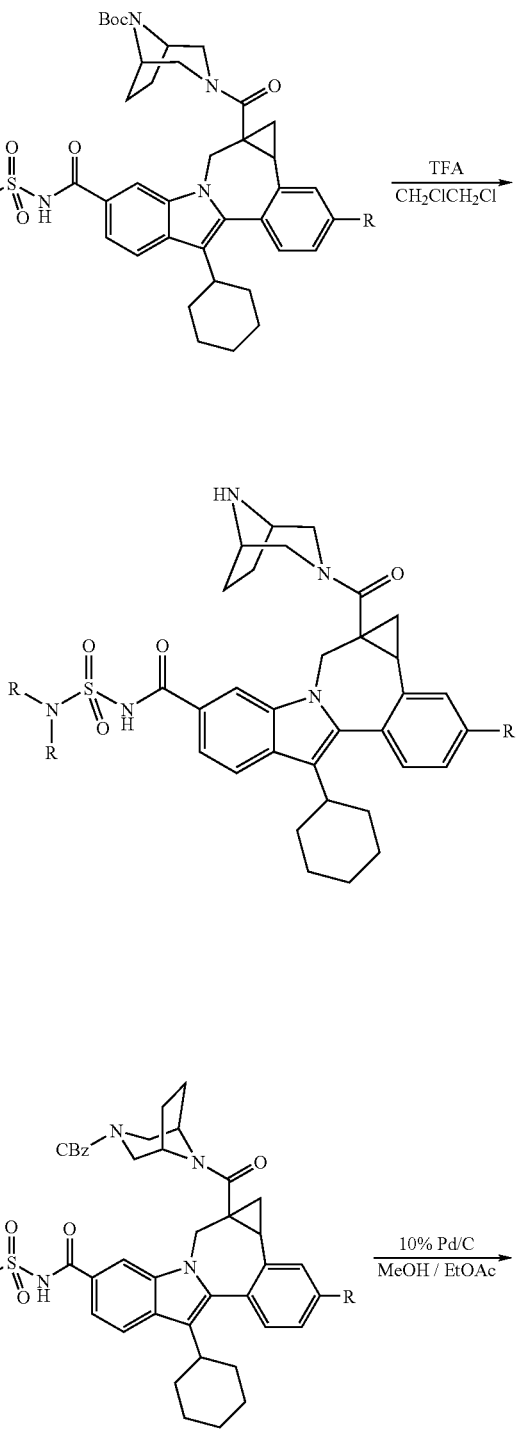

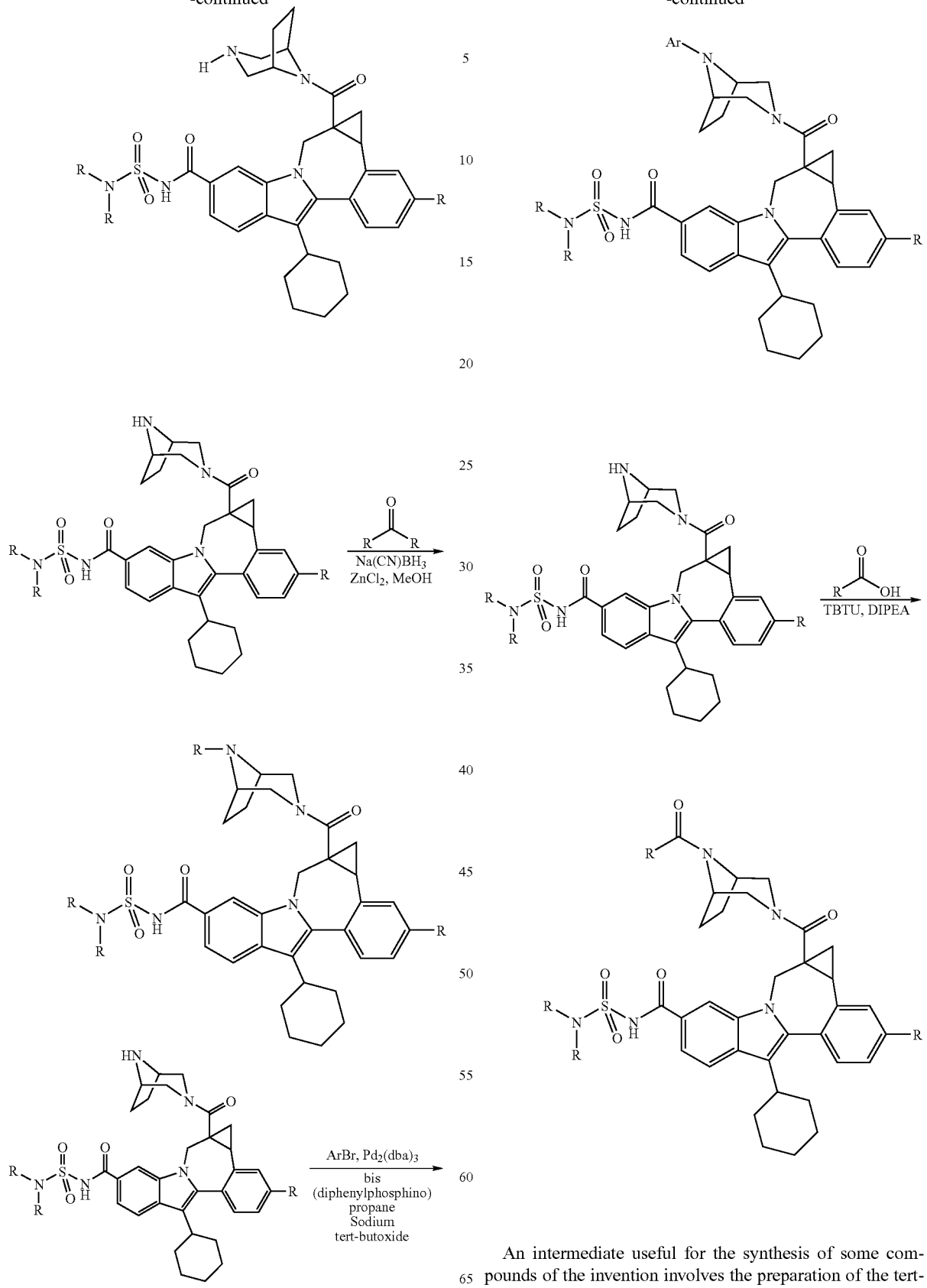
An intermediate useful for the synthesis of some compounds of the invention involves the preparation of the tert-butyl ester indolobenzazepine shown in Scheme 3.

Scheme 3.

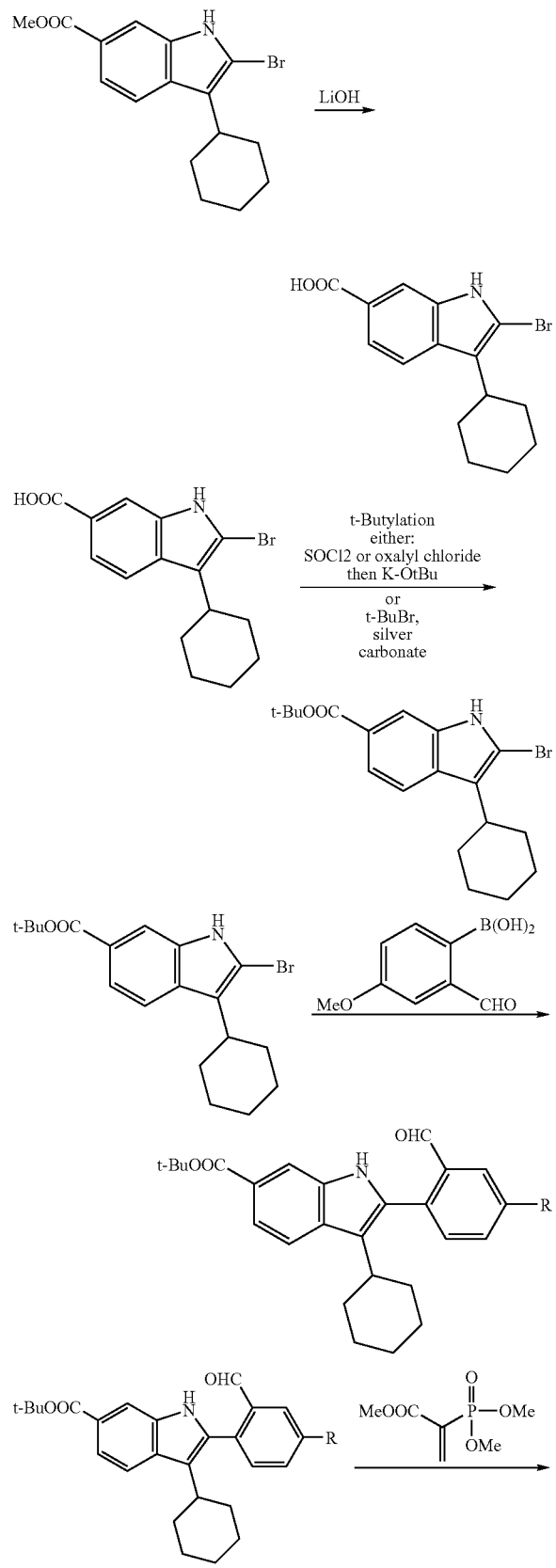

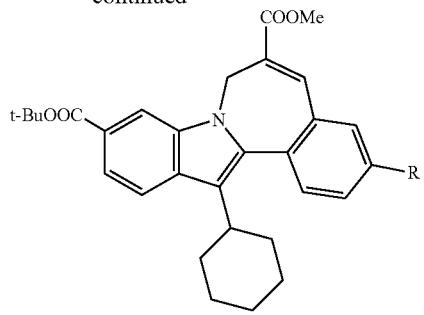

This methodology involves base catalyzed hydrolysis of the indole methyl ester shown, followed by its reaction with either thionyl chloride and potassium tertiary butoxide, or alkylation with silver carbonate and tertiary butyl bromides. The resultant compound can be transformed using chemistry analogous to that outlined previously to provide the mixed ester indolobenzazepines shown above.

These intermediates are useful in an alternative procedure that can be employed for the preparation of acylsulfamide and acylsulfonamide alkyl-bridged piperazines, as shown in Scheme 4. Cyclopropanation of an intermediate t-butyl ester indolobenzazepine and subsequent cleavage of the t-butyl ester group can generate the acid which can be coupled to a diversity of sulfonamides and sulfonylureas. Subsequent hydrolysis affords the related aliphatic acid, which can be coupled with a diversity of alkyl-bridged piperazines. For example, O-(1H-benzotriazol-1-yl)-N,N,N',N'-tetramethyluronium tetrafluoroborate and diisopropyl ethyl amine in DMSO can give the alkyl bridged piperazine carboxamides.

Scheme 4.

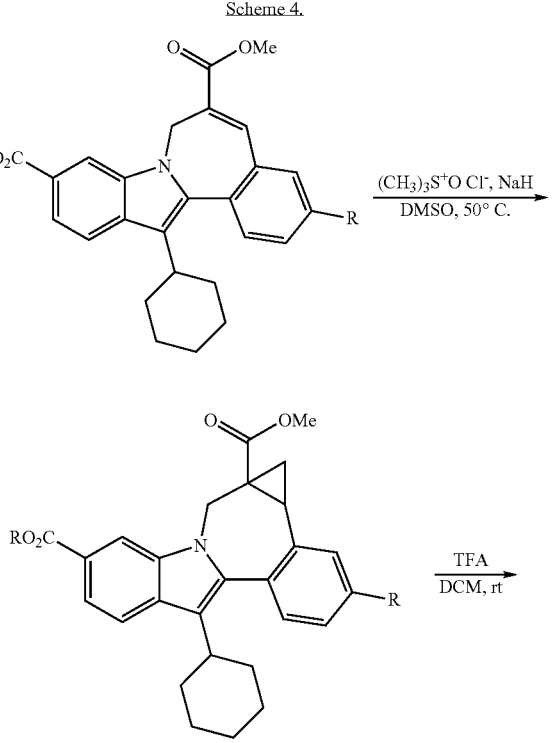

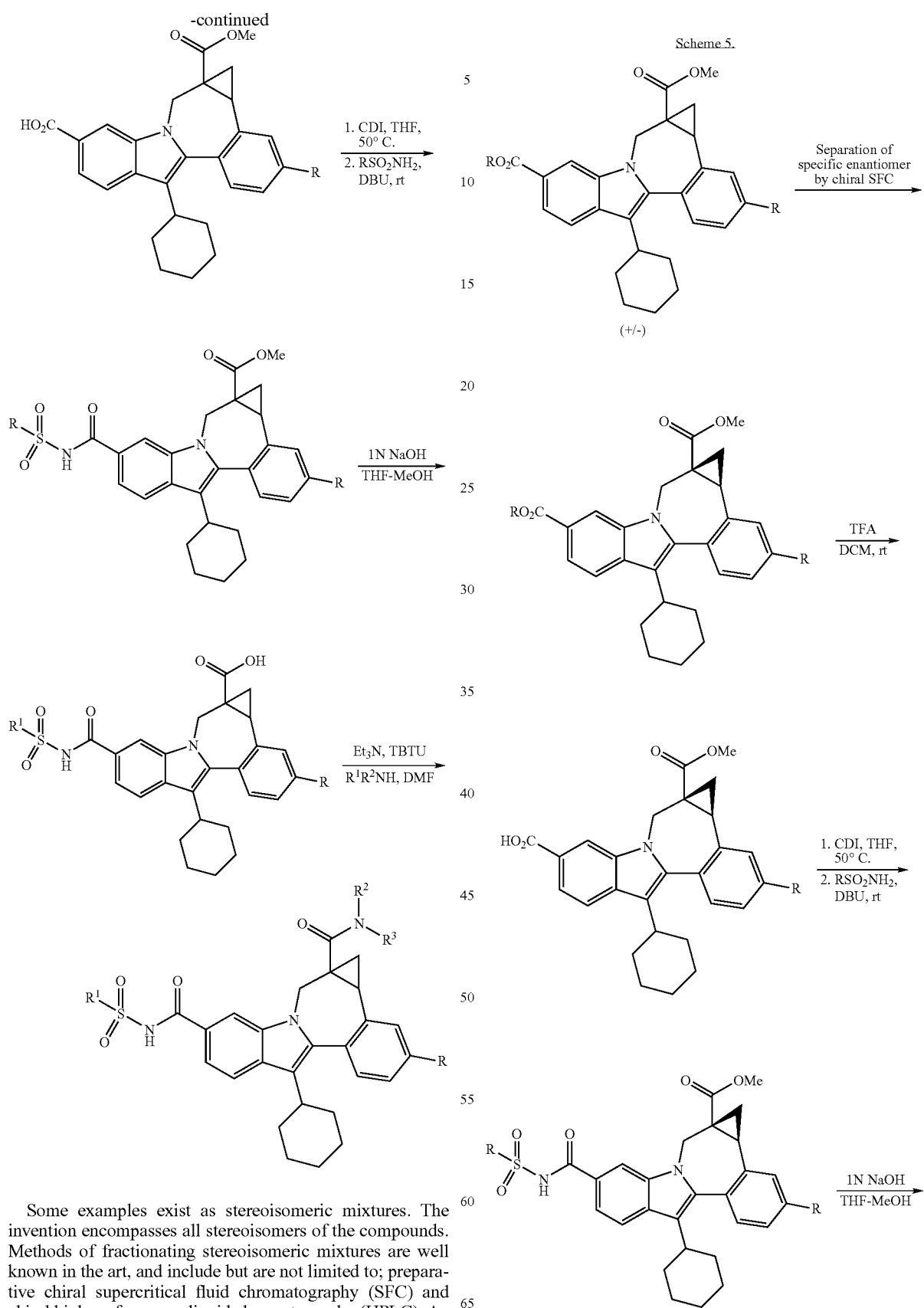

Some examples exist as stereoisomeric mixtures. The invention encompasses all stereoisomers of the compounds. Methods of fractionating stereoisomeric mixtures are well known in the art, and include but are not limited to; preparative chiral supercritical fluid chromatography (SFC) and chiral high performance liquid chromatography (HPLC). An example using this approach is shown in scheme 5.

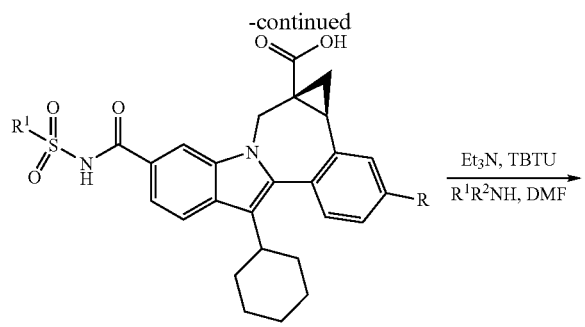

An additional method to achieve such separations involves the preparation of mixtures of diastereomers which can be separated using a variety of methods known in the art. One example of this approach is shown below (Scheme 6).

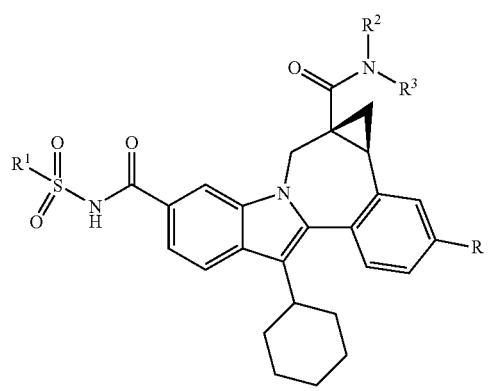

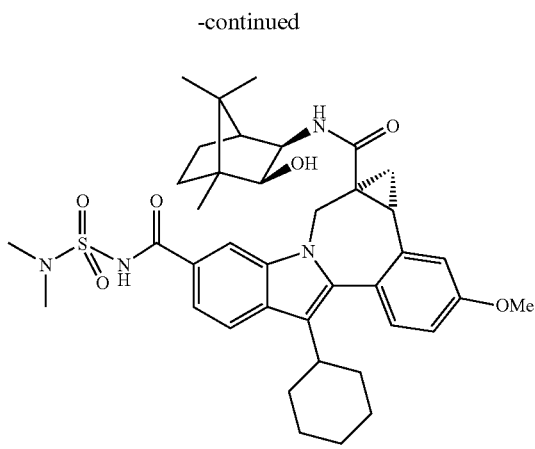

Diastereomers separated by reverse phase HPLC

Some diastereomeric amides can be separated using reverse phase HPLC. After hydroysis, the resultant optically active acids can be coupled with bridged piperazine derivatives (Scheme 6). For example, O-(1H-benzotriazol-1-yl)-N,N,N',N'-tetramethyluronium tetrafluoroborate and diisopropyl ethyl amine in DMSO can be used to give the alkyl bridged piperazine carboxamides. Other standard acid amine coupling methods can also be used to give optically active carboxamides.

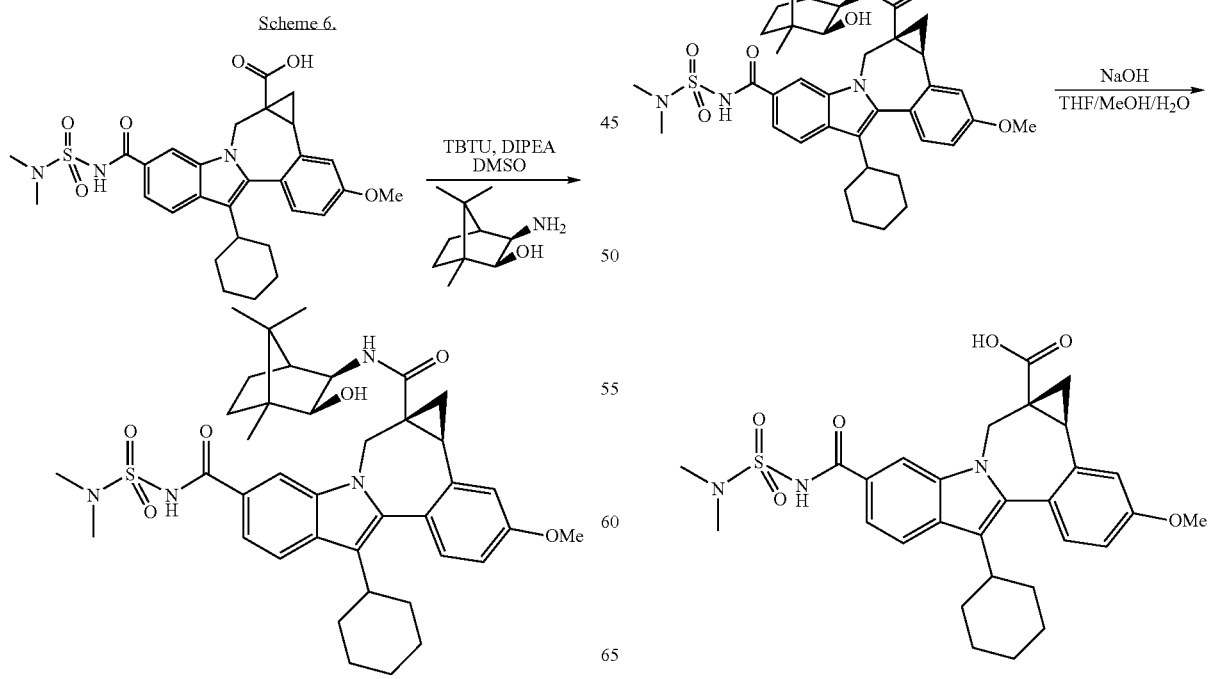

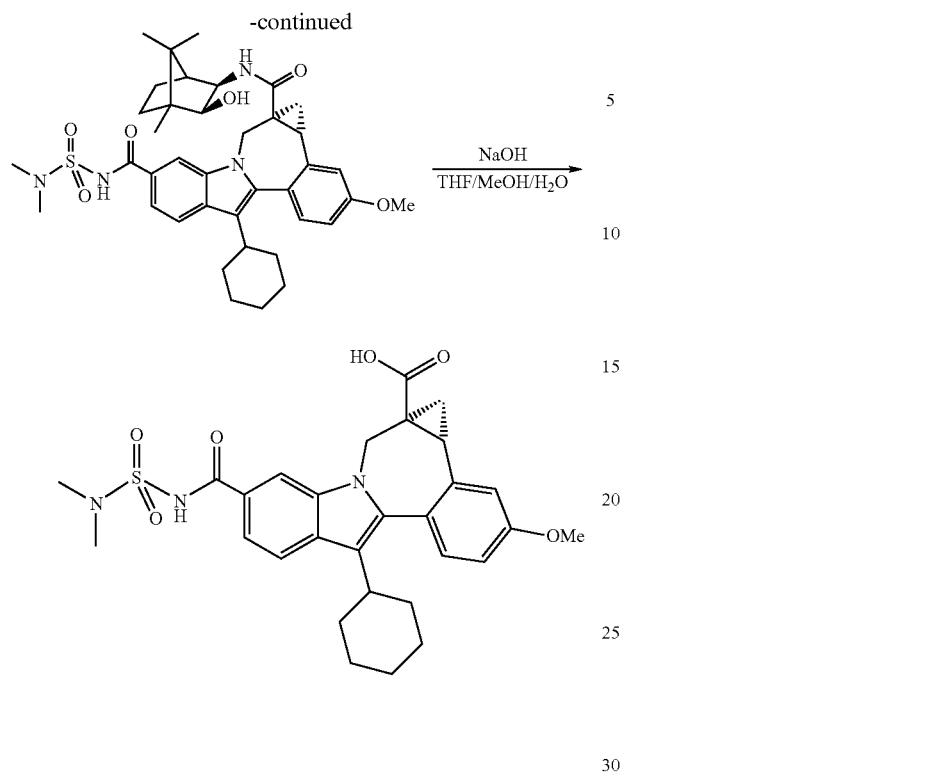
Schemes 7-9 illustrate other methods of making intermediates and compounds.
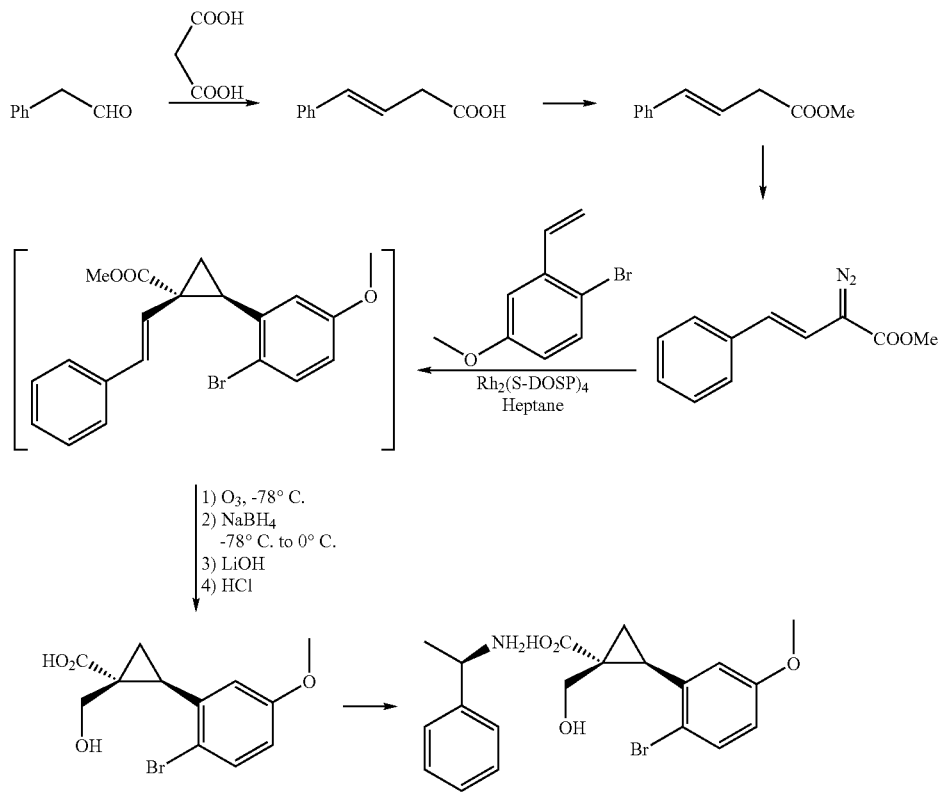

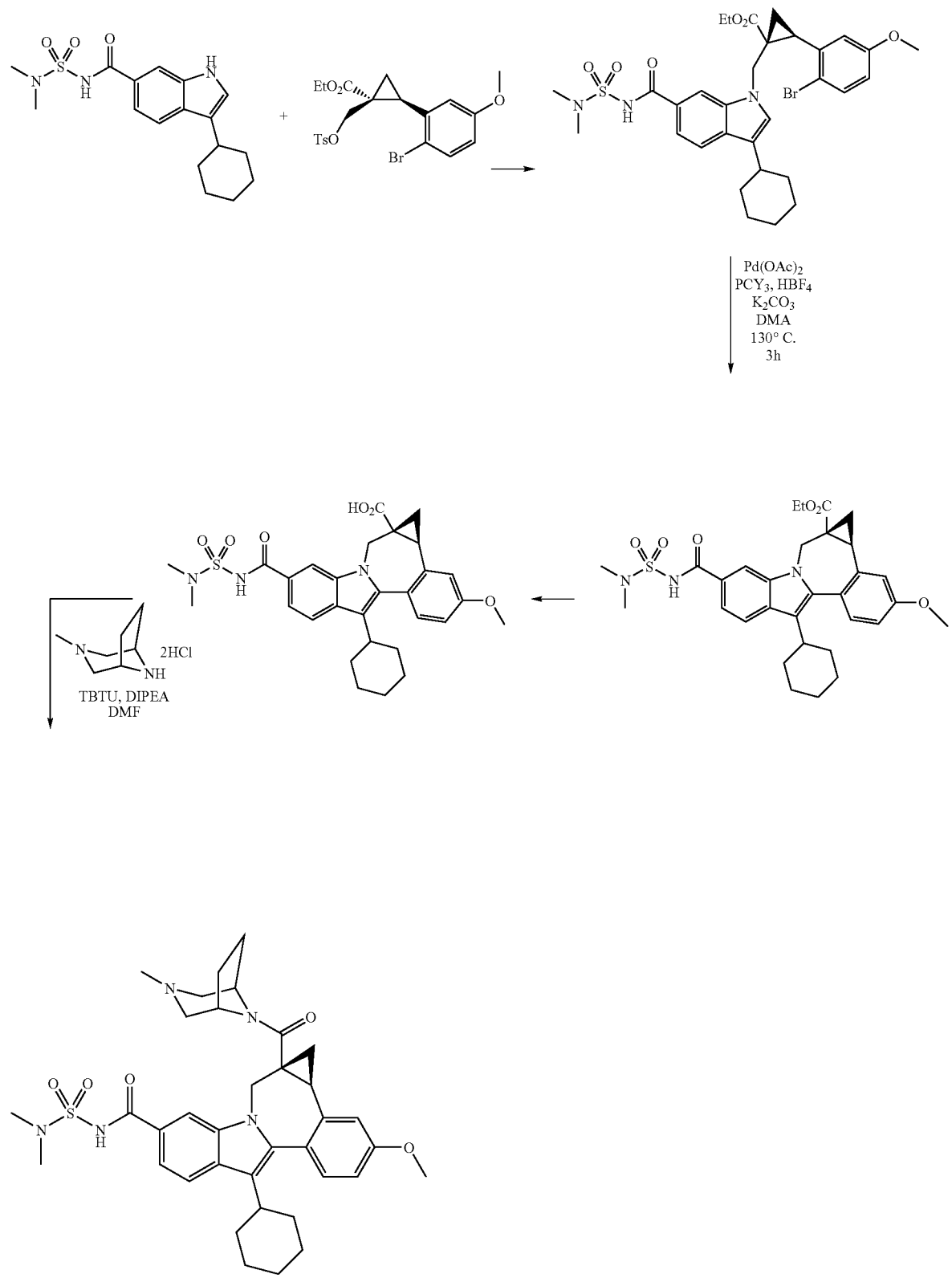

Scheme 9.

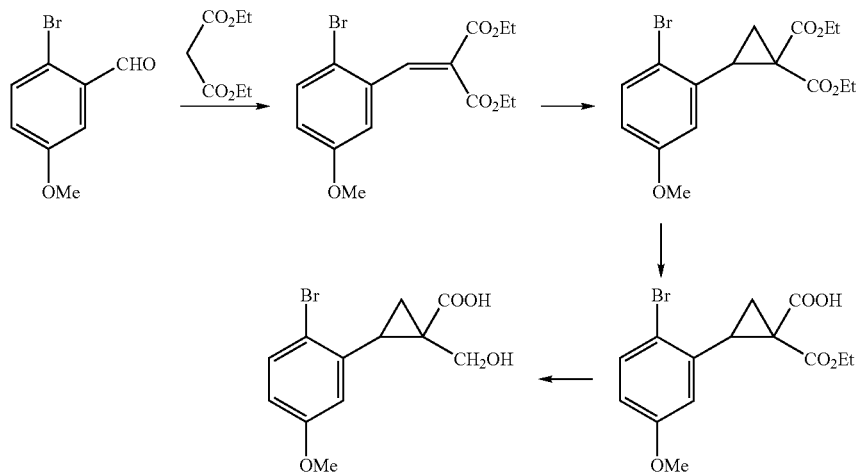

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT 12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)\char`\^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH$_2$O, NaCl added to 150 mM final, the FRET peptide diluted to 20 μM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a CO$_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naive Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. EC$_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Structure | IC$_{50}$ | EC$_{50}$ |
|---|---|---|
| 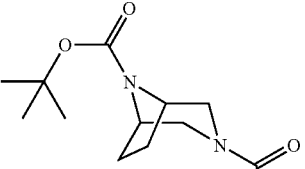 | C | B |
| 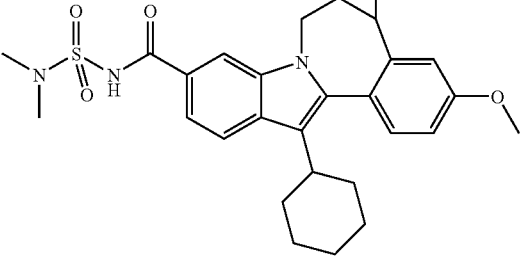 | B | B |

TABLE 1-continued
| Structure | IC$_{50}$ | EC$_{50}$ |
|---|---|---|
| 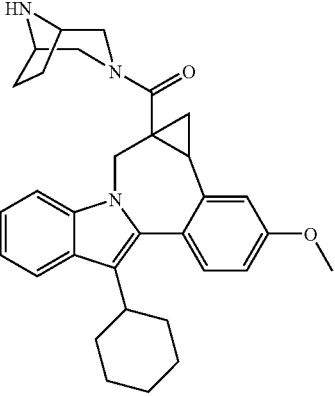 | B | B |
| 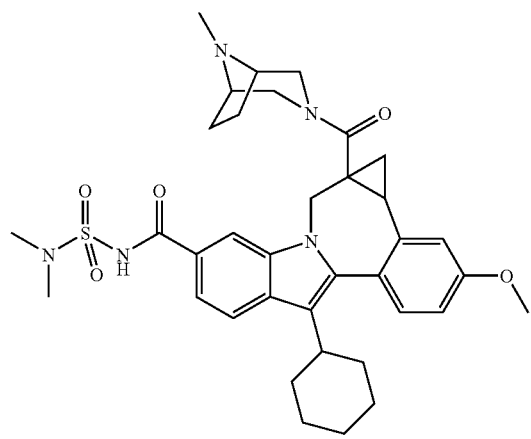 | B | B |
| 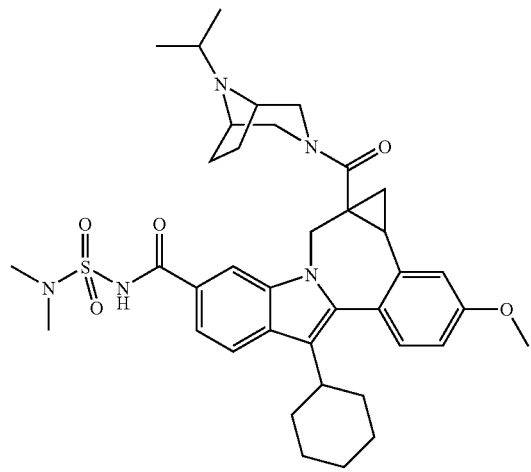 | C | B |

TABLE 1-continued

| Structure | IC$_{50}$ | EC$_{50}$ |
|---|---|---|
| | B | B |
| | B | B |
| | B | B |

TABLE 1-continued
| Structure | IC$_{50}$ | EC$_{50}$ |
|---|---|---|
| 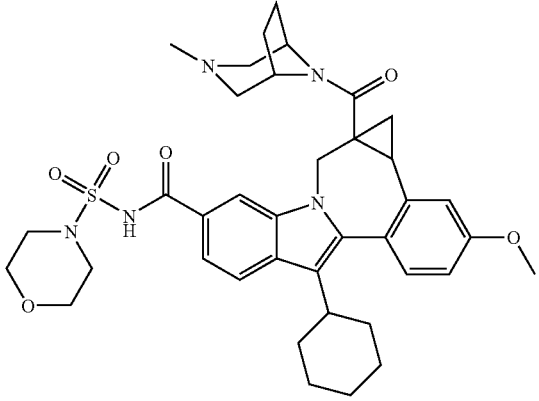 | B | B |
| 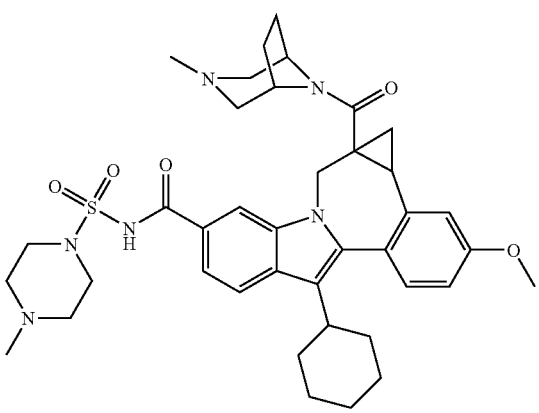 | B | B |
| 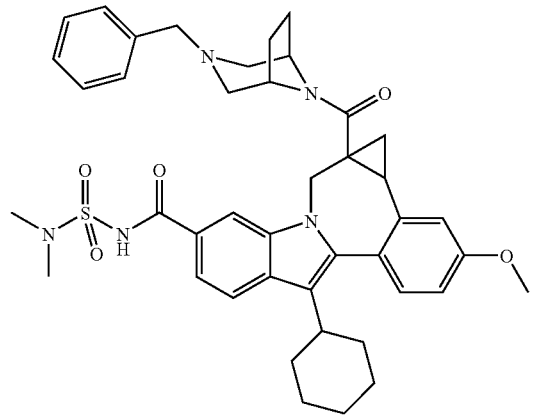 | B | B |

TABLE 1-continued
| Structure | IC$_{50}$ | EC$_{50}$ |
| --- | --- | --- |
| 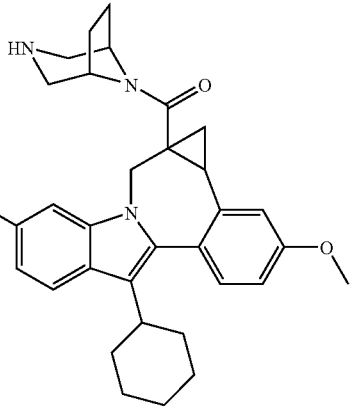 | B | B |
| 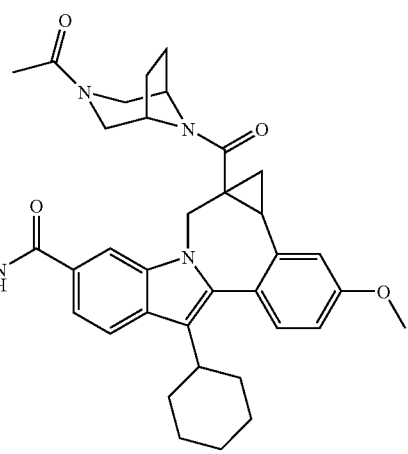 | B | B |
| 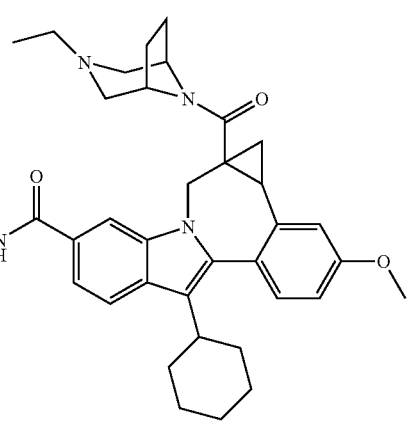 | B | B |

TABLE 1-continued
| Structure | IC$_{50}$ | EC$_{50}$ |
| --- | --- | --- |
| 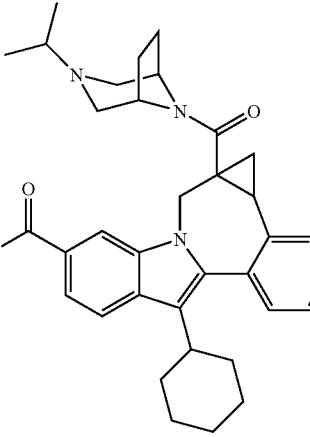 | B | B |
| 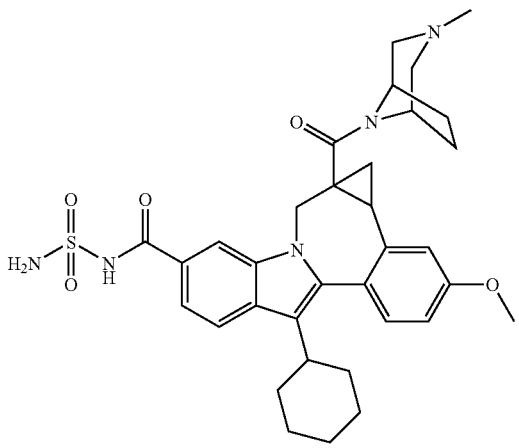 | B | B |
| 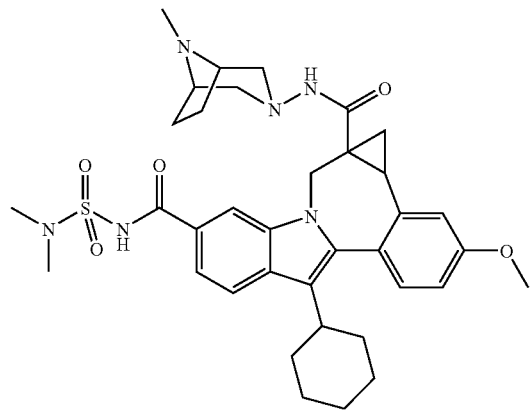 | B | B |

TABLE 1-continued
| Structure | IC$_{50}$ | EC$_{50}$ |
| --- | --- | --- |
| 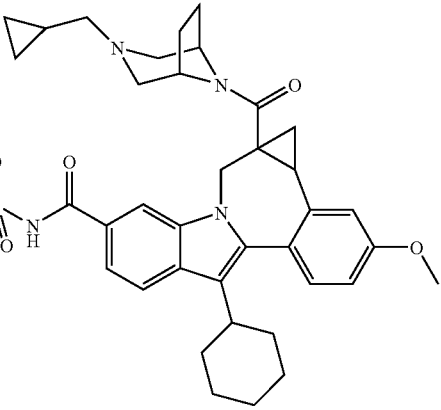 | B | B |
| 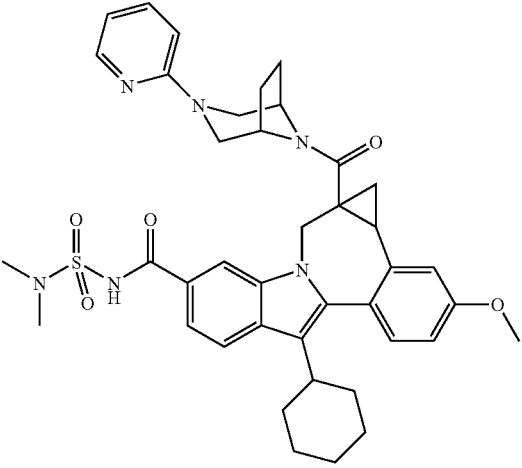 | B | B |
| 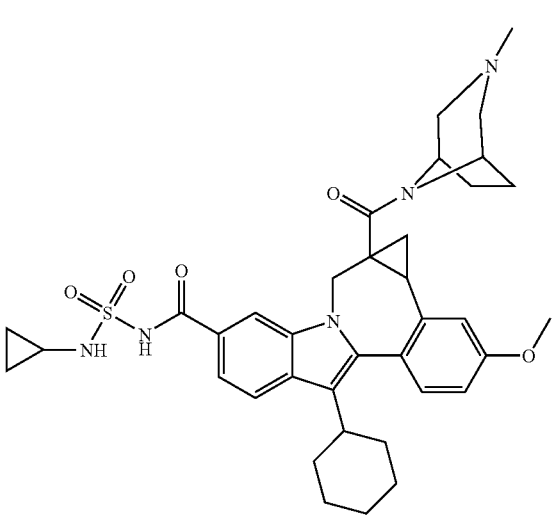 | B | B |

TABLE 1-continued
| Structure | IC$_{50}$ | EC$_{50}$ |
|---|---|---|
| 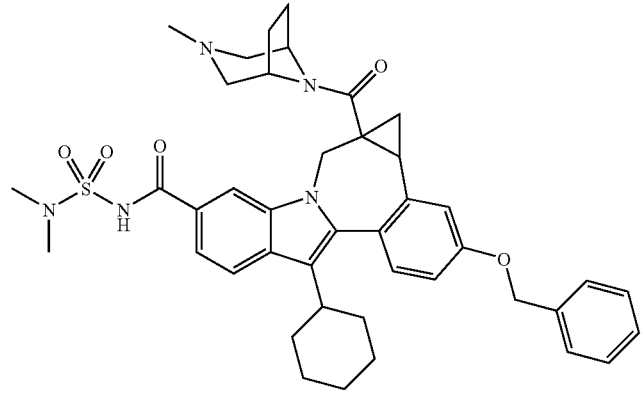 | B | B |
| 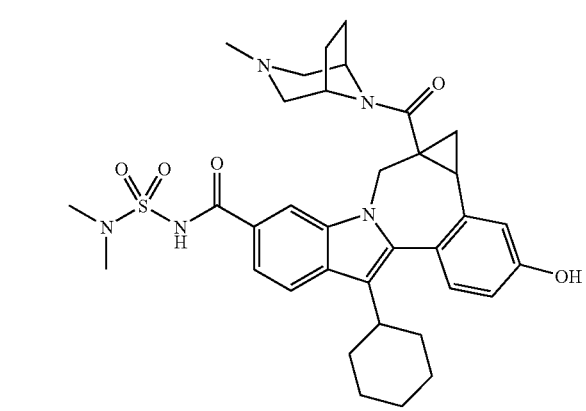 | B | B |
| 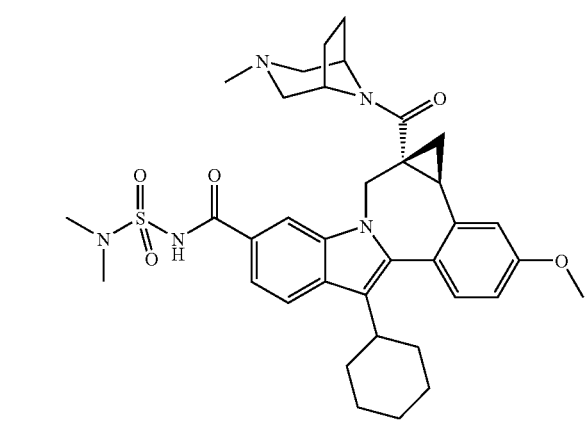 | B | B |

TABLE 1-continued

| Structure | IC$_{50}$ | EC$_{50}$ |
|---|---|---|
| | B | B |
| | B | B |
| | B | B |

TABLE 1-continued
| Structure | IC$_{50}$ | EC$_{50}$ |
|---|---|---|
| 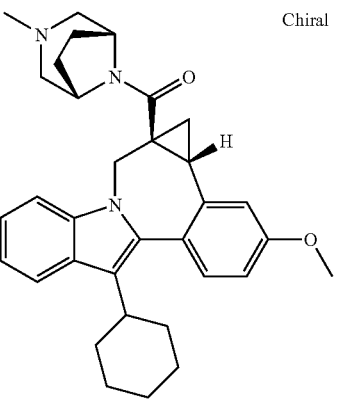 Chiral | B | B |
| 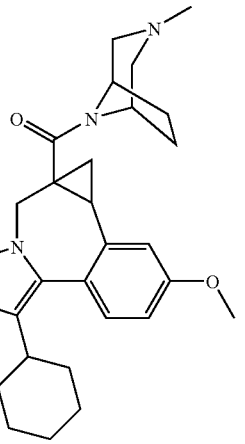 | B | B |
| 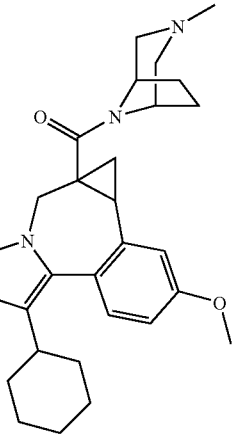 | B | B |

TABLE 1-continued

| Structure | IC$_{50}$ | EC$_{50}$ |
|---|---|---|
| | B | B |
| | B | B |
| | B | B |

TABLE 1-continued
| Structure | | IC$_{50}$ | EC$_{50}$ |
|---|---|---|---|
| 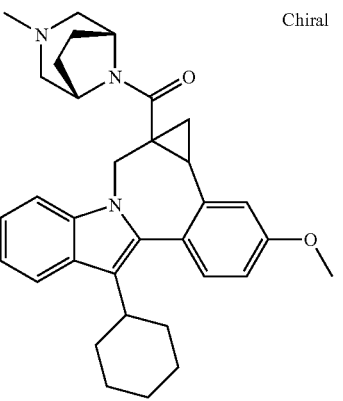 | Chiral | B | B |
| 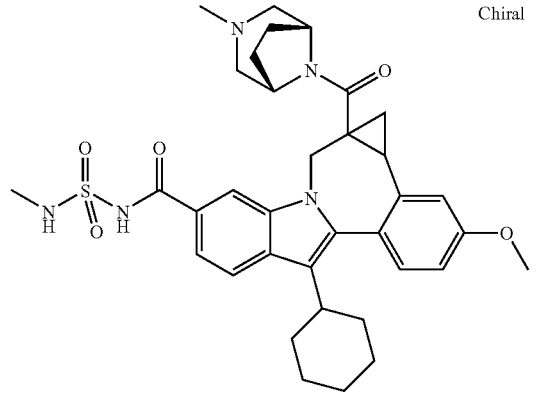 | Chiral | B | B |
| 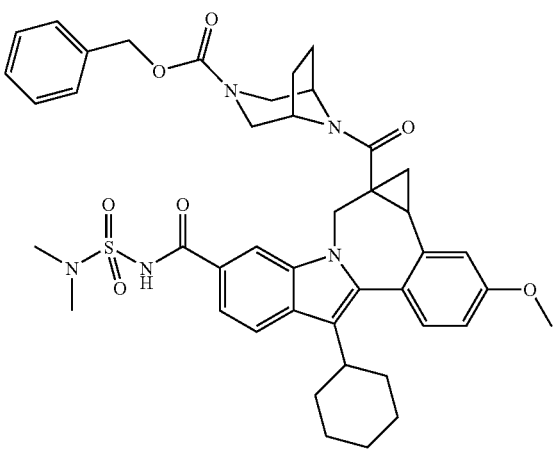 | | B | B |

TABLE 1-continued
| Structure | IC$_{50}$ | EC$_{50}$ |
|---|---|---|
| 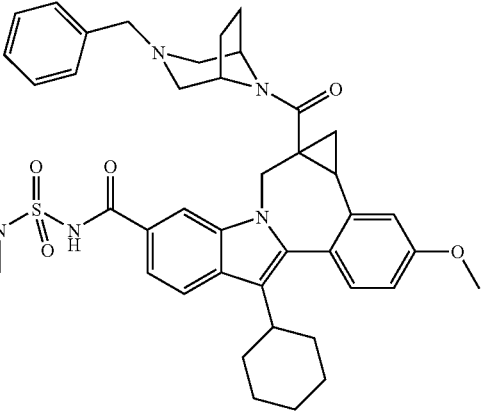 | B | B |
| 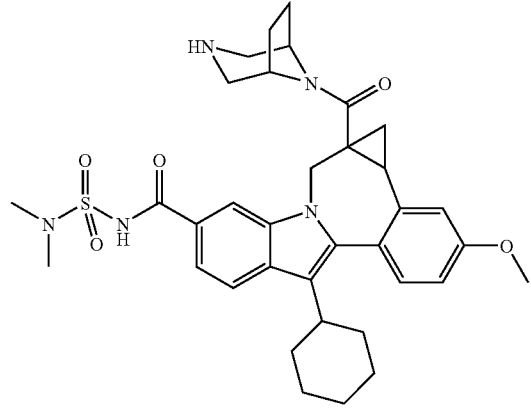 | B | B |
| 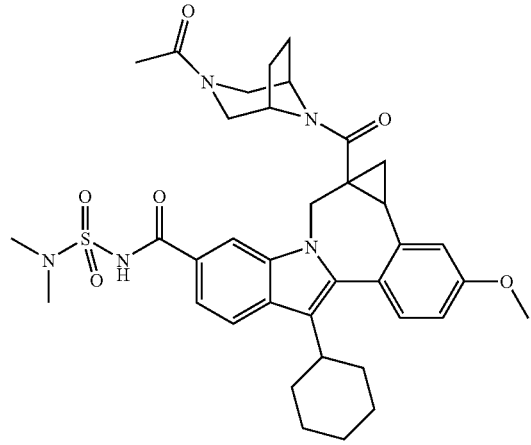 | B | B |

TABLE 1-continued

| Structure | IC$_{50}$ | EC$_{50}$ |
|---|---|---|
| | B | B |
| | B | B |
| | B | B |

TABLE 1-continued

| Structure | IC$_{50}$ | EC$_{50}$ |
|---|---|---|
| | B | B |
| | B | B |
| | B | B |

TABLE 1-continued
| Structure | IC$_{50}$ | EC$_{50}$ |
| --- | --- | --- |
| 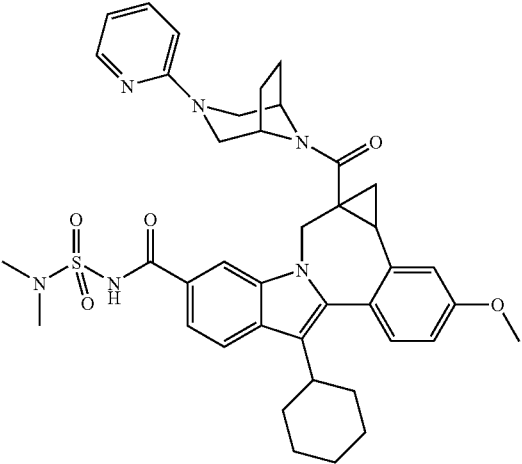 | B | B |
| 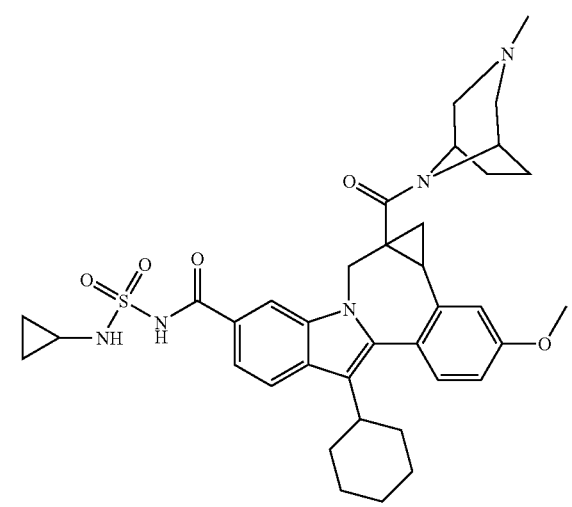 | B | B |
| 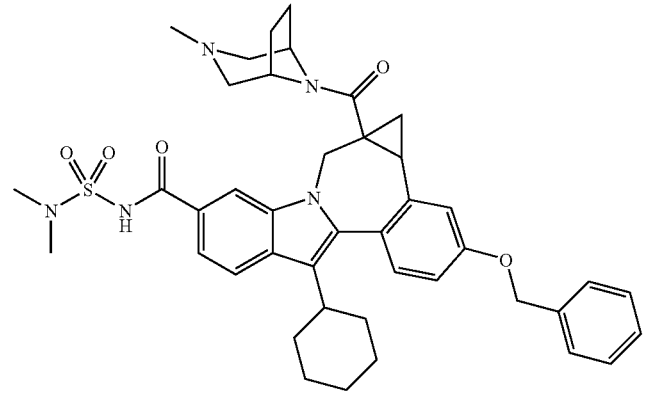 | B | B |

TABLE 1-continued
| Structure | IC$_{50}$ | EC$_{50}$ |
|---|---|---|
| 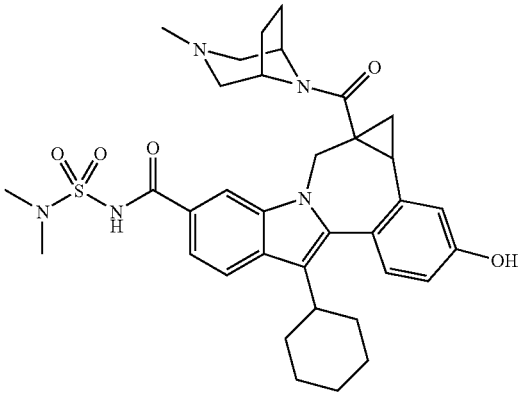 | B | B |
| 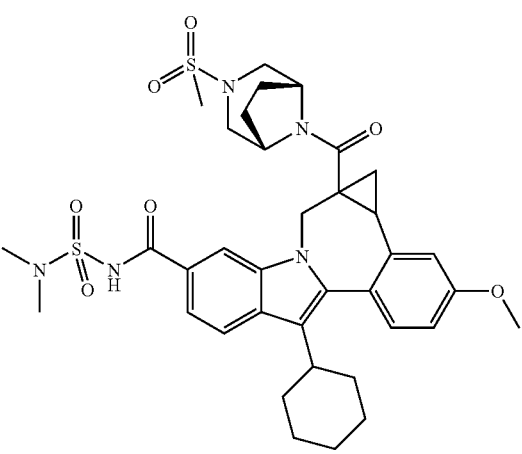 | B | B |
| 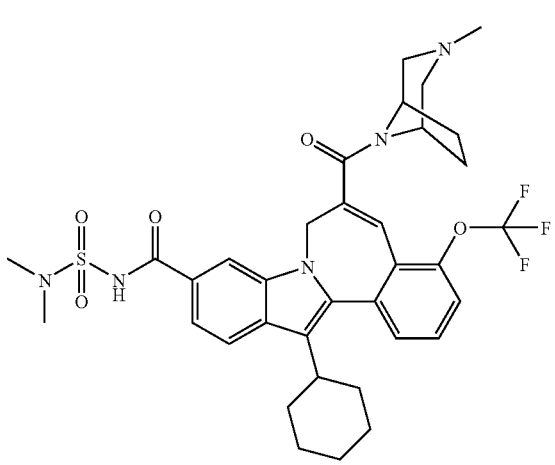 | A | A |

TABLE 1-continued
| Structure | IC$_{50}$ | EC$_{50}$ |
|---|---|---|
| 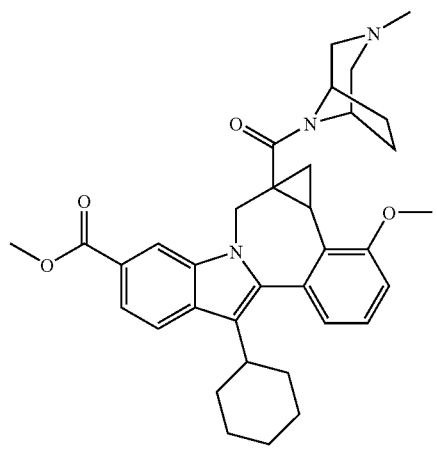 | A | |
| 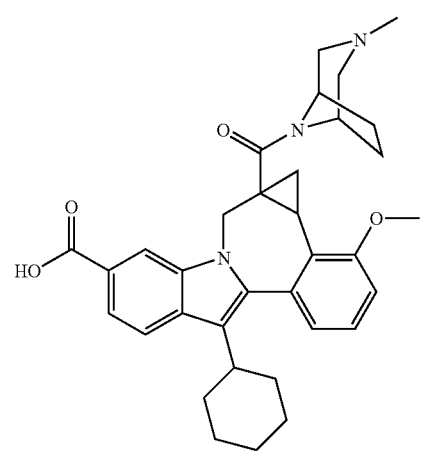 | B | B |
| 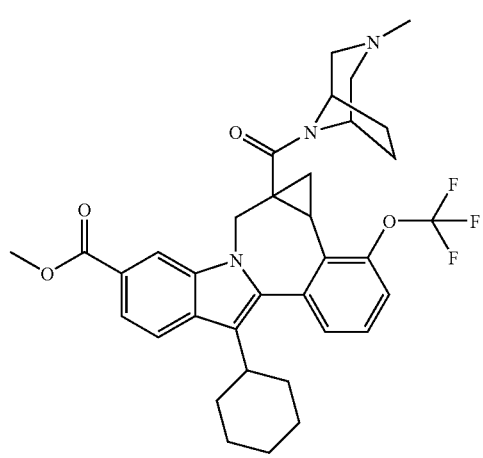 | A | |

TABLE 1-continued

| Structure | IC$_{50}$ | EC$_{50}$ |
|---|---|---|
| | B | A |
| | B | B |
| | B | B |

TABLE 1-continued
| Structure | IC$_{50}$ | EC$_{50}$ |
|---|---|---|
| 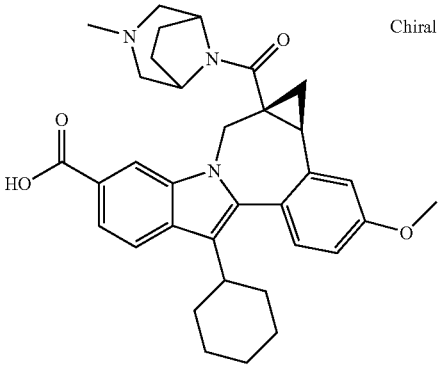 Chiral | | |
| 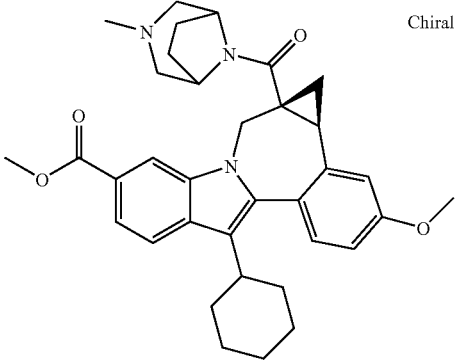 Chiral | | |
| 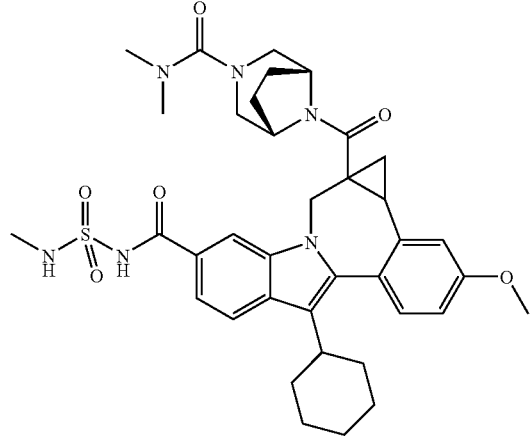 | B | B |

TABLE 1-continued
| Structure | IC$_{50}$ | EC$_{50}$ |
|---|---|---|
| 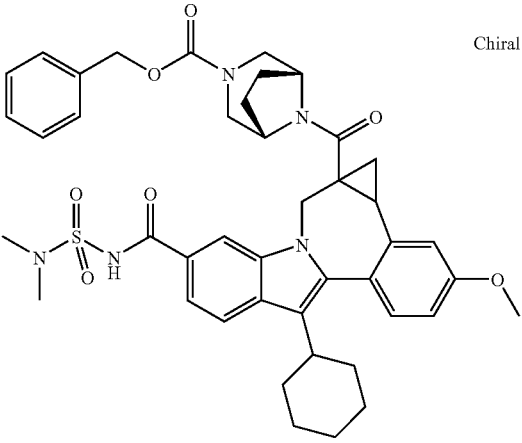 Chiral | B | B |
| 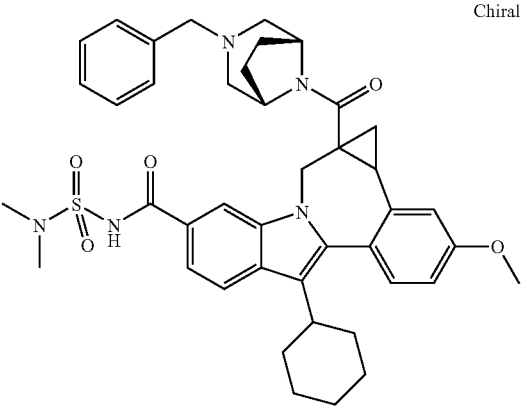 Chiral | B | B |
| 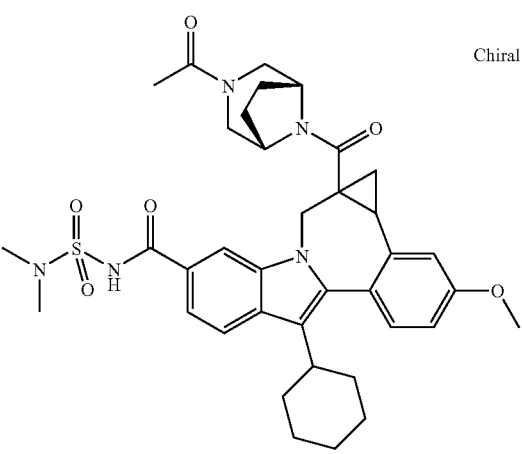 Chiral | B | B |

TABLE 1-continued
| Structure | IC$_{50}$ | EC$_{50}$ |
|---|---|---|
| 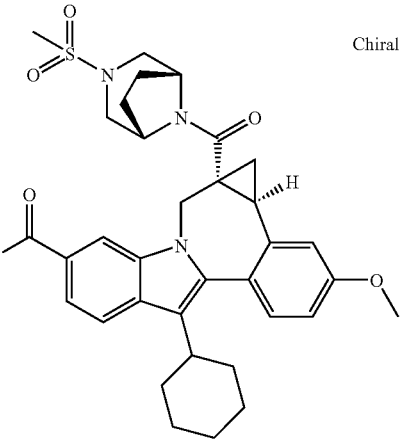 | B | B |
| 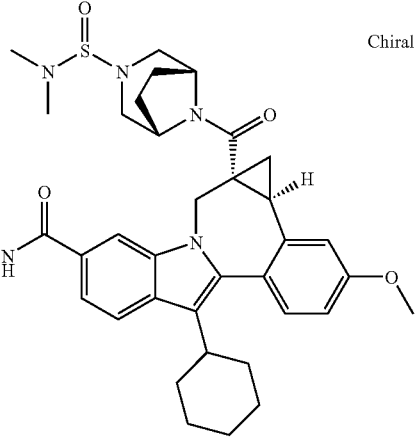 | B | B |
| 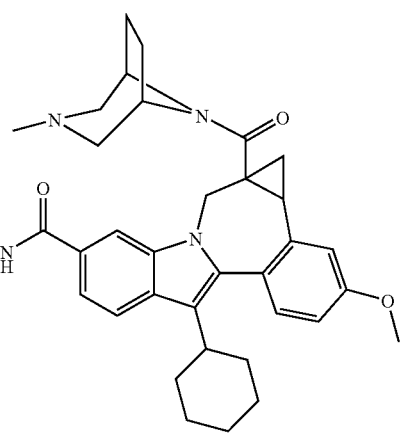 | B | B |

TABLE 1-continued
| Structure | IC₅₀ | EC₅₀ |
|---|---|---|
| 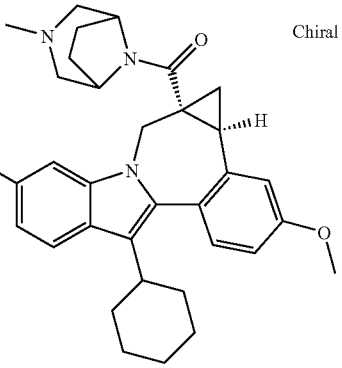 Chiral | A | D |
| 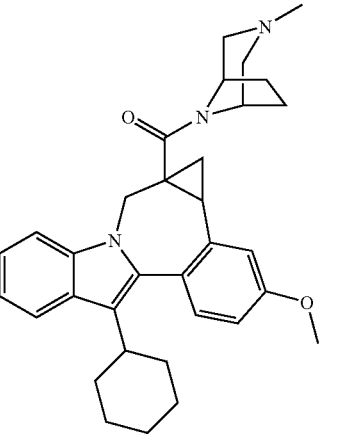 | B | B |
| 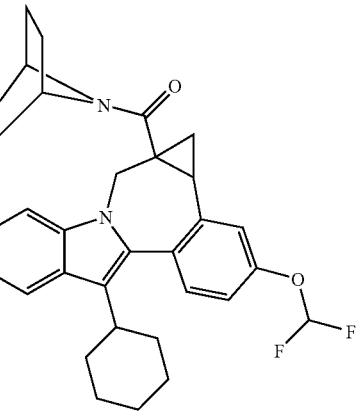 | B | B |

TABLE 1-continued
| Structure | IC$_{50}$ | EC$_{50}$ |
|---|---|---|
| 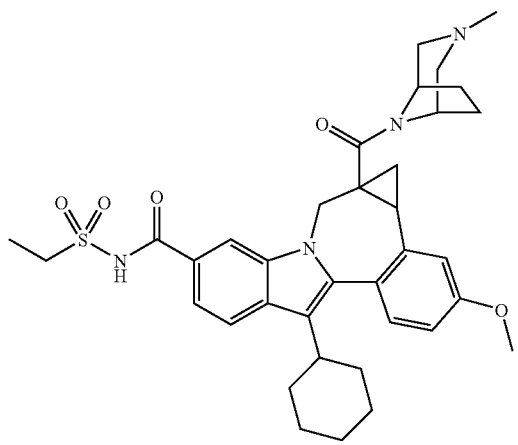 | B | B |
| 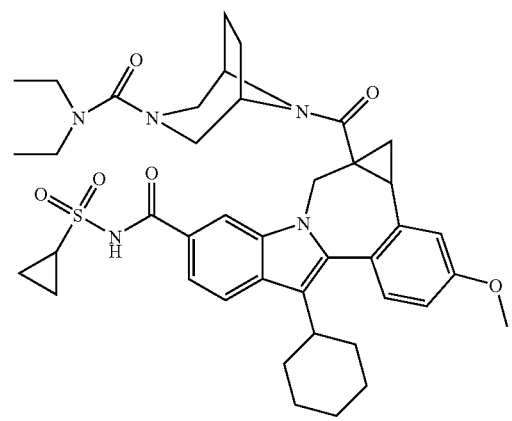 | B | B |
| 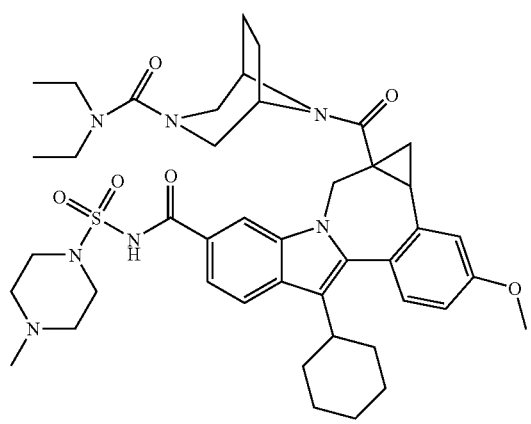 | B | B |

TABLE 1-continued
| Structure | IC$_{50}$ | EC$_{50}$ |
|---|---|---|
| 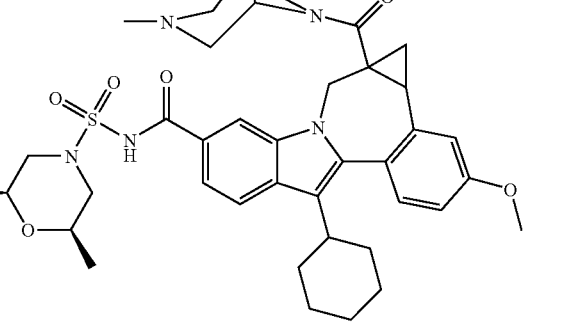 | B | B |
| 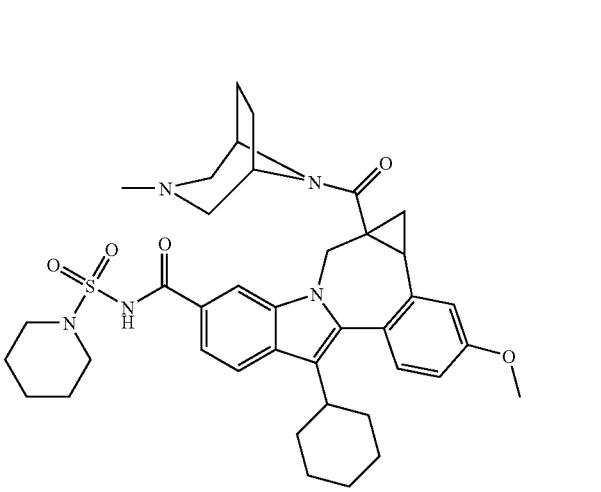 | B | B |
| 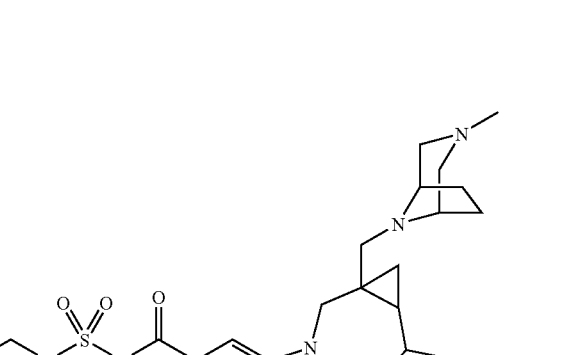 | B | B |

TABLE 1-continued

| Structure | IC$_{50}$ | EC$_{50}$ |
|---|---|---|
| | B | B |
| | B | B |
| | B | B |

A >0.5 μM;
B 0.001 μM-0.5 μM;
C <0.02 μM but an exact value was not determined;
D >0.04 μM; but an exact value was not determined;
IC$_{50}$ values were determined using the preincubation protocol.
EC$_{50}$ values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |

TABLE 2-continued

| Brand Name | Type of Inhibitor or Target | Source Company |
|---|---|---|
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

Unless otherwise specified, analytical LCMS data on the following intermediates and examples were acquired using the following columns and conditions. Stop time: Gradient time +1 minute; Starting conc: 0% B unless otherwise noted; Eluent A: 5% $CH_3CN$/95% $H_2O$ with 10 mM $NH_4OAc$ (for columns A, D and E); 10 % MeOH/90% H₂O with 0.1% TFA (for columns B and C); Eluent B: 95% CH₃CN/5% H₂O with 10 mM NH₄OAc (for columns A, D and E); 90% MeOH/10% H₂O with 0.1% TFA (for columns B and C); Column A: Phenomenex 10μ 4.6×50 mm C18; Column B: Phenomenex C18 10μ 3.0×50 mm; Column C: Phenomenex 4.6×50 mm C18 10μ; Column D: Phenomenex Lina C18 5μ 3.0×50 mm; Column E: Phenomenex 5μ 4.6×50 mm C18.

Intermediate 1

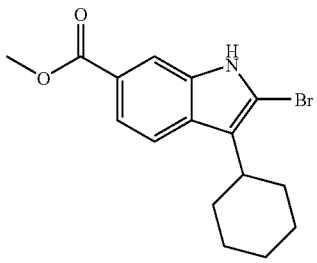

1H-Indole-6-carboxylic acid, 2-bromo-3-cyclohexyl-, methyl ester. Freshly recrystallized pyridinium tribromide (recrystallization from hot AcOH (5 mL per 1 g), rinsed with cold AcOH and dried under high vacuum over KOH) was added in portions (over 10 min.) to a stirring solution of methyl 3-cyclohexyl-1H-indole-6-carboxylate (60 g, 233 mmol) (prepared using procedures describe in WO2004/065367) in CHCl₃/THF (1:1, 1.25 L) at 2° C. The reaction solution was stirred at 0-5° C. for 2.5 h, and washed with sat. aq. NaHSO₃ (1 L), 1 N HCl (1 L) and brine (1 L). The organic layer was dried (MgSO₄) and concentrated. The resulting red oil was diluted with Et₂O and concentrated. The resulting pink solid was dissolved into Et₂O (200 mL) treated with hexanes (300 mL) and partially concentrated. The solids were collected by filtration and rinsed with hexanes. The mother liquor was concentrated to dryness and the procedure repeated. The solids were combined to yield 1H-indole-6-carboxylic acid, 2-bromo-3-cyclohexyl-, methyl ester (64 g, 190 mmol, 82%) as a fluffy pink solid, which was used without further purification. 1HNMR (300 MHz, CDCl₃) δ 8.47 (br s, 1H), 8.03 (d, J=1.4 Hz, 1H), 7.74 (dd, J=1.4, 8.8 Hz, 1H), 7.69 (d, J=8.8 Hz, 1H), 3.92 (s, 3H), 2.82 (tt, J=3.7, 11.7 Hz, 1H), 1.98-1.72 (m, 7H), 1.50-1.27 (m, 3H). 13CNMR (75 MHz, CDCl3) δ 168.2, 135.6, 130.2, 123.1, 120.8, 120.3, 118.7, 112.8, 110.7, 52.1, 37.0, 32.2(2), 27.0 (2), 26.1. LCMS: m/e 334 (M−H)⁻, ret time 3.34 min, column A, 4 minute gradient.

Intermediate 2

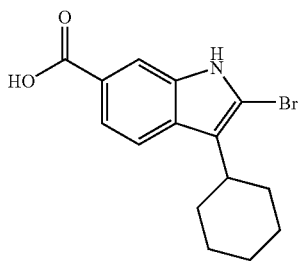

1H-Indole-6-carboxylic acid, 2-bromo-3-cyclohexyl-. A solution of methyl 2-bromo-3-cyclohexyl-1H-indole-6-carboxylate (20 g, 60 mmol) and LiOH (3.8 g, 160 mmol) in MeOH/THF/H₂O (1:1:1, 300 mL) was heated at 90° C. for 2 h. The reaction mixture was cooled in an ice/H₂O bath, neutralized with 1M HCl (~160 mL) diluted with H₂O (250 mL) and stirred for 1 h at rt. The precipitates were collected by filtration rinse with H₂O and dried to yield 1H-indole-6-carboxylic acid, 2-bromo-3-cyclohexyl- (quant.) which was used without further purification.

An alternative procedure that can by used to provide 1H-indole-6-carboxylic acid, 2-bromo-3-cyclohexyl- is described below:

A solution of methyl 2-bromo-3-cyclohexyl-1H-indole-6-carboxylate (117 g, 349 mmol) and LiOH.H₂O (26.4 g, 629 mmol) in MeOH/THF/H2O (1:1:1, 1.8 L) was heated at reflux for 3 h. The reaction mixture was cooled in an ice/H20 bath to ~2° C., neutralized with 1M HCl (~650 mL) (added at such a rate that temperature did not exceed 5° C.), diluted with H2O (1 L) and stirred while warming to ambient temperature. The precipitates were collected by filtration rinsed with H₂O and dried to yield the mono THF solvate of 1H-indole-6-carboxylic acid, 2-bromo-3-cyclohexyl- (135.5 g, 345 mmol, 99%) as a yellow solid, which was used without further purification. 1HNMR (300 MHz, CDCl₃) δ 11.01 (br s, 1H), 8.77 (s, 1H), 8.07 (d, J=1.5 Hz, 1H), 7.82 (dd, J=1.5, 8.8 Hz, 1H), 7.72 (d, J=8.8 Hz, 1H), 3.84-3.74 (m, 4H), 2.89 (m, 1H), 1.98-1.72 (m, 11H), 1.50-1.24 (m, 3H). 13CNMR (75 MHz, CDCl3) δ 172.7, 135.5, 130.7, 122.3, 120.9(2), 118.8, 113.3, 111.1, 67.9(2), 37.0, 32.2(2), 27.0(2), 26.1, 25.5(2). LCMS: m/e 320 (M−H)⁻, ret time 2.21 min, column A, 4 minute gradient.

Intermediate 3

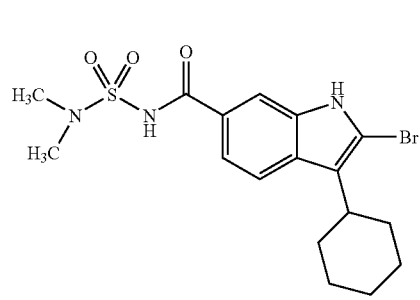

1H-Indole-6-carboxamide, 2-bromo-3-cyclohexyl-N-[(dimethylamino)sulfonyl]-. 1,1′-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22° C. The evolution of CO₂ was instantaneous and when it slowed the solution was heated at 50° C. for 1 hr and then cooled to 22° C. N,N-Dimethylsulfamide (0.94 g, 7.56 mmol) was added followed by the dropwise addition of a solution of DBU (1.34 g, 8.8 mmol) in THF (4 mL). Stirring was continued for 24 hr. The mixture was partitioned between ethyl acetate and dilute HCl. The ethyl acetate layer was washed with water followed by brine and dried over Na₂SO₄. The extract was concentrated to dryness to leave the title product as a pale yellow friable foam, (2.0 g, 74%, >90% purity, estimated from NMR). ¹H NMR (300 MHz, DMSO-D6) δ ppm 1.28-1.49 (m, 3 H) 1.59-2.04 (m, 7 H) 2.74-2.82 (m, 1 H) 2.88 (s, 6 H) 7.57 (dd, J=8.42, 1.46 Hz, 1 H) 7.74 (d, J=8.78 Hz, 1 H) 7.91 (s, 1 H) 11.71 (s, 1 H) 12.08 (s, 1 H).

An alternative method for the preparation of 1H-indole-6-carboxamide, 2-bromo-3-cyclohexyl-N-[(dimethylamino) sulfonyl]- is described below.

To a 1 L four necked round bottom flask equipped with a mechanical stirrer, a temperature controller, a N2 inlet, and a condenser, under N2, was added 2-bromo-3-cyclohexyl-1H-indole-6-carboxylic acid (102.0 g, 0.259 mol) and dry THF (300 mL). After stirring for 10 min, CDI (50.3 g, 0.31 mol) was added portion wise. The reaction mixture was then heated to 50° C. for 2 h. After cooling to 30° C., N,N-dimethylaminosulfonamide (41.7 g, 0.336 mol) was added in one portion followed by addition of DBU (54.1 mL, 0.362 mol) drop wise over a period of 1 h. The reaction mixture was then stirred at rt for 20 h. The solvent was removed in vacuo and the residue was partitioned between EtOAc and 1 N HCl (1:1, 2 L). The organic layer was separated and the aqueous layer was extracted with EtOAc (500 mL). The combined organic layers were washed with brine (1.5 L) and dried over MgSO4. The solution was filtered and concentrated in vacuo to give the crude product (111.0 g). The crude product was suspended in EtOAc (400 mL) at 60° C. To the suspension was added heptane (2 L) slowly. The resulting suspension was stirred and cooled to 0° C. It was then filtered. The filter cake was rinsed with small amount of heptane and house vacuum air dried for 2 days. The product was collected as a white solid (92.0 g, 83%). $^1$H NMR (MeOD, 300 MHz) δ 7.89 (s, H), 7.77 (d, J=8.4 Hz, 1H), 7.55 (dd, J=8.4 and 1.8 Hz, 1H), 3.01 (s, 6H), 2.73-2.95 (m, 1H), 1.81-2.05 (m, 8H), 1.39-1.50 (m, 2H); m/z 429 (M+H)+.

solution was flushed with nitrogen and heated at 70° C. (internal monitoring) overnight and then cooled to rt. The reaction was diluted with EtOAc (1 L) and EtOH (100 mL), washed carefully with 1N aqueous HCl (1 L) and brine (500 mL), dried (MgSO4), filtered and concentrated. The residual solids were stirred with Et2O (600 mL) for 1 h and collected by filtration to yield 1H-indole-6-carboxamide, 3-cyclohexyl-N-[(dimethylamino)sulfonyl]-2-(2-formyl-4-methoxyphenyl)- (52.8 g, 109 mmol, 87%) as a yellow powder which was used without further purification. 1HNMR (300 MHz, d6-DMSO) δ 11.66 (s, 1H), 8.17 (s, 1H), 7.75 (d, J=8.4 Hz, 1H), 7.74 (d, J=8.4 Hz, 1H), 7.59 (dd, J=1.4, 8.4 Hz, 1H), 7.23-7.16 (m, 2H), 7.08 (dd, J=2.6, 8.4 Hz, 1H), 6.54 (d, J=8.8 Hz, 1H), 3.86 (s, 3H), 3.22-3.08 (m, 1H), 2.91 (s, 6H), 2.00-1.74 (m, 7H), 1.60-1.38 (m, 3H). 13CNMR (75 MHz, CDCl3) δ 165.7, 158.8, 147.2, 139.1, 134.3, 132.0, 123.4, 122.0, 119.2, 118.2, 114.8, 112.3, 110.4, 109.8, 79.6, 45.9, 37.2(2), 34.7, 32.0(2), 25.9(2), 24.9. LCMS: m/e 482 (M−H)⁻, ret time 2.56 min, column A, 4 minute gradient.

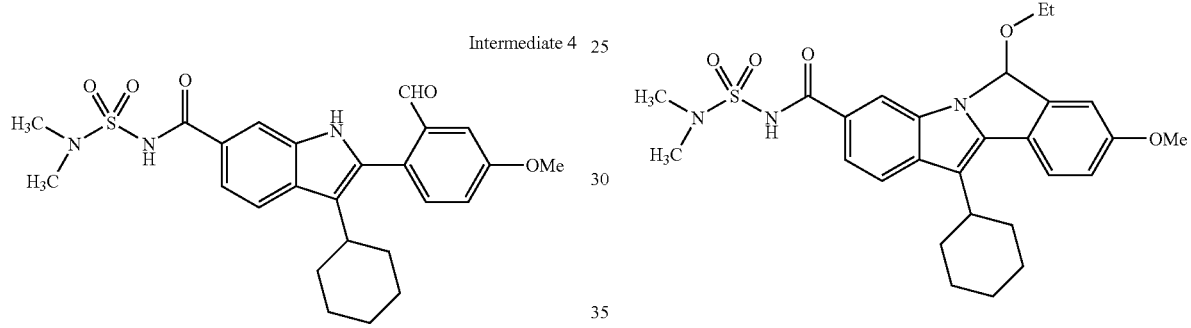

Intermediate 4

Intermediate 5

1H-Indole-6-carboxamide, 3-cyclohexyl-N-[(dimethylamino)sulfonyl]-2-(2-formyl-4-methoxyphenyl)-. A mixture of the 2-Bromo-3-cyclohexyl-N-[(dimethylamino)sulfonyl]-1H-indole-6-carboxamide (4.28g, 0.01 mol), 4-methoxy-2-formylphenyl boronic acid (2.7 g, 0.015 mol), 2-dicyclohexylphosphino-2',6'-dimethoxy-biphenyl (41 mg, 0.0001 mol), palladium acetate (11.2 mg), and finely ground potassium carbonate (4.24 g, 0.02 mol) in toluene (30 mL) was stirred under reflux and under nitrogen for 30 min, at which time LC/MS analysis showed the reaction to be complete. The reaction mixture was then diluted with ethyl acetate and water, and then acidified with an excess of dilute HCl. The ethyl acetate layer was then collected and washed with dilute HCl, water and brine. The organic solution was then dried (magnesium sulfate), filtered and concentrated to give a gum. The gum was diluted with hexanes (250 ml) and ethyl acetate (25 mL), and the mixture was stirred for 20 hr at 22° C. during which time the product was transformed into a bright yellow granular solid (4.8 g) which was used directly without further purification.

An alternative procedure for the preparation of 1H-indole-6-carboxamide, 3-cyclohexyl-N-[(dimethylamino)sulfonyl]-2-(2-formyl-4-methoxyphenyl)- is provided below:

To a slurried solution of 2-bromo-3-cyclohexyl-N-[(dimethylamino)sulfonyl]-indole-6-carboxamide (54.0 g, 126 mmol), 4-methoxy-2-formylphenylboronic acid (29.5 g, 164 mmol) and LiCl (13.3 g, 315 mmol) in EtOH/toluene (1:1, 1 L) was added a solution of Na2CO3 (40.1 g, 379 mmol) in water (380 mL). The reaction mixture was stirred 10 min. and then Pd(PPh3)4 (11.3 g, 10.0 mmol) was added. The reaction 6H-Isoindolo[2,1-a]indole-3-carboxamide, 11-cyclohexyl-N-[(dimethylamino)sulfonyl]-6-ethoxy-8-methoxy-. To a 5 L four necked round bottom flask equipped with a temperature controller, a condenser, a N2 inlet and a mechanical stirrer, was charged toluene (900 mL), EtOH (900 mL), 2-bromo-3-cyclohexyl-N-(N,N-dimethylsulfamoyl)-1H-indole-6-carboxamide (90 g, 0.21 mol), 2-formyl-4-methoxyphenylboronic acid (49.2 g, 0.273 mol) and LiCl (22.1 g, 0.525 mol). The resulting solution was bubbled with N2 for 15 mins. A solution of Na2CO3 (66.8 g, 0.63 mol) in H2O (675 mL) was added and the reaction mixture was bubbled with N2 for another (10 mins). Pd(PPh3)4 (7.0 g, 6.3 mmol) was added and the reaction mixture was heated to 70° C. for 20 h. After cooling to 35° C., a solution of 1 N HCl (1.5 L) was added slowly. The resulting mixture was transferred to a 6 L separatory funnel and extracted with EtOAc (2×1.5 L). The combined organic extracts were washed with brine (2 L), dried over MgSO4, filtered and concentrated in vacuo to give a yellow solid, which was triturated with 20% EtOAc in hexane (450 mL, 50° C. to 0° C.) to give 3-cyclohexyl-N-(N,N-dimethylsulfamoyl)-2-(2-formyl-4-methoxyphenyl)-1H-indole-6-carboxamide(65.9 g) as a yellow solid. HPLC purity, 98%.

The mother liquid from the trituration was concentrated in vacuo. The residue was refluxed with EtOH (50 mL) for 3 h. The solution was then cooled to 0° C. The precipitates were filtered and washed with cooled TBME (5° C.) (20 mL). The filter cake was house vacuum air dried to give a further quantity of the title compound as a white solid (16.0). HPLC purity, 99%. $^1$H NMR (CDCl3, 300 MHz) δ 8.75 (s, 1H), 7.96 (s, 1H), 7.73 (d, J=8.4 Hz, 1H), 7.67 (d, J=8.4 Hz, 1H), 7.45

(dd, J=8.4 and 1.4 Hz, 1H), 7.09 (d, J=2.2 Hz, 1H), 6.98 (dd, J=8.4 and 2.2 Hz, 1H), 6.50 (s, 1H), 3.86 (s, 3H), 3.05 (s, 6H), 2.92-3.13 (m, 3H), 1.85-1.93 (m, 7 H), 1.40-1.42 (m, 3H), 1.05 (t, J=7.1 Hz, 3H). m/z 512 (M+H)+.

Intermediate 6

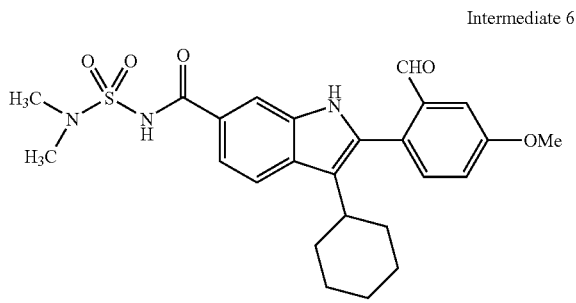

1H-indole-6-carboxamide, 3-cyclohexyl-N-[(dimethylamino)sulfonyl]-2-(2-formyl-4-methoxyphenyl)-. 11-cyclohexyl-N-(N,N-dimethylsulfamoyl)-6-ethoxy-8-methoxy-6H-isoindolo[2,1-a]indole-3-carboxamide was dissolved in THF (75 mL). To the solution was added a solution of 2 N HCl (300 mL). The mixture was vigorously stirred under N2 at rt for 16 h. The resulting suspension was filtered and washed with cooled TBME (2×30 mL). the filer cake was vacuum air dried overnight to give the title compound as a yellow solid. HPLC purity, 99% $^1$H NMR (DMSO-d6, 300 MHz) δ 11.65 (s, 1H), 8.16 (s, 1H), 7.76 (d, J=5.9 Hz, 1H), 7.73 (d, J=5.9 Hz, 1H), 7.58 (dd, J=8.5 and 1.5 Hz, 1H), 7.17-7.20 (m, 2H), 7.08 (dd, J=8.5 and 1.4 Hz, 1H), 6.55 (d, J=8.6 Hz, 1H), 3.86 (s, 3H), 3.14-3.18 (m, 1H), 2.91 (s, 6H), 1.75-1.99 (m, 7H), 1.48-1.60 (m, 3H); m/z 484 (M+H)+.

Intermediate 7

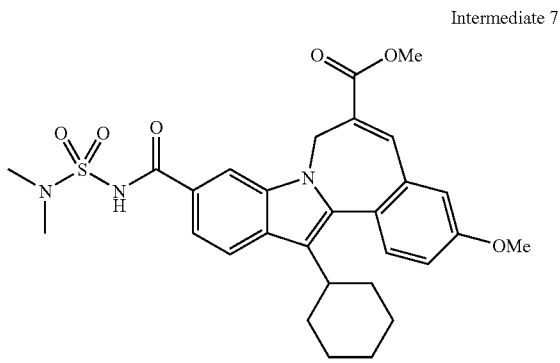

7H-Indolo[2,1-a][2]benzazepine-6-carboxylic acid, 13-cyclohexyl-10-[[[(dimethylamino)sulfonyl]amino]carbonyl]-3-methoxy-, methyl ester. A mixture of the 3-cyclohexyl-N-(N,N-dimethylsulfamoyl)-2-(2-formyl-4-methoxyphenyl)-1H-indole-6-carboxamide (4.8 g, 0.01 mol), methyl 2-(dimethoxyphosphoryl)acrylate (9.7 g, 0.02 mol) and cesium carbonate (7.1 g, 0.02 mol) in DMF (28 mL) was stirred for 20 hr at an oil bath temperature of 55° C. The mixture was poured into ice-water and acidified with dilute HCl to precipitate the crude product. The solid was collected, dried and flash chromatographed on SiO$_2$ (110 g) using an ethyl acetate and methylene chloride (1:10) solution containing 2% acetic acid. Homogeneous fractions were combined and evaporated to afford the title compound as a pale yellow solid (3.9 g, 71% yield). MS: 552 (M=H+).

An alternate procedure for the preparation of 7H-indolo[2,1-a][2]benzazepine-6-carboxylic acid, 13-cyclohexyl-10-[[[(dimethylamino)sulfonyl]amino]carbonyl]-3-methoxy-, methyl ester is provided below.

A solution of 11-cyclohexyl-N-[(dimethylamino)sulfonyl]-6-hydroxy-8-methoxy-6H-isoindolo[2,1-a]indole-3-carboxamide (cyclic hemiaminal) (63.0 g, 130 mmol), methyl 2-(dimethoxyphosphoryl)acrylate (60 g, 261 mmol), cesium carbonate (106 g, 326 mmol) in DMF (400 mL) was heated at 60° C. (bath temp) for 4.5 h. Additional methyl 2-(dimethoxyphosphoryl)acrylate (15 g, 65 mmol) and cesium carbonate (21.2 g, 65 mmol) were added and the reaction was heated at 60° C. overnight then and cooled to rt. The stirring reaction mixture was diluted with H$_2$O (1 L), slowly neutralized with 1N aqueous HCl (800 mL), stirred 3 h, and then the precipitates were collected by filtration. The solids were triturated with Et2O (800 mL) and dried to yield methyl 7H-indolo[2,1-a][2]benzazepine-6-carboxylic acid, 13-cyclohexyl-10-[[[(dimethylamino)sulfonyl]amino]carbonyl]-3-methoxy-, methyl ester (70.2 g, 127 mmol, 98%) as a yellow solid which was used without further purification. 1HNMR (300 MHz, CDCl3) δ 8.67 (s, 1H), 8.09 (s, 1H), 7.86 (d, J=8.4 Hz, 1H), 7.80 (s, 1H), 7.50 (d, J=8.4 Hz, 1H), 7.42 (d, J=8.8 Hz, 1H), 7.08 (dd, J=2.6, 8.8 Hz, 1H), 6.98 (d, J=2.6 Hz, 1H), 5.75-5.51 (m, 1H), 4.29-4.01 (m, 1H), 3.89 (s, 3H), 3.82 (s, 3H), 3.05 (s, 6H), 2.87-2.73 (m, 1H), 2.11-1.12 (m, 10H). LCMS: m/e 550 (M−H)−, ret time 3.21 min, column A, 4 minute gradient.

Intermediate 8

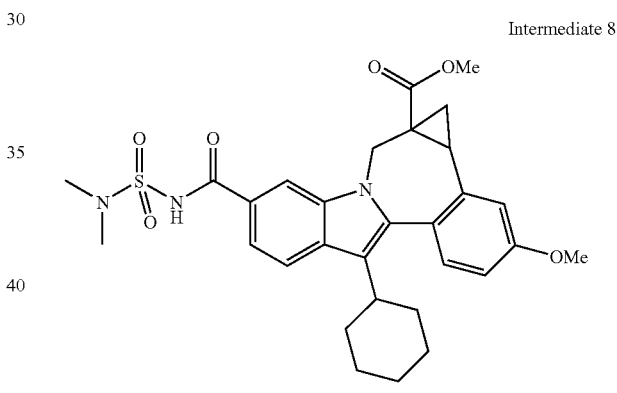

Cycloprop[d]indolo[2,1-a][2]benzazepine-1a(2H)-carboxylic acid, 8-cyclohexyl-5-[[[(dimethylamino)sulfonyl]amino]carbonyl]-1,2b-dihydro-11-methoxy-, methyl ester, (+/−)-. DMSO (5 mL) was added to a mixture of trimethylsulfoxonium iodide (199 mg, 0.906 mmol) and NaH (38 mg in 60% oil dispersion, 0.953 mmol) in a round-bottomed flask. The reaction mixture was stirred at rt for 0.5 hr. 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (125 mg, 0.227 mmol) was then added and the reaction mixture was stirred at rt. for 3 hr., and then at 50° C. for a further 3 hr. The reaction was then quenched with water and acidified with 1N HCl solution. The crude product then precipitated as a light yellow solid which was collected by filtration and air dried, (106 mg, 83% yield). 6 mg of this material was then purified by Prep. HPLC to afford the title compound as a light yellow solid (1.8 mg). MS m/z 566(MH+), Retention time: 3.850 min.1H NMR (500 MHz, MeOD) δ ppm 0.28 (m, 0.36 H) 1.19-2.20 (m, 11.64 H) 2.70-3.02 (m, 2 H) 3.03 (s, 2.16 H) 3.05 (s, 3.84 H) 3.49 (d, J=15.26 Hz, 0.64 H) 3.54 (s, 1.92 H) 3.83 (s, 1.08 H) 3.91 (s, 3 H) 4.08 (d, J=15.26 Hz, 0.36 H) 5.29 (d, J=15.26 Hz, 0.36

H) 5.50 (d, J=14.95 Hz, 0.64 H) 6.98-7.06 (m, 1 H) 7.16 (d, J=2.44 Hz, 0.36 H) 7.23 (d, J=2.44 Hz, 0.64 H) 7.30 (d, J=8.55 Hz, 0.64 H) 7.34 (d, J=8.55 Hz, 0.36 H) 7.56 (dd, J=8.55, 1.53 Hz, 0.64 H) 7.63 (dd, J=8.55, 1.53 Hz, 0.36 H) 7.88 (d, J=8.55 Hz, 0.64 H) 7.91 (d, J=8.55 Hz, 0.36 H) 8.12 (s, 0.36 H) 8.33 (d, J=1.53 Hz, 0.64 H).

An alternative procedure for the preparation of the title compounds is provided below.

To a flame dried, four necked, 1 L round bottom flask equipped with a mechanical stirrer, N2 inlet and a thermometer, under N2, was charged sodium hydride (95%) (3.09 g, 129.2 mmol) and dry DMF (200 mL). With vigorous stirring, trimethylsulfoxonium iodide (32.5 g, 147.3 mmol) portion wise during which time the temperature rose to 30° C. After stirring for 30 mins, a solution of 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (33.8 g, 61.3 mmol) in dry DMF (70 mL) was added quickly. The reaction mixture was stirred below 30° C. for 30 mins and then poured into an ice cold solution of 1 N HCl (130 mL) in H2O (2 L) portion wise. After the resulting suspension was mechanically stirred for 1 h, the precipitates were filtered and the filter cake was washed with H2O (100 mL). The filter cake was partitioned between EtOAc and 0.5 N HCl (1:1, 4 L). The organic phase was separated, washed with H2O (1 L) and brine (1 L), dried over $MgSO_4$, filtered and concentrated in vacuo. The residue was dissolved in EtOAc (150 mL), and the solution was filtered through a silica gel pad (300 in hexane) and rinsed with 50% EtOAc in hexane (5 L). The filtrate was concentrated in vacuo to give a slightly yellow solid which was triturated with 10% EtOAc in TBME (220 mL) from 50° C. to 0° C. to to give cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (+/−)- as a white solid (26.1 g, 75% yield). HPLC purity, 100%. $^1$H NMR (DMSO-$d_6$, 300 MHz) δ 11.61 (s, 1H), 8.47 (s, 0.5H), 8.25 (s, 0.5H), 7.81-7.88 (m, 1H), 7.57-7.63 (m, 1H), 7.23-7.29 (m, 2H), 7.01-7.07 (m, 1H), 5.43 (d, J=15.0 Hz, 0.5H), 5.22 (d, J=15 Hz, 0.5H), 4.04 (dd, J=15.4 and 6.6 Hz, 0.5H), 3.83 (s, 3H), 3.75 (s, 1H), 3.08-3.47 (m, 0.5H), 3.29 (s, 3H), 2.73-2.92 (m, 8H), 1.11-1.99 (m, 10.5H), 0.20 (m, 0.5H); m/z 566 (M+H)$^+$.

Intermediate 9

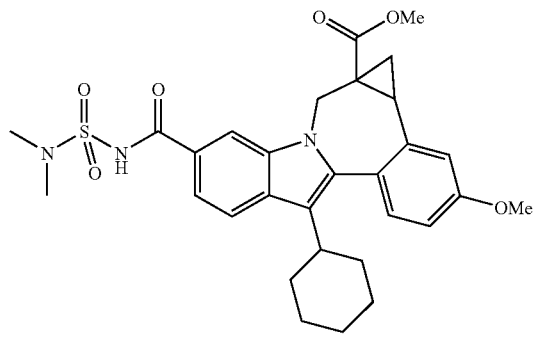

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (−)-. A sample of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-methyl ester was dissolved in EtOH/CH$_3$CN 1/1+0.5% DEA at a concentration of 50 mg/ml. [The addition of DEA ensures the compound remains in solution during the injection process]. This solution was then injected onto a Thar SFC-350 preparative SFC under the conditions shown below.

Preparative conditions on Thar SFC-350: Column: Chiralcel OJ-H 5×25 cm; mobile phase: 25% MeOH/CH3CN (1/1) in CO2; pressure (bar): 100; flow rate (ml/min): 240; solution concentration (mg/ml): 50; injection amount (ml): 4.5-5; Cycle time (min/inj): 6.5-7; Temperature (° C.): 45; throughput (g/ hr): ~2; Detector wavelength (nm): 254.

From 371.4 of racemic starting material, a total of 177.3 of the desired second eluting (−) isomer was obtained, containing ~1 Meq of diethylamine. This material was purified using the following procedure. The mixture (24.7 g) dissolved in dichloromethane (800 mL)) was washed sequentially with; 0.5 N HCl (1×400 mL, 1×240 mL), H$_2$O (2×240 mL), and brine (2×240 mL). The organic layer was then dried (Anhy. Na$_2$SO$_4$), filtered and evaporated to give 22.33 of (cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (−)- as a yellow solid (92% recovery). HPLC$^1$>99% (Rt 2.38 min); LC/MS (ES$^+$) 566.51 (M+H, 100); $[\alpha]_D^{25\,C}$ −194.64° (c 1.03, MeOH). Anal. Calcd for C$_{30}$H$_{35}$N$_3$O$_6$S.0.33H$_2$O: C, 63.04; H, 6.29; N, 7.35; S, 5.61; H$_2$O, 1.04. Found C, 63.07; H, 6.01; N, 7.24; S, 5.58; H$_2$O, 1.03. The NMR shows the absence of Et$_2$NH. The EE of this material was determined to be >99% using the following analytical HPLC procedure.

Analytical conditions of ee determination on Thar analytical SFC. Analytical Column: Chiralcel OJ (0.46×25 cm, 10 μl); BPR pressure: 100 bars; Temperature: 35° C.; Flow rate: 3.0 ml/min; Mobile Phase: 15% MeOH/CH$_3$CN (1/1) in CO$_2$; Detector Wavelength: 254 nm; Retention time (min): 4, 6.5.

Intermediate 10

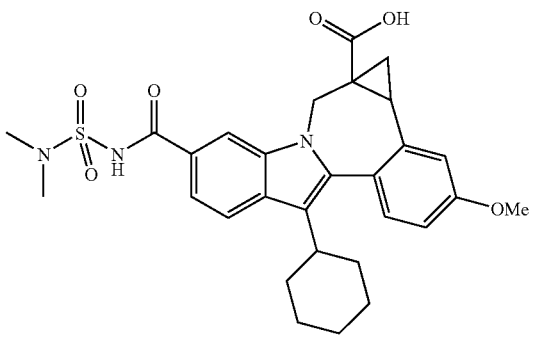

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (−)-. To a solution of (−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester (22.33 g, 39.5 mmol) in MeOH (300 mL) was added 1 N NaOH (120 mL) slowly over 20 min., while maintaining the reaction temperature <30° C. The mixture was stirred at rt under N$_2$ for 18 h. The HPLC indicated the reaction was complete. To the reaction solution was added 1 N HCl (130 mL). After addition was complete, the pH of the reaction mixture was about 2. The methanol in the reaction mixture was evaporated. Water (300 mL) was added to the mixture which was then extracted with CH$_2$Cl$_2$ (1×600 mL, 1×200 mL). The combined extracts were washed with H$_2$O (2×300 mL), brine (2×300 mL), dried (Na$_2$SO$_4$) and evaporated to give 20.82 (96% yield) of the title compound as a yellow solid. HPLC conditions column: Phenomenoex Synergi Polar-RP 4 um 4.6×50 mm; UV: 220 nm; gradient time: 4 min; flow rate: 4 mL/min, 75-100% B; solvent A: 10%

MeOH/90% H₂O with 0.2% H₃PO₄, solvent B: 90% MeOH/10% H₂O with 0.2% H₃PO₄. HPLC >99% (Rt 1.80 min.) LC/MS (ES⁺) 552.25 (M+H, 100); [α]$_D^{25\,C}$ −166.99°(c 1.00, MeOH). GC analysis: CH₂Cl₂ 4.94%; Anal. Calcd for C₂₉H₃₃N₃O₆S.0.16H₂O.0.35CH₂Cl₂: C, 60.37; H, 5.87; N, 7.20; S, 5.49; H₂O, 0.49; CH₂Cl₂, 5.02. Found: C, 59.95; H, 5.89; N, 7.03; S, 5.38; H₂O, 0.47; CH₂Cl₂, 4.94.

Intermediate 11

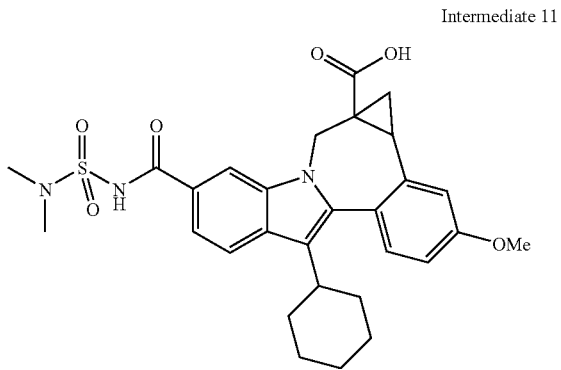

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (+/−)-. To a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester (100 mg, 0.177 mmol) in THF/Methanol mixture (2.0 mL/2.0 mL), 2N NaOH solution (1.0 mL) was added. The reaction mixture was heated at 90° C. under microwave conditions for 5 min. It was then concentrated, acidified with 1N HCl solution and extracted with ethyl acetate (2×20 mL). The organic layers were combined, dried (MgSO₄), filtered and concentrated. The residue was purified by preparative HPLC to afford the desired product as a light yellow solid, (59 mg, 60% yield). MS m/z 552(MH⁺), Retention time: 3.850 min. 1H NMR (300 MHz, MeOD) δ ppm 0.25 (m, 0.38 H) 1.14-2.22 (m, 11.62 H) 2.69-2.98 (m, 2 H) 3.02 (s, 2.28 H) 3.02 (s, 3.72 H) 3.41 (d, J=15.00 Hz, 0.62 H) 3.88 (s, 3 H) 4.01 (d, J=15.00 Hz, 0.38 H) 5.26 (d, J=15.00 Hz, 0.38 H) 5.45 (d, J=14.64 Hz, 0.62 H) 6.94-7.02 (m, 1 H) 7.13 (d, J=2.56 Hz, 0.38 H) 7.21 (d, J=2.20 Hz, 0.62 H) 7.26 (d, J=8.42 Hz, 0.62 H) 7.30 (d, J=8.78 Hz, 0.38 H) 7.53 (dd, J=8.42, 1.46 Hz, 0.62 H) 7.61 (dd, J=8.60, 1.65 Hz, 0.38 H) 7.85 (d, J=8.42 Hz, 0.62 H) 7.89 (d, J=8.42 Hz, 0.38 H) 8.10 (s, 0.38 H) 8.28 (d, J=1.46 Hz, 0.62 H).

Intermediate 12

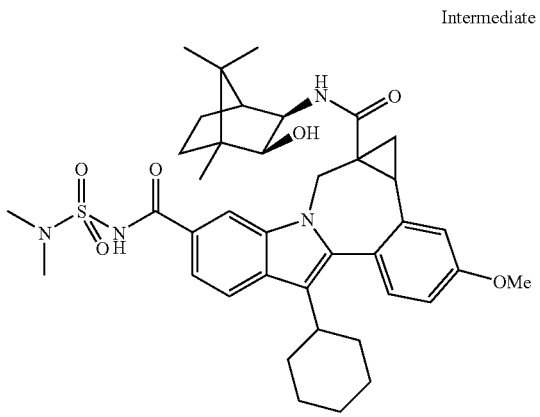

Cycloprop[d]indolo[2,1-a][2]benzazepine-1a, 5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aR)-[partial]-. TBTU (437 mg, 1.36 mmol) and DIPEA (0.95 mL, 5.436 mmol) were added to a solution of (−/+) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (500 mg, 0.906 mmol) in DMSO (20.0 mL). The reaction mixture was stirred at rt for 15 min. (2S,3R)-3-Amino-1,7,7-trimethylbicyclo[2.2.1]heptan-2-ol (280 mg, 1.36 mmol) was then added and the reaction mixture was stirred at rt overnight. The reaction mixture was quenched with water and acidified with 1N HCl solution. A brown solid separated which was collected by filtration. This material was then fractionated by Preparative HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aR)-[partial]- elutes before Cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aS)-[partial]- under the HPLC conditions described above. Product obtained as a light yellow solid, 230 mg, 36% yield). MS m/703(MH⁺), Retention time: 3.936 min. 1H NMR (500 MHz, MeOD) δ ppm 0.14-0.24 (m, 2.64 H) 0.51 (s, 2.46 H) 0.72-2.21 (m, 20.9 H) 2.49 (m, 0.18 H) 2.62 (m, 0.82 H) 2.85 (m, 0.18 H) 2.96 (m, 0.82 H) 3.03 (s, 6 H) 3.39 (m, 0.82 H) 3.49-3.58 (m, 1.64 H) 3.71-3.80 (m, 0.36 H) 3.90 (s, 3 H) 4.17 (d, J=14.65 Hz, 0.18 H) 5.06 (d, J=14.65 Hz, 0.18 H) 5.37 (d, J=14.95 Hz, 0.82 H) 6.73 (d, J=5.49 Hz, 0.82 H) 6.98-7.05 (m, 1 H) 7.08 (d, J=4.58 Hz, 0.18 H) 7.10 (d, J=2.44 Hz, 0.18 H) 7.21 (d, J=2.44 Hz, 0.82 H) 7.31 (d, J=8.55 Hz, 0.82 H) 7.34 (d, J=8.55 Hz, 0.18 H) 7.59-7.64 (m, 1 H) 7.87-7.93 (m, 1 H) 7.99 (s, 0.18 H) 8.09 (d, J=1.22 Hz, 0.82 H).

Intermediate 13

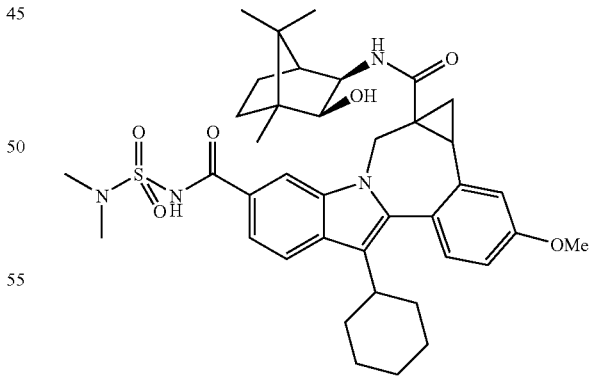

Cycloprop[d]indolo[2,1-a][2]benzazepine-1a, 5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aS)-[partial]-. TBTU (437 mg, 1.36 mmol) and DIPEA (0.95 mL, 5.436 mmol) were added to a solution of (−/+) cycloprop[d]indolo[2,1-a][2]benzazepine-1a(2H)-carboxylic acid, 8-cyclohexyl-5-

[[[(dimethylamino)sulfonyl]amino]carbonyl]-1,12b-dihydro-11-methoxy- (500 mg, 0.906 mmol) in DMSO (20.0 mL). The reaction mixture was stirred at rt for 15 min. Then (2S,3R)-3-amino-1,7,7-trimethylbicyclo[2.2.1]heptan-2-ol (280 mg, 1.36mmol) was added, and the reaction mixture was stirred at rt overnight. The reaction mixture was quenched with water and then acidified with 1N HCl solution. A brown colored solid separated that was collected by filtration. This material was then fractionated by preparative HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aS)-[partial]- elutes after cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3 S)-3-hydroxy-4,7,7-trimethylbicyclo[2.2.1]hept-2-yl]-1-methoxy-, (1aR)-[partial]- under the HPLC conditions described above. Product obtained as a light yellow solid, 215 mg, 34% yield). MS m/703(MH$^+$), Retention time: 4.038 min. 1H NMR (500 MHz, MeOD) δ ppm 0.20 (m, 0.38H) 0.75 (s, 1.86 H) 0.76 (s, 1.86 H) 0.84 (s, 1.86 H) 0.85 (s, 1.14 H) 0.89-2.18 (m, 18.9 H) 2.52 (m, 0.38 H) 2.70 (m, 0.62 H) 2.85 (m, 0.38 H) 2.97 (m, 0.62 H) 3.03 (s, 2.28 H) 3.04 (s, 3.72 H) 3.33-3.39 (m, 0.62 H) 3.43-3.51 (m, 1.24 H) 3.73-3.77 (m, 0.38 H) 3.78-3.84 (m, 0.38 H) 3.90 (s, 1.86 H) 3.90 (s, 1.14 H) 4.14 (d, J=14.65 Hz, 0.38 H) 5.11 (d, J=14.65 Hz, 0.38 H) 5.44 (d, J=15.26 Hz, 0.62 H) 6.68 (d, J=4.88 Hz, 0.62 H) 6.96-7.03 (m, 1 H) 7.07 (d, J=5.19 Hz, 0.38 H) 7.12 (d, J=2.44 Hz, 0.38 H) 7.23 (d, J=2.14 Hz, 0.62 H) 7.27 (d, J=8.54 Hz, 0.62 H) 7.33 (d, J=8.54 Hz, 0.38 H) 7.55 (dd, J=8.39, 1.68 Hz, 0.62 H) 7.62 (dd, J=8.55, 1.53 Hz, 0.38 H) 7.87 (d, J=8.54 Hz, 0.62 H) 7.91 (d, J=8.55 Hz, 0.38 H) 8.08 (d, J=1.22 Hz, 0.38 H) 8.10 (d, J=1.22 Hz, 0.62 H).

Intermediate 14

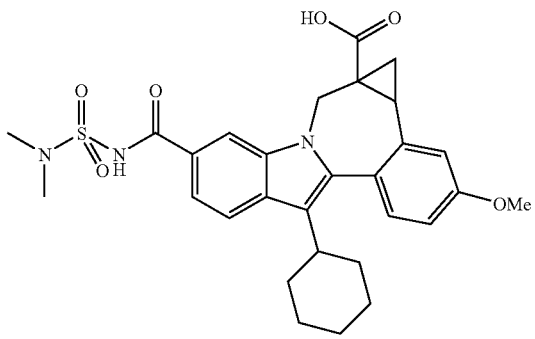

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (−)-. 10 N NaOH (2.0 mL, 20 mmol) solution and 4 mL of water were added to a solution of cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1 aR)-[partial]- (160 mg, 0.228 mmol) in THF/MeOH (7 mL/7 mL). The reaction mixture was heated at 120° C. under microwave conditions for 1 hr. It was then concentrated, acidified with conc. HCl solution and extracted with ethyl acetate twice (2×30 mL). The organic layers were combined, dried (MgSO$_4$), filtered and concentrated in vacuo to an orange oil. The crude product was then purified by Prep. HPLC column to afford the product a light yellow solid, (80 mg, 64% yield). Average specific rotation −130.85°; Solvent MeOH; Wavelength 589 nm; 50 cm cell. MS m/552(MH$^+$), Retention time: 3.760 min. 1H NMR (500 MHz, MeOD) δ ppm 0.27 (m, 0.38H) 1.14-2.22(m,(m, 0.38H)2.80-2.92(m, 1H)2.92-3.09 (m, 6.62 H) 3.45 (d, J=14.95 Hz, 0.62 H) 3.90 (s, 1.86 H) 3.91 (s, 1.14 H) 4.04 (d, J=15.26 Hz, 0.38 H) 5.28 (d, J=15.26 Hz, 0.38 H) 5.47 (d, J=15.26 Hz, 0.62 H) 6.95-7.05 (m, 1 H) 7.15 (d, J=2.75 Hz, 0.38 H) 7.23 (d, J=1.83 Hz, 0.62 H) 7.28 (d, J=8.55 Hz, 0.62 H) 7.33 (d, J=8.54 Hz, 0.38 H) 7.54 (dd, J=8.39, 1.68 Hz, 0.62 H) 7.63 (dd, J=8.55, 1.53 Hz, 0.38 H) 7.86 (d, J=8.55 Hz, 0.62 H) 7.91 (d, J=8.55 Hz, 0.38 H) 8.11 (d, J=1.22 Hz, 0.62 H) 8.29 (d, J=1.22 Hz, 0.38 H).

Intermediate 15

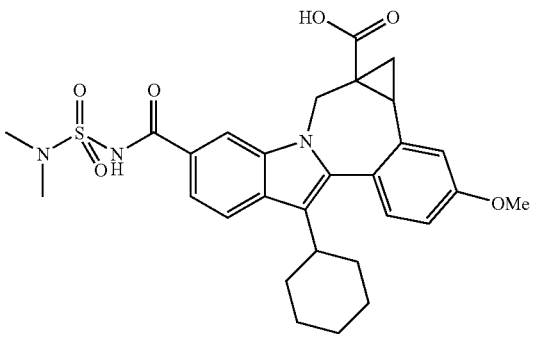

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (+)-. 10 N NaOH (1.8 mL, 18 mmol) solution and 4 mL of water were added to a solution of cycloprop[d]indolo[2,1-a][2]benzazepine-1a,5(2H)-dicarboxamide, 8-cyclohexyl-$N^5$-[(dimethylamino)sulfonyl] -112b-dihydro-$N^{1a}$-[(2R,3S)-3-hydroxy-4,7,7-trimethylbicyclo[2.2.1]hept-2-yl]-11-methoxy-, (1aS)-[partial]- (130 mg, 0.185 mmol) in bTHF/MeOH (7 mL/7 mL). The reaction mixture was heated at 120° C. under microwave conditions for 1 hr. It was concentrated, acidified with conc. HCl solution and extracted with ethyl acetate twice (2×30 mL). The organic layers were combined, dried (MgSO$_4$), filtered and concentrated in vacuo to give an orange oil. The crude product was then purified by Prep. HPLC column to afford the product as a light yellow solid, (68 mg, 67% yield). Average specific rotation +174.73°; Solvent MeOH; Wavelength 589 nm; 50 cm cell MS m/552(MH$^+$), Retention time: 3.773 min. 1H NMR (500 MHz, MeOD) δ ppm 0.27 (m, 0.38H) 1.14-2.22 (m, 11.62 H) 2.76 (m, 0.38 H) 2.80-2.92 (m, 1 H) 2.92-3.09 (m, 6.62 H) 3.45 (d, J=14.95 Hz, 0.62 H) 3.90 (s, 1.86 H) 3.91 (s, 1.14 H) 4.04 (d, J=15.26 Hz, 0.38 H) 5.28 (d, J=15.26 Hz, 0.38 H) 5.47 (d, J=15.26 Hz, 0.62 H) 6.95-7.05 (m, 1 H) 7.15 (d, J=2.75 Hz, 0.38 H) 7.23 (d, J=1.83 Hz, 0.62 H) 7.28 (d, J=8.55 Hz, 0.62 H) 7.33 (d, J=8.54 Hz, 0.38 H) 7.54 (dd, J=8.39, 1.68 Hz, 0.62 H) 7.63 (dd, J=8.55, 1.53 Hz, 0.38 H) 7.86 (d, J=8.55 Hz, 0.62 H) 7.91 (d, J=8.55 Hz, 0.38 H) 8.11 (d, J=1.22 Hz, 0.62 H) 8.29 (d, J=1.22 Hz, 0.38 H).

Intermediate 16

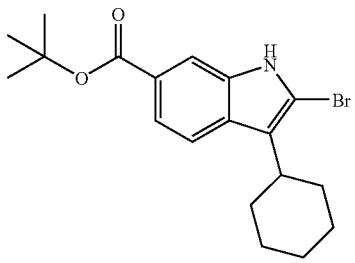

1H-Indole-6-carboxylic acid, 2-bromo-3-cyclohexyl-, 1, 1-dimethylethyl ester. To a mechanically stirred solution of 2-bromo-3-cyclohexyl-1H-indole-6-carboxylic acid (80 g, 0.24 m) in dry methylene dichloride(1.2 L) and THF (100 mL) were added activated molecular sieves (4 A, 80 g) and silver carbonate (275 g, 0.99 m). The reaction mixture was cooled to 0° C. and t-Butyl bromide (142 g, 1.04 m) was added drop wise. The mixture was stirred overnight at rt and monitored by TLC (Hexane-Ethyl acetate 80:20, Rf (Product) =0.7). If any bromo acid was left unconverted a further 10% of silver carbonate was added and stirring was continued for an addition 2-4 h. On completion, the reaction mixture was filtered through a thin bed of celite. The filtrand was washed with methylene dichloride (500 mL). The combined filtrates were concentrated in-vacuo, and the crude product thus obtained was purified by silica gel chromatography: (230-400 mesh, eluted with a gradient of ethyl acetate in pet ether 0-2%). Homogeneous fractions were combined and evaporated under reduced pressure to give 80 (85%) of the title compound. HPLC: 90.1% (RT=6.56 min), Column: C18 BDS, (50×4.6 mm), Mobile Phase: Gradient of 0.1% TFA in water: ACN (30→100→30), Flow rate 0.8 mL/min. LCMS: 99.8% (RT=4.44 min), Column: Geneis, C18 50×4.6 mm Mobile Phase:Gradient of 0.1% Formic acid in water: ACN (70→95→70), Flow rate: 0.8 mL/min; M−1=376.5; $^1$H NMR CDCl$_3$) (400 MHz) δ 1.37-1.40 (m, 3H, cyc.Hexyl), 1.62 (s, 9H, t-Bu), 1.80-1.94 (two sets of m, 3H, & 4H respectively, cyc.Hexyl part), 2.81 (m, 1H, CH of cyc.Hexyl-benzylic), 7.70-7.75 (m, 2H, Indole-H$_4$&$_5$), 8.04 (s, 1H, Indole-H$_7$), 8.52 (s, 1H, Indole-NH).

Intermediate 17

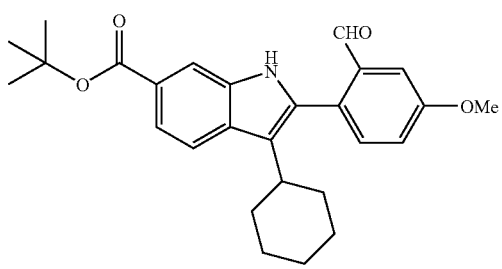

1H-Indole-6-carboxylic acid, 3-cyclohexyl-2-(2-formyl-4-methoxyphenyl)-, 1,1-dimethylethyl ester. tert-Butyl 2-bromo-3-cyclohexyl-1H-indole-6-carboxylate (72 g, 0.19 m) was dissolved in a 1:1 mixture of toluene and ethanol (720 mL) and degasified. LiCl (23.9 g, 0.51 m) was then added, followed by sodium carbonate (720 mL, 1.0 M solution degasified separately,) and Pd-tetrakis (13.1 g, 0.011 m). After stirring for 0.25 h, 2-formyl-4-methoxyphenylboronic acid (41.1 g, 0.22 m) was added and the reaction mixture was heated to 85° C. for 4 h. The reaction was then monitored by TLC, (Hexane-Ethyl acetate 80:20, Rf (Product)=0.55). On completion, the reaction mixture was cooled to rt and water (1.0 L) was added followed by ethyl acetate (1.0 L). The organic layer was washed with brine, and dried and concentrated under vacuum to afford the title compound as a yellow solid. Yield 75 (74%). HPLC: 99.7% (RT=6.30 min), Column: C18 BDS (4.6×50 mm), SC-307, Mobile Phase: Gradient of 0.1% TFA in water: ACN (30→100→30), Flow rate 0.8 mL/min. LCMS: 98.0% (RT=5.28 min), Column: Geneis, C18 (50×4.6 mm), Mobile Phase: Gradient of 0.1% Formic acid in water: ACN (70→95→70), Flow rate: 0.8 mL/min; M−1=432.2; $^1$H NMR (DMSO -d$_6$) (400 MHz) δ 1.40-1.48 (m, 3H, cyc.Hexyl), 1.57 (s, 9H, t-Bu), 1.84-1.90 (m, 7H, cyc.Hexyl part), 3.09 (m, 1H, CH of cyc.Hexyl-benzylic), 3.84 (s, 3H, OCH$_3$), 6.55 (d, J=4 Hz, 1H, aryl H$_2$'), 7.06 (d, 1H, aryl H$_3$'), 7.08 (s, 1H, aryl H$_6$'), 7.23 (d, 1H, Indole-H$_5$), 7.53 (d, J=8 Hz, 1H, Indole-H$_4$), 7.70-7.75 (m, 2H, NH+Indole-H$_7$), 8.06 (s, 1H, CHO).

Intermediate 18

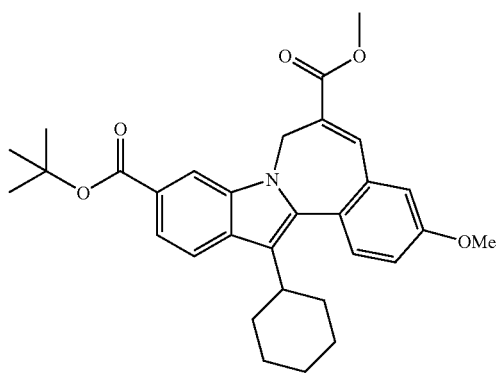

7H-Indolo[2,1-a][2]benzazepine-6,10-dicarboxylic acid, 13-cyclohexyl-, 10-(1,1-dimethylethyl) 6-methyl ester. tert-Butyl 3-cyclohexyl-2-(2-formyl-4-methoxyphenyl)-1H-indole-6-carboxylate (62.5 g, 0. 144 m) was dissolved in dry DMF (1.2 L) and stirred mechanically. Cesium carbonate (84 g, 0. 17 m) and methyl 2-(dimethoxyphosphoryl)acrylate (65-70% GC pure, 56.2 g, 0.18 m) were then added and the reaction mixture was heated to 65° C. for 4 h, and the reaction was monitored by TLC (Hexane-Ethyl acetate 80:20, Rf (Product)=0.7). On completion, the mixture was cooled to rt, then quenched with water (1.0 L). A yellow solid precipitated, which was collected by filtration and air dried. This material was then slurried in methanol, filtered, and dried under vacuum to give the product as a yellow powder, (70 g, 90%). HPLC: 99.1% (RT=6.45 min), Column: C18 BDS (4.6×50 mm), Mobile Phase: Gradient of 0.1% TFA in water: ACN (30→100→30), Flow rate 0.8 mL/min. LCMS: 100% (RT=7.00 min), Column : Geneis, C18 (50×4.6 mm), Mobile Phase: Gradient of 0.1% Formic acid in water: ACN (70→95→70), Flow rate: 0.8 mL/min; M+1=502.2; $^1$H NMR (CDCl$_3$) (400 MHz) δ 1.10-1.30 (m, 3H, cyc.Hexyl), 1.64 (s, 9H, t-Bu), 1.77-2.07 (m, 7H, cyc.Hexyl part), 2.80 (m, 1H, CH of cyc.Hexyl-benzylic), 3.84 (s, 3H, OCH$_3$), 3.93 (s, 3H, COOCH$_3$), 4.15 & 5.65 (two br. peak., 1H each, allylic CH$_2$), 6.95 (s, 1H, aryl H$_6$'), 7.01 (d, 1H, aryl H$_2$'), 7.53 (d, J=8 Hz, 1H, aryl H$_3$'), 7.70 (d, J=4 Hz, 1H, Indole-H$_5$), 7.84 (s+d, 2H, olefinic H+Indole-H$_4$), 8.24 (s, 1H, indole-H$_7$); $^{13}$C NMR (CDCl$_3$) (100.0 MHz) δ 166.92, 165.71, 158.96, 142.28, 136.47, 13.50, 134.61, 132.43, 132.01, 129.73, 124.78, 124.68, 120.33, 119.39, 119.04, 115.62, 115.05, 111.27, 80.27, 55.49, 52.50, 39.09, 36.81, 33.40, 28.38, 27.15, 26.28.

Intermediate 19

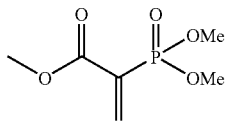

2-Propenoic acid, 2-(dimethoxyphosphinyl)-, methyl ester. To a 5 L four necked round bottom flask equipped with a mechanical stirrer, a condenser, a temperature controller and a N2 inlet, was charged paraformaldehyde (40.5 g, 1.35 mol), MeOH (2 L) and piperidine (2 mL). The reaction mixture was heated to reflux under N2 for 3 h. After cooling to 50° C., 2-(dimethoxyphosphoryl)acetate (150 g, 0.824 mol) was added in one portion. The reaction mixture was continued to reflux for 18 h. After cooling to rt, the reaction solution was concentrated in vacuo to give a clear colorless oil. The above oil was dissolved in dry toluene (1 L) in a 3 L four necked round bottom flask equipped a temperature controller, a $N_2$ inlet, a magnetic stirrer and a Dean-Stark apparatus. To the solution was added $TsOH.H_2O$ (5.2). The reaction mixture was then refluxed azeotropically to remove methanol for 18 h. After cooling to rt, the solution was concentrated in vacuo to give a yellow oil which was vacuum distilled at 150-155° C./0.2 mmHg to afford the product as a colorless oil (135.0). Purity, 90% based on 1H NMR. $^1$H NMR (CDCl3, 300 MHz) δ 7.0 (dd, J=42.4 and 1.5 Hz, 1H), 6.73 (dd, J=20.5 and 1.8 Hz, 1H), 3.80 (s, 6H), 3.76 (s, 3H).

Intermediate 20

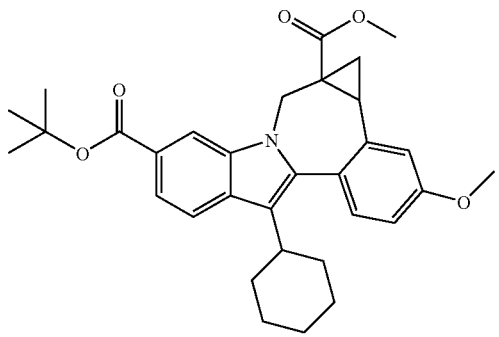

Cycloprop[d]indolo[2,1-a][2]benzazepine-1a,5(2H)-dicarboxylic acid, 8-cyclohexyl-1,12b-dihydro-11-methoxy-, 5-(9,11-dimethylethyl)1a-methyl ester, (−/+). Sodium hydride (96 mg, 4 mmol) was added to a stirred suspension of trimethylsulfoxonium chloride (567 mg, 4.4 mmol) in anhydrous DMSO (10 mL) under nitrogen. The resultant mixture was stirred at rt for 30-45 min and then neat 7H-indolo[2,1-a][2]benzazepine-6,10-dicarboxylic acid, 13-cyclohexyl-3-methoxy-, 10-(1,1-dimethylethyl) 6-methyl ester (1.0, 2 mmol) was added in small portions. The suspension was diluted with DMSO (5 mL) and heated at 50° C. for 3-4 h. The reaction mixture was allowed to cool to rt and water was added. A solid separated, which was collected by filtration and washed with water and then air dried overnight to afford 1.15 of crude product. This material was purified by flash column chromatography (silica gel, 3% MeOH in DCM) to provide pure title compound (0.96): LC/MS: Retention time 3.816 min; m/e 516 (MH$^+$). $^1$H NMR (400 MHz, CDCl$_3$): The product was observed to exist as inter-converting rotamers, as evidenced from the compound's NMR spectrum.

The following procedure is an example of a method to effect the resolution of racemic cycloprop[d]indolo[2,1-a][2]benzazepine-1a,5(2H)-dicarboxylic acid, 8-cyclohexyl-1, 12b-dihydro-11-methoxy-, 5-(1,1-dimethylethyl)1a-methyl ester, (+/−). A sample of cycloprop[d]indolo[2,1-a][2]benzazepine-1a,5(2H)-dicarboxylic acid, 8-cyclohexyl-1,12b-dihydro-11-methoxy-, 5-(1,1-dimethylethyl)1a-methyl ester, (+/−)- was dissolved in a mixture of isopropanol and acetonitrile (8:2) to give a final concentration of 20 mg/mL. This mixture was injected on a preparative chiral SFC chromatography system using the following conditions: Chiralcel OJ-H column, 4.6×250 mm, 5 μm; Mobile Phase: 8% MeOH in $CO_2$; Temp: 35° C.; Flow rate: 2 mL/min for 16 min; UV monitored@260 nm; Injection: 5 μL of ~20.0 mg/mL in IPA: ACN (8:2).

Intermediate 21

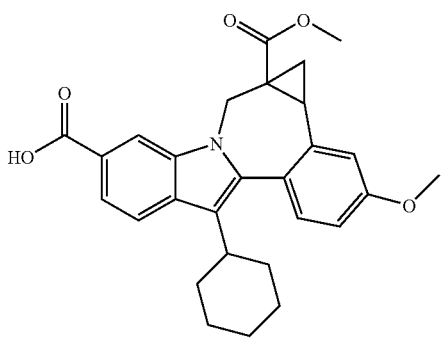

Cycloprop[d]indolo[2,1-a][2]benzazepine-1a,5(2H)-dicarboxylic acid, 8-cyclohexyl-1,12b-dihydro-11-methoxy-1a-methyl ester, (+/−)-. TFA (5 mL) was added to a solution of (+/−) 8-Cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester (515 mg, 1 mmol) in anhydrous DCM (10 mL). The resultant solution was stirred at rt for approximately 8 to 12 hr. The reaction was then evaporated to dryness to afford the title compound (0.47 g, 100%). LC/MS: Retention time 2.245 min; m/e 460 (MH$^+$). $^1$H NMR (400 MHz, CDCl$_3$): From the compounds NMR spectrum, the product was observed to exist as a mixture of interconverting rotamers.

Intermediate 22

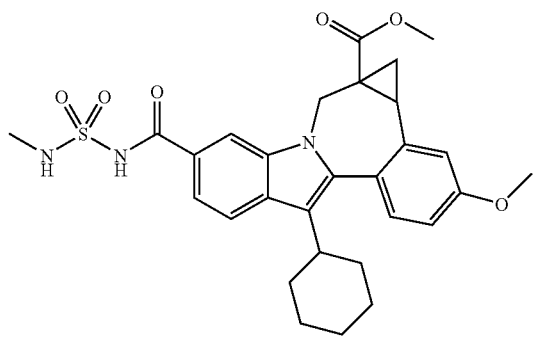

Cycloprop[d]indolo[2,1-a][2]benzazepine-1a(2H)-carboxylic acid, 8-cyclohexyl-1,12b-dihydro-11-methoxy-5-[[[(methylamino)sulfonyl]amino]carbonyl]-, methyl ester. A solution of 8-Cyclohexyl-1,1a,2,12b-tetrahydro-11-methoxy-1a-(methoxycarbonyl)-cycloprop[d]indolo[2,1-a][2]benzazepine-5-carboxylic acid (140 mg, 0.31 mmol) and CDI (64 mg, 0.40 mmol) in THF (3 mL) was stirred for 1 hr at 60° C. N-methylsulfamide (68 mg, 0.62 mmol) and DBU (71.6 mg, 0.47 mmol) were added and the mixture was stirred at 60° C. overnight. The reaction was then poured into cold water, acidified with dilute hydrochloric acid and extracted into ethyl acetate. The extracts were washed sequentially with dilute hydrochloric acid (0.1 N), and brine, and then dried (anhy. sodium sulfate), filtered and evaporated to provide the title compound as a brown solid. ESI-MS m/e 552 (MH⁺). This material was used without further purification.

Intermediate 23

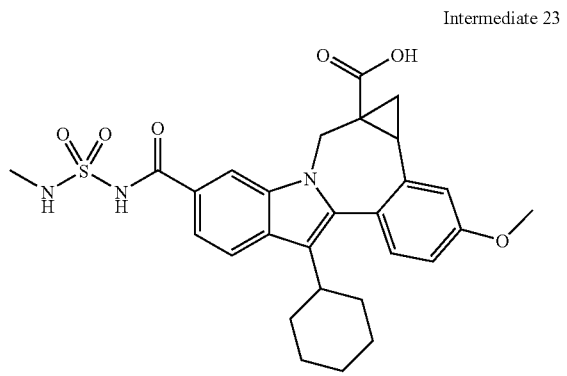

Cycloprop[d]indolo[2,1-a][2]benzazepine-1a(2H)-carboxylic acid, 8-cyclohexyl-1,12b-dihydro-11-methoxy-5-[[[(methylamino)sulfonyl]amino]carbonyl]-. Cycloprop[d]indolo[2,1-a][2]benzazepine-1a(2H)-carboxylic acid, 8-cyclohexyl-5-[[[(methylamino)sulfonyl]amino]carbonyl]-1,12b-dihydro-11-methoxy-, methyl ester was dissolved in THF, MeOH mixture (2 mL, 2 mL). 2.5 M NaOH (aq.) (1.2 mL, 3 mmol) was then added and the reaction was shaken at 22° C. for 2 hr. The solution was then neutralized with 1M HCl (aq.) (3 mL) and concentrated to remove the organic solvents. The residue was slurried with H₂O and the solids were collected by filtration, washed with H₂O and dried to yield compound the title compound (160 mg, 0.30 mmol). ESI-MS m/e 538 (MH⁺). This material was used without further purification.

Intermediate 24

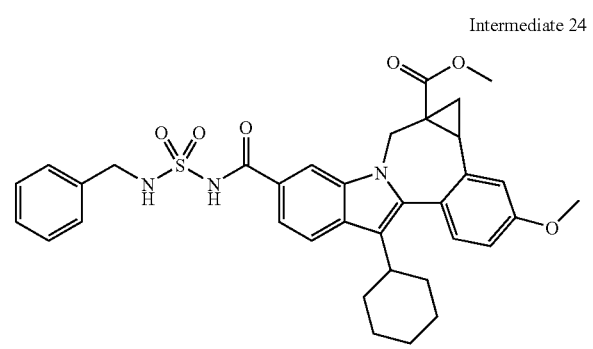

Cycloprop[d]indolo[2,1-a][2]benzazepine-1a(2H)-carboxylic acid, 8-cyclohexyl-5-[[[(benzylamino)sulfonyl]amino]carbonyl]-1,12b-dihydro-11-(methoxy)-12-(methoxy)-, methyl ester, (+/−)-. A solution of (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid (200 mg, 0.44 mmol) and CDI (92 mg, 0.57 mmol) in THF (5 mL) was stirred for 1 hr at 60° C. N-benzylsulfamide (164 mg, 0.88 mmol) and DBU (100 mg, 0.66 mmol) were then added and the resultant mixture was stirred at 60° C. overnight. The reaction was then poured into cold water, acidified with dilute hydrochloric acid and extracted into ethyl acetate. The organic phase was washed hydrochloric acid (0.1 N), brine and dried (sodium sulfate) and evaporated in vacuo to provide the title compound as a brown solid. ESI-MS m/e 628 (MH⁺).

Intermediate 25

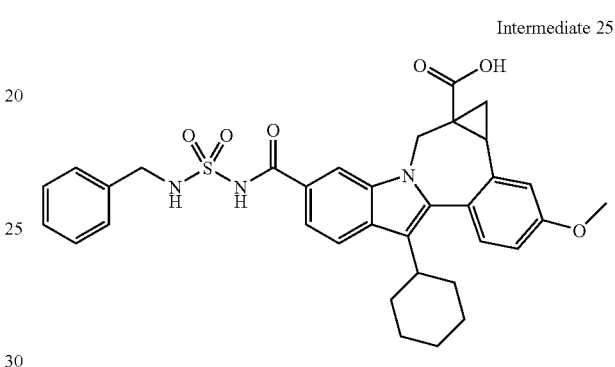

Cycloprop[d]indolo[2,1-a][2]benzazepine-1a(2H)-carboxylic acid, 8-cyclohexyl-1,12b-dihydro-11-methoxy-5-[[[[(phenylmethyl)amino]sulfonyl]amino]carbonyl]-, (+/−)-. The title compound was prepared using a similar procedure to that described for cycloprop[d]indolo[2,1-a][2]benzazepine-1a(2H)-carboxylic acid, 8-cyclohexyl-5-[[[(methylamino)sulfonyl]amino]carbonyl]-1,12b-dihydro-11-methoxy-cycloprop[d]indolo[2,1-a][2]benzazepine-1a(2H)-carboxylic acid starting from (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid. ESI-MS m/e 613 (MH⁺), 1H NMR (500 MHz, MeOD) δ ppm 1.22-2.20 (m, 13 H) 3.27-3.31 (m, 1 H) 3.47 (d, J=14.95 Hz, 0.6 H) 3.92 (d, J=2.44 Hz, 3 H) 4.04 (d, 0.4 H) 4.31 (d, J=2.75 Hz, 2 H) 5.24 (d, 0.4 H) 5.48 (d, 0.6 H) 7.02 (d, 1 H) 7.17 (d, J=2.75 Hz, 1 H) 7.19-7.35 (m, 5 H) 7.39 (t, J=7.48 Hz, 2 H) 7.45-7.52 (m, 1 H) 7.80 (d, J=1.53 Hz, 0.4 H) 7.85 (dd, J=8.39, 6.87 Hz, 1 H) 8.22 (d, J=1.53 Hz, 0.6 H).

Intermediate 26

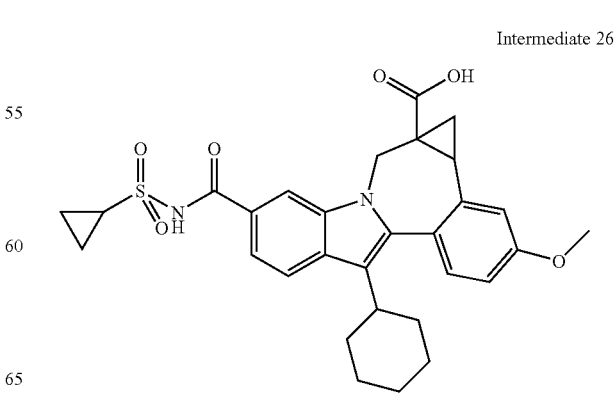

Cycloprop[d]indolo[2,1-a][2]benzazepine-1a(2H)-carboxylic acid, 8-cyclohexyl-5-[[(cyclopropylsulfonyl)amino]carbonyl]-1,12b-dihydro-11-methoxy-, (+/−)-. A mixture of (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid (1 equiv), and carbonyldiimidazole (1.5 equiv) in anhydrous THF was heated at 50° C. for 30 min and allowed to cool to rt. Then 1 equiv of cyclopropanesulfonamide and 1,8-diazabicyclo[5.4.0]undec-7-ene (2 equiv) were added consecutively. The resultant mixture was stirred at rt overnight. After acidic aqueous workup, the isolated crude product was purified by prep. HPLC. The intermediate ester was then hydrolyzed using 1N NaOH in THF-MeOH to afford the title compound. LC/MS: Retention time: 2.030 min; m/e 549 (MH+). H NMR (400 MHz, CDCl3): The product was observed to exist as inter-converting rotamers, as evidenced from the compound's NMR spectrum.

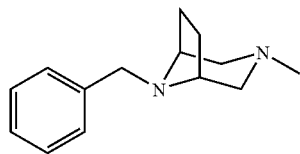

Intermediate 27

3,8-Diazabicyclo[3.2.1]octane, 3-methyl-8-(phenylmethyl)-. Cis-1-Benzyl-2,5-bis(chloromethyl)pyrrolidine hydrochloride (37.5 g, 0.13 mol) (Prepared as described in Published PCT patent application WO200232902) was suspended in CH₃CN (900 mL) in a 3-neck 5 L round bottom flask fitted with mechanical stirrer, reflux condenser, and thermometer. The stirred suspension was warmed to 50° C., NaHCO₃ (97 g, 1.1 mol) was added, and the suspension was warmed to 70° C. NaI (50 g, 0.33 mol) was added and stirred at 70° C. for 5 min, at which point an addition funnel was affixed atop the condenser. To the addition funnel was added 48 mL of 40% aqueous MeNH₂ (0.55 mol) in 850 mL of CH₃CN, and this solution was added dropwise (rate of addition maintained between 10-15 ml/min). The addition was complete after 75 min, at which point the reaction was cooled to rt., the solids filtered off, and the solvent concentrated to ~800 mL. The reaction was poured into EtOAc (800 mL) and washed with 1 N NaOH (2×100 mL). The aqueous phase was re-extracted with EtOAc (2×100 mL), the combined organic phases were dried over Na₂SO₄ and concentrated. The resulting residue was introduced on to silica gel (620 g) and eluted with 2.8% MeOH/0.4% conc. NH₄OH in CHCl₃ (6 L total). Pure fractions were collected from 2 L to 4 L. Concentration yielded 8.76 (32% yield) of the title compound as a brown oil. 1H NMR (400 MHz, CDCl3) δ ppm 1.79-1.87 (m, 2 H) 1.92-1.99 (m, 2 H) 2.23 (s, 3 H) 2.27-2.37 (m, 2 H) 2.54-2.63 (m, 2 H) 3.10 (s, 2 H) 3.52 (s, 2 H) 7.20-7.26 (m, 1 H) 7.30 (t, J=7.30 Hz, 2 H) 7.36-7.42 (m, 2 H). LC method: Solvent A=10% MeOH/90% H2O/0.1% TFA, Solvent B=90% MeOH/10% H2O/0.1% TFA, Start %B=0%, Final %B =100, Flow Rate=4 ml/min, Gradient time=2 min, Run time=3 min, Column: Phenomenex-Luna 10 □m C18 50 mm×3.0 mm, Rt=0.23 min; MS: (ES+) m/z (M+H)+=217.3. An additional 6.1 g of mixed fractions were obtained from the column (>80% pure by 1H NMR integration).

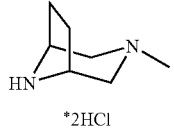

Intermediate 28

3,8-Diazabicyclo[3.2.1]octane, 3-methyl-, dihydrochloride. N-methyl-N-benzylbicyclodiamine, (14.22 g, 65.7 mMol) was dissolved in 650 ml of methanol and 17 ml of 12M aqueous hydrochloric acid was added. The solution was placed in a 2 L Parr bottle under nitrogen and 3.66 of 20% palladium hydroxide on carbon added to the reaction. The mixture was placed on a Parr shaker under 60 psig of hydrogen for 17 hours. The reaction was judged complete by TLC analysis (Silica Gel plate eluted with a 10 parts by volume solution of 2M ammonia in methanol dissolved in 90 parts by volume of chloroform). The reaction was filtered through a plug of ceilite, which was then rinsed sequentially with water and methanol. The combined filtrates were concentrated in vacuuo and methanol and benzene added until a homogenous solution was obtained. 75 mL of 2.0M hydrochloric acid in diethyl ether was then added. Volatiles were removed from the product solution in vacuuo. A pale yellow solid was eventually obtained by repeated azetroping of water from the product solution using a methanol/benzene mixture. The solid product, 3-methyl-3,8-diazabicyclo[3.2.1]octane was dried in vacuuo overnight to obtain 11.98 (91%) of a hygroscopic solid. The product was removed from the flask and bottled in a glove bag under nitrogen due to its hygroscopic nature. ¹H NMR (500 MHz, DMSO-D6) δ ppm 1.96-2.14 (m, 2 H) 2.34 (d, J=8.24 Hz, 2 H) 2.66 (s, 3 H) 3.46 (d, J=11.90 Hz, 2 H) 3.58 (s, 3 H, contains H2O) 4.17 (s, 2 H) 9.92 (s, 1 H) 10.21 (s, 1 H) 11.30 Hz, 1H); ¹³C NMR (126 MHz, DMSO-D6) δ ppm 24.04 (s, 1 C) 43.49 (s, 1 C) 52.50 (s, 1 C) 54.47 (s, 1 C).

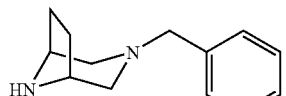

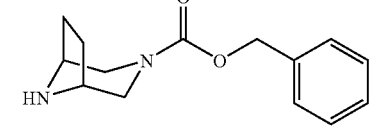

Intermediates 29 and 30

3,8-diazabicyclo[3.2.1]octane-3-carboxylic acid, phenylmethyl ester and 3-(phenylmethyl)-3,8-diazabicyclo[3.2.1]octane. Triethylamine (1.44 mL, 10.363 mmol) was added to a solution of 8-boc-3,8-diaza-bicyclo[3.2.1]ocatane (2.0 g, 9.421 mmol) in CH₂Cl₂ (20 mL), Benzyl chloroformate (1.46 mL, 10.363 mmol) was added dropwise at 0° C. and the reaction mixture was stirred at 0° C. for 0.5 hr, then allowed to warm to rt. and stirring was continued for 3 days. The reaction mixture was then quenched with water and acidified with 1N HCl solution. The organic layer was separated, washed with brine, dried (MgSO₄) and concentrated to give a colorless thick oil as the crude product. 70 mg of this material was then dissolved in 1,2-dichloroethane (2 mL) and TFA (0.5 mL) was added. The reaction mixture was stirred at rt. for 2 hr. The solvent and TFA were then evaporated to give a mixture of the two title compounds as a colorless thick oil.

Intermediate 31

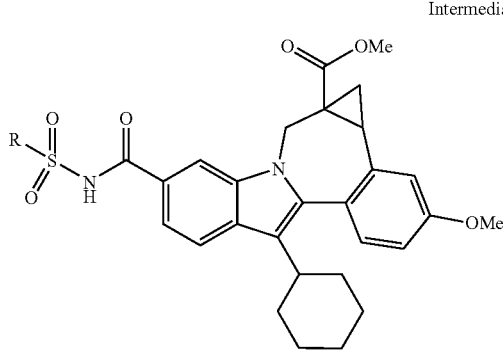

General procedure for making sulfonamides. A mixture of acid (1 equiv) and carbonyldiimidazole (1.5 equiv) in an. THF was heated at 50° C. for 30 min and allowed to cool to rt. Then 1 equiv of either sulfamide (R=NR$_2$) or sulfonamide (R=alkyl or aryl) and DBU (2 equiv) were added consecutively. The resultant mixture was stirred at rt overnight. After acidic aqueous workup, isolated crude product was purified by prep. HPLC to afford the title intermediates.

Intermediate 32

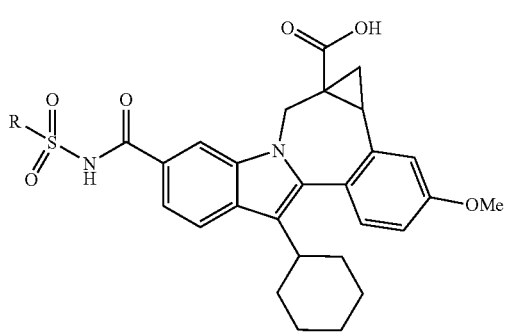

General procedure for making acids. Methyl esters hydrolyzed using 1N NaOH in THF-MeOH.

Intermediate 33

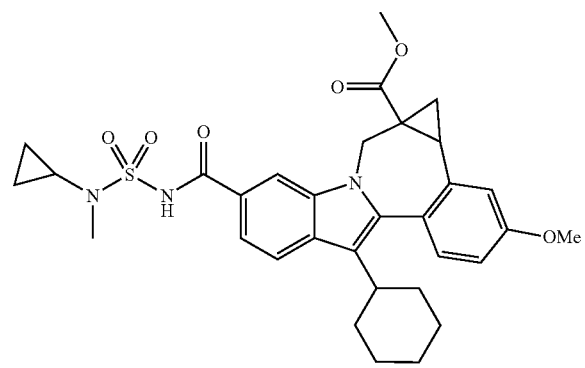

Neat CDI (0.049 g, 0.302 mmol) was added to stirred solution of the acid (0.092 g, 0.200 mmol) in THF (1 ml) and the mixture was heated at 50° C. for 30 min and then allowed to cool to rt. Then N-cyclopropyl-N-methylsulfamide (0.0451 g, 0.300 mmol) and DBU (0.060 ml, 0.400 mmol) were added consecutively. The mixture sonicated for 1-2 hand then stirred overnight at rt. Reaction was quenched with MeOH (0.5 ml) and then acidified with 1N HCl and extracted with EtOAc (2×25 mL), washed with water, brine and dried (Na2SO4). Crude product (0.123 g) was purified by silica gel flash chromatography (5% MeOH in DCM) to afford the expected product The product as a off-white solid (0.101 g 85%).

Intermediate 34

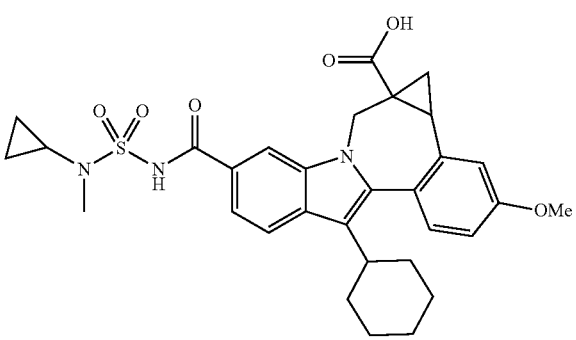

1N NaOH (2 mL, 2.000 mmol) was added to stirred solution of the methyl ester (0.098 g, 0.166 mmol) in THF-MeOH under nitrogen. The mixture was stirred at rt for 2 h and then acidified with 1N HCl (3 ml), extracted with EtOAc (2×25 ml), washed with water, brine and dried (MgSO$_4$). Evaporation of solvents gave the acid as an off-white solid (0.0942 g, 98%). LC/MS: m/e 578 (MH+). LC/MS method: Start % B: 0, Final % B: 100; Gradient time: 3 min; Stop time: 4 min; Flow rate: 4 ml/min; Wavelenth: 220; Solvent A: 10% MeOH/90% H$_2$O/0.1% Trifluoroacetic Acid; Solvent B: 10% H$_2$O/90% MeOH/0.1% Trifluoroacetic Acid; Column: XBridge 4.6×50 mm S5.

Intermediate 35

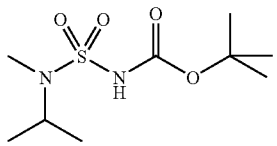

t-Butanol (1.35 mL, 14 mmol) was added dropwise to the solution of CSI (1.24 mL, 14 mmol) of CH$_2$Cl$_2$ (10 mL) at 0° C. The generated solution was stirred for 2 h at 0° C. A solution of N-methylpropan-2-amine (1.57 ml, 14.13 mmol) and TEA (2.167 ml, 15.54 mmol) in CH$_2$Cl$_2$ (3 ml) was added dropwise. The generated reaction mixture was stirred for 2 h at r.t. The reaction mixture was diluted with EtOAc and washed with cold 1N HCl, brine, dried (MgSO4), removed the solvent and the residue was purified by Biotage 40M column (EtOAc-MeOH (90-10)/hexane 5% to 100%) to afford the product as a colorless gel (2.3 g, 65%) 1H NMR (400 MHz, CHLOROFORM-d) δ ppm 1.19 (d, J=6.55 Hz, 6 H) 1.49 (s, 9 H) 2.90 (s, 3 H) 4.05-4.26 (m, 1 H) 7.02 (br. s., 1 H).

Intermediate 36

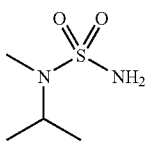

To tert-butyl N-isopropyl-N-methylsulfamoylcarbamate (2.3 g, 9.12 mmol) was added cold HCl (6 mL, 24.00 mmol) and stirred at room temperature for 2 h, removed the solvent to afford the product as a solid in light tan (1.38 g, 99%). 1H NMR (400 MHz, CHLOROFORM-d) δ ppm 1.16 (d, J=6.80 Hz, 5 H) 2.72 (s, 3 H) 4.16 (dt, J=13.53, 6.70 Hz, 1 H) 4.43 (br. s., 1 H).

Intermediate 37

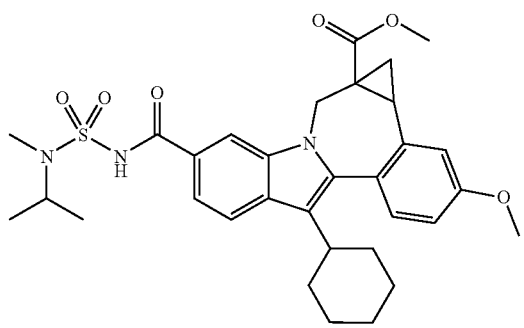

The product (0.261 g, 81%) was made from the acid (0.25 g, 0.54mmol) and amine using CDI and DBU. LC-MS retention time: 3.635 min; MS m/z (M+H) 594. H NMR showed compound existed as rotamers (~4/3). LC/MS method: Start % B: 0, Final % B: 100; Gradient time: 3 min; Stop time: 4 min; Flow rate: 4 ml/min; Wavelenth: 220; Solvent A: 10% MeOH/90% H$_2$O/0.1% Trifluoroacetic Acid; Solvent B: 10% H$_2$O/90% MeOH/0.1% Trifluoroacetic Acid; Column: XBridge 4.6×50 mm S5.

Intermediate 38

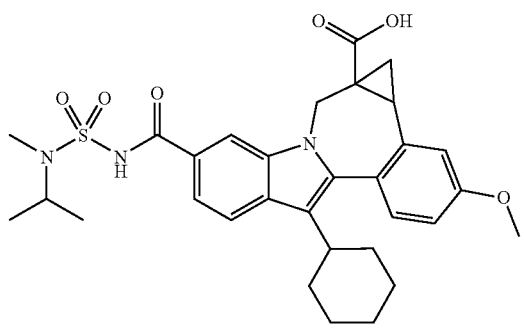

The acid (0.22 g, 87%) was made from the ester (0.258 g, 0.435 mmol) using NaOH in THF/MeOH. The acid was isolated as a pale yellow solid. LC-MS retention time: 3.608 min; MS m/z (M+H) 580. LC/MS method: Start % B: 0, Final % B: 100; Gradient time: 3 min; Stop time: 4 min; Flow rate: 4 ml/min; Wavelenth: 220; Solvent A: 10% MeOH/90% H$_2$O/0.1% Trifluoroacetic Acid; Solvent B: 10% H$_2$O/90% MeOH/0.1% Trifluoroacetic Acid; Column: XBridge 4.6×50 mm S5. 1H NMR existed rotamers (~1/2). The major isomer: 1H NMR (400 MHz, CHLOROFORM-d) δ ppm 0.41 (t, J=6.30 Hz, 1 H) 1.08-2.15 (m, 17 H) 2.63-2.80 (m, 1 H) 2.84-2.96 (m, 1 H) 3.04 (s, 3 H) 3.84 (s, 3 H) 4.03 (d, J=14.86 Hz, 1 H) 4.22-4.41 (m, 1 H) 5.35 (d, J=15.11 Hz, 1 H) 6.86 (dd, J=8.44, 2.39 Hz, 1 H) 6.98 (d, J=2.27 Hz, 1 H) 7.20 (d, J=8.56 Hz, 1 H) 7.67 (d, J=8.31 Hz, 1 H) 7.81-7.89 (m, 1 H) 8.10 (s, 1 H).

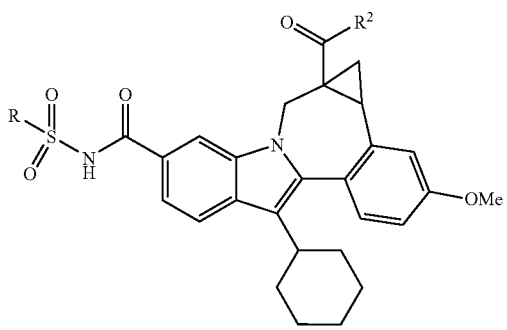

General procedure for making amides for some examples. Acid derivatives (1 equiv) were combined with corresponding amine (1.2 equiv), triethylamine (2-3 equiv) and TBTU (1.3 equiv) in anh. DMF and stirred at rt for 1-2 h until completion of the amide coupling. Isolated crude products were purified by prep. HPLC to provide the desired amides.

EXAMPLE 1

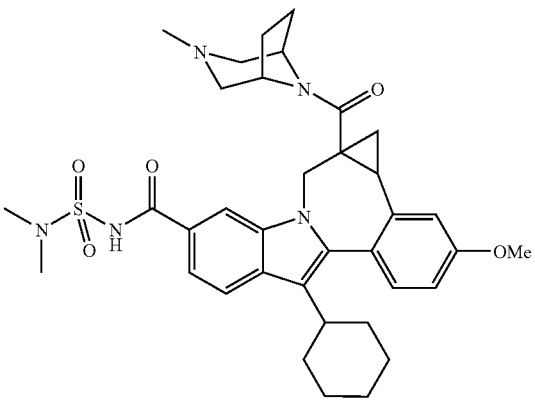

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[(3-methyl-3,8-diazabicyclo[3.2.1]oct-8-yl)carbonyl]-, (+/−)-. TBTU (43.7 mg, 0.136 mmol) and DIPEA (0.095 mL, 0.544 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (50 mg, 0.0906 mmol) in DMSO (2.0 mL). The reaction mixture was stirred at rt for 15 min. 3-Methyl-3,8-diaza-bicyclo[3.2.1]octane dihydrochloride {J & W PharmLab, LLC Morrisville, Pa. 19067-3620}. (27.1 mg, 0.136 mmol) was then added and the reaction mixture was stirred at rt for 3 hr. It was then concentrated and the residue was purified by preparative reverse phase HPLC to give the final product as a yellow solid, (32 mg, 46% yield). MS m/z 660(MH$^+$), Retention time: 2.445 min 1H NMR (300 MHz, MeOD) δ ppm 0.20 (m, 0.23 H) 1.11-2.25 (m, 15.77 H) 2.58 (m, 0.23 H) 2.69 (m, 0.77 H) 2.75-3.11 (m, 10 H) 3.28-3.75 (m, 5 H) 3.91 (s, 2.31 H) 3.92 (s, 0.69 H) 4.15-4.37 (m, 1 H) 4.68 (m ,br, 1 H) 4.94-5.00 (m, 0.23 H) 5.16 (d, J=15.00 Hz, 0.77 H) 7.00-7.09 (m, 1 H) 7.18 (d, J=2.56 Hz, 0.23 H) 7.21 (d, J=2.56 Hz, 0.77 H) 7.33 (d, J=8.41 Hz, 0.77 H) 7.35 (d, J=8.42 Hz, 0.23 H) 7.57 (dd, J=8.42, 1.46 Hz, 0.77 H) 7.62 (dd, J=8.78, 1.46 Hz, 0.23 H) 7.91 (d, J=8.42 Hz, 0.77 H) 7.93 (d, J=8.42 Hz, 0.23 H) 8.00 (s, 0.77 H) 8.07 (s, 0.23 H).

EXAMPLE 2

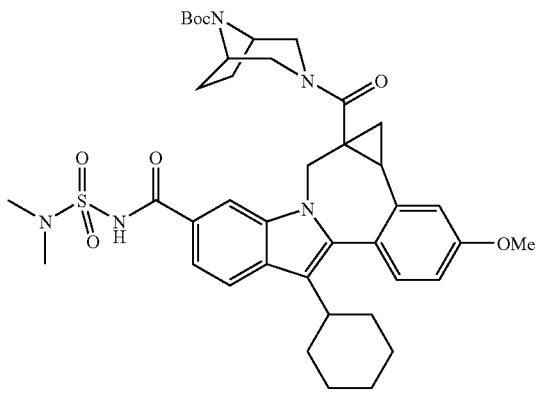

3,8-Diazabicyclo[3.2.1]octane-8-carboxylic acid, 3-[[8-cyclohexyl-5-[[[(dimethylamino)sulfonyl]amino]carbonyl]-1,12b-dihydro-11-methoxycycloprop[d]indolo[2,1-a][2]benzazepin-1a(2H)-yl]carbonyl]-1,1-dimethylethyl ester, (+/−)-. TBTU (131 mg, 0.408 mmol) and DIPEA (0.237 mL, 1.36 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (150 mg, 0.272 mmol) in DMSO (4.0 mL). The reaction mixture was stirred at rt for 15 min. 8-Boc-3,8-diaza-bicyclo[3.2.1]octane (86.7 mg, 0.408 mmol) was then added and the reaction mixture was stirred at rt overnight. It was then concentrated and the residue was purified by preparative reverse phase HPLC to give the title product as a light yellow solid, (110 mg, 54% yield). MS m/z 746(MH⁺), Retention time: 3.040 min. 1H NMR (300 MHz, MeOD) δ ppm 0.17 (m, 0.25 H) 1.08 (m, 0.25 H) 1.17-2.28 (m, 24.5 H) 2.38-3.12 (m, 8 H) 3.43-4.43 (m, 10 H) 4.76-4.85 (m, 0.25 H) 4.96-5.19 (m, 0.75 H) 7.02 (dd, J=8.60, 2.38 Hz, 1 H) 7.17 (d, J=2.19 Hz, 0.25 H) 7.20 (d, J=2.20 Hz, 0.75 H) 7.26-7.39 (m, 1 H) 7.49-7.70 (m, 1 H) 7.80-8.00 (m, 1.75 H) 8.12 (s, 0.25 H).

EXAMPLE 3

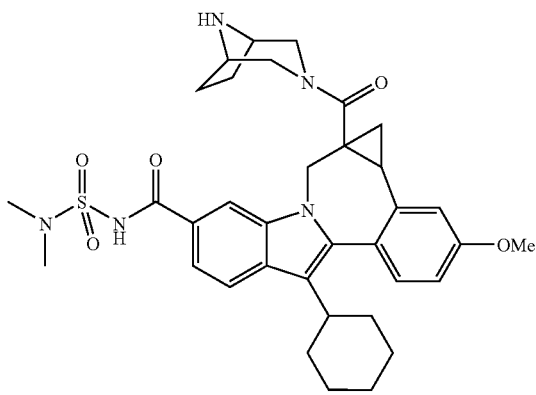

Cycloprop[d]indolo[2,1-a][2]benzazepine-5-carboxamide, 8-cyclohexyl-1a-(3,8-diazabicyclo[3.2.1]oct-3-ylcarbonyl)-N-[(dimethylamino)sulfonyl]-1,11a,2,12b-tetrahydro-11-methoxy-, (+/−)-. TFA (2 mL) was added to a solution of (+/−) 3,8-diazabicyclo[3.2.1]octane-8-carboxylic acid, 3-[[8-cyclohexyl-5-[[[(dimethylamino)sulfonyl]amino]carbonyl]-1,12b-dihydro-11-methoxycycloprop[d]indolo[2,1-a][2]benzazepin-1a(2H)-yl]carbonyl]-, 1,1-dimethylethyl ester (98 mg, 0.131 mmol) in 1,2-dichloroethane (3 mL). The reaction mixture was stirred at rt. for 2 hr. It was then concentrated to give the desired product as a brownish colored solid, (100 mg, 100% yield). MS m/646(MH⁺), Retention time: 2.478 min. 1H NMR (500 MHz, MeOD) δ ppm 0.24 (m, 0.28 H) 1.14 (m, 0.28 H) 1.19-2.23 (m, 15.22 H) 2.57 (m, 0.28 H) 2.69 (m, 0.72 H) 2.81-3.09 (m, 8 H) 3.30-3.40 (m, 1 H) 3.67 (d, J=15.87 Hz, 0.72 H) 3.91 (s, 2.16 H) 3.93 (s, 0.84 H) 3.90-4.27 (m, 4.28 H) 4.88-4.91 (m, 0.28 H) 5.11 (d, J=15.56 Hz, 0.72 H) 7.00-7.09 (m, 1 H) 7.19 (d, J=2.75 Hz, 0.28 H) 7.21 (d, J=2.14 Hz, 0.72 H) 7.34 (d, J=8.54 Hz, 0.72 H) 7.37 (d, J=8.55 Hz, 0.28 H) 7.59 (dd, J=8.55, 1.53 Hz, 0.72 H) 7.63 (dd, J=8.39, 1.37 Hz, 0.28 H) 7.92 (d, J=8.55 Hz, 0.72 H) 7.94-7.99 (m, 1 H) 8.10 (s, 0.281 H).

EXAMPLE 4

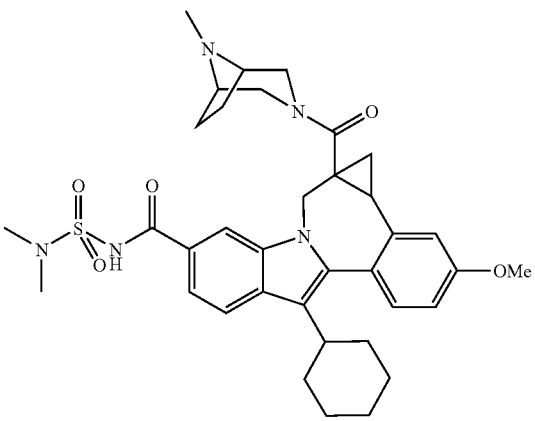

Cycloprop[d]indolo[2,1-a][2]benzazepine-5-carboxamide, 8-cyclohexyl-N-[(dimethylamino)sulfonyl]-1,11a,2,12b-tetrahydro-11-methoxy-1a-[(8-methyl-3,8-diazabicyclo[3.2.1]oct-3-yl)carbonyl]-, (+/−)-. To a solution of (+/−) cycloprop[d]indolo[2,1-a][2]benzazepine-5-carboxamide, 8-cyclohexyl-1a-(3,8-diazabicyclo[3.2.1]oct-3-ylcarbonyl)-N-[(dimethylamino)sulfonyl]-1,1a,2,12b-tetrahydro-11-methoxy- (54 mg, 0.071 mmol) in methanol (3 mL), paraformaldehyde (6.4 mg, 0.213 mmol), ZnCl₂ (29 mg, 0.213 mmol) and Na(CN)BH₃ (13.4 mg, 0.213 mmol) were added. The resultant mixture was heated at 60° C. for 2 hr, and then cooled to rt. The solid present was removed by filtration, and the filtrate was concentrated under vacuum and the residue purified by preparative reverse phase HPLC to give the title compound as a light yellow colored solid, (37 mg, 67% yield). MS m/660(MH⁻), Retention time: 2.495 min. 1H NMR (500 MHz, MeOD) δ ppm 0.21 (m, 0.3 H) 1.13 (m, 0.3 H) 1.18-2.22 (m, 15.4 H) 2.58 (m, 0.3 H) 2.68 (m, 0.7 H) 2.76-3.11 (m, 11 H) 3.32-3.37 (m, 1 H) 3.63 (d, J=15.56 Hz, 0.7 H) 3.82-4.32 (m, 7.3 H) 4.88-4.92 (m, 0.3 H) 5.08 (d, J=15.56 Hz, 0.7 H) 7.00-7.08 (m, 1 H) 7.18 (d, J=2.14 Hz, 0.3 H) 7.21 (d, J=2.14 Hz, 0.7 H) 7.32 (d, J=8.55 Hz, 0.7 H) 7.35 (d, J=8.55 Hz, 0.3H) 7.57 (d, J=7.93 Hz, 0.7 H) 7.62 (dd, J=8.39, 1.37 Hz, 0.3 H) 7.91 (d, J=8.55 Hz, 0.7 H) 7.93-7.99 (m, 1 H) 8.09 (s, 0.3 H).

EXAMPLE 5

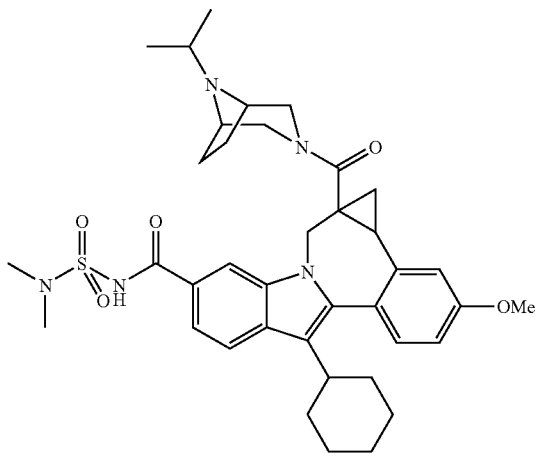

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[8-(1-methylethyl)-3,8-diazabicyclo[3.2.1]oct-3-yl]carbonyl]-, (+/−)-. To a solution of (+/−) cycloprop[d]indolo[2,1-a][2]benzazepine-5-carboxamide, 8-cyclohexyl-1a-(3,8-diazabicyclo[3.2.1]oct-3-ylcarbonyl)-N-[(dimethylamino)sulfonyl]-1,1a,2,12b-tetrahydro-11-methoxy- (40 mg, 0.071 mmol) in methanol (3 mL), acetone (1 mL), $ZnCl_2$ (29 mg, 0.213 mmol) and Na(CN)BH$_3$ (13.4 mg, 0.213 mmol) were added. The reaction mixture was heated at 60° C. overnight, and then cooled to rt. The solid present was removed by filtration, and the filtrate was concentrated under vacuum and the residue purified by preparative reverse phase HPLC to give the title compound as a light yellow colored solid. (29 mg, 69% yield). MS m/688(MH$^+$), Retention time: 2.477 min. 1H NMR (300 MHz, MeOD) δ ppm 0.20 (m, 0.23 H) 1.12 (m, 0.23 H) 1.18-2.41 (m, 21.54 H) 2.51-3.18 (m, 10 H) 3.64 (d, J=15.37 Hz, 0.77 H) 3.79-4.51 (m, 8.23 H) 4.81-4.88 (m, 0.23 H) 5.07 (d, J=14.27 Hz, 0.77 H) 6.99-7.08 (m, 1 H) 7.17-7.23 (m, 1 H) 7.28-7.36 (m, 1 H) 7.57 (dd, J=8.42, 1.10 Hz, 0.77 H) 7.61 (dd, J=8.42, 1.47 Hz, 0.23 H) 7.83-8.00 (m, 1.77 H) 8.09 (s, 0.23 H).

EXAMPLE 6

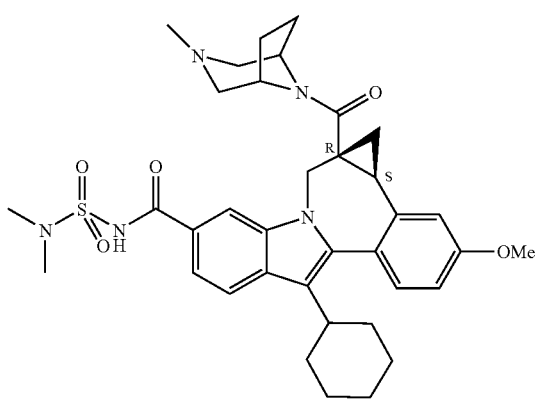

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[(3-methyl-3,8-diazabicyclo[3.2.1]oct-8-yl)carbonyl]-, (1aR,12bS)-. To a solution of (−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (204 mg, 0.37 mmol) in DMSO (8.0 mL), TBTU (178 mg, 0.555 mmol) and DIPEA (0.39 mL, 2.22 mmol) were added. The reaction mixture was stirred at rt for 15 min. Then 3-methyl-3,8-diaza-bicyclo[3.2.1]octane dihydrochloride (111 mg, 0.555 mmol) was added and the reaction mixture was stirred at rt for 2 hr. It was then concentrated and the residue was purified by preparative reverse phase HPLC to give a yellow solid as final TFA salt. (265 mg, 92% yield). Average Specific Rotation: −53.56° Solvent, MeOH.; Wavelength 589 nm; 50 cm cell. MS m/z 660(MH$^+$), Retention time: 3.035 min. $^1$H NMR (300 MHz, MeOD) δ ppm 0.20 (m, 0.23 H) 1.11-2.25 (m, 15.77 H) 2.58 (m, 0.23 H) 2.69 (m, 0.77 H) 2.75-3.11 (m, 10 H) 3.28-3.75 (m, 5 H) 3.91 (s, 2.31 H) 3.92 (s, 0.69 H) 4.15-4.37 (m, 1 H) 4.68 (m ,br, 1 H) 4.94-5.00 (m, 0.23 H) 5.16 (d, J=15.00 Hz, 0.77 H) 7.00-7.09 (m, 1 H) 7.18 (d, J=2.56 Hz, 0.23 H) 7.21 (d, J=2.56 Hz, 0.77 H) 7.33 (d, J=8.41 Hz, 0.77 H) 7.35 (d, J=8.42 Hz, 0.23 H) 7.57 (dd, J=8.42, 1.46 Hz, 0.77 H) 7.62 (dd, J=8.78, 1.46 Hz, 0.23 H) 7.91 (d, J=8.42 Hz, 0.77 H) 7.93 (d, J=8.42 Hz, 0.23 H) 8.00 (s, 0.77 H) 8.07 (s, 0.23 H).

An alternate procedure for the synthesis of cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[(3-methyl-3,8-diazabicyclo[3.2.1]oct-8-yl)carbonyl]-, (1aR,12bS)-rel-(−)- is provided below. To a mixture of (−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (25.2 g, 45.68 mmol) and 3-methyl-3,8-diazabicyclo-[3.2.1]octane dihydrochloride (10.0 g, 50.22 mmol) in anhydrous MeCN (300 mL) was added DIPEA (23.62 g, 182.72 mmol) under $N_2$. After 15 min, TBTU (16.12 g, 50.22 mmol) was added. The reaction solution was stirred for 30 min under $N_2$. The HPLC indicated the disappearance of starting material. The solvent in the solution was evaporated to give a foam. This was dissolved in EtOAc (2.5 L), washed with $H_2O$ (1.5 L), $H_2O$/brine (8:2) (1.5 L), brine (1.5 L), dried over $Na_2SO_4$ and evaporated to give 28.8 of crude product. This solid was pooled with 45.4 of material obtained from five separated reactions to afford a total of 74.2 of crude product. This was passed through a pad of silica gel (E. Merck 230-400 mesh, 1 kg), eluting with MeOH/$CH_2Cl_2$ (2.5:97.5). After evaporation, it gave a foam, which was treated with EtOAc and hexane to turn into a solid. After drying at 50° C. under vacuum for 7 h, the GC analysis indicated it has 1.4% each of EtOAc and hexane. After further drying at 61-64° C., the GC analysis indicated it still has 1.0% of hexane and 1.4% of EtOAc. The product was dissolved in $Et_2O$ and slowly evaporated in vacuum three times, dried at 60° C. under vacuum for 3 h to give 68.3 g. This was washed with $H_2O$ (900 mL) and redried at 68° C. under vacuum for 7 h to give 67.1 (77% yield) of the compound of example 6. The GC analysis indicated it has 0.97% of $Et_2O$. HPLC conditions column: Cadenza CD-C18 3×250 mm; UV: 257 and 220 nm; 25° C.; flow rate: 0.5 mL/min; gradient time: 38 min, 0-80% B (0-35 min) and 80% B (35-38 min); solvent A: 25 nM $CH_3COONH_4$ at pH 4.7 in water, solvent B: MeCN. HPLC purity 99.7% (Rt 26.54 min); Chiral HPLC conditions column: Regis (S,S) Whelk-O1 250×4.6 mm; UV 258 nm; 35° C.; flow rate 2.0 mL/min; mobile phase $CO_2$/MeOH; gradient time 20 min, 30% MeOH (0-1 min), 30-48% MeOH (1-19 min), 48% MeOH (19-20 min). Chiral HPLC purity >99.8% (Rt 16.60 min); LC/MS (ES$^+$) 660.36 (M+H, 100); HRMS: calcd. 660.3220, found 660.3197; $[\alpha]_D^{25\,C}$−79.66°(c 1.06, MeOH); Anal. Calcd for $C_{36}H_{45}N_5O_5S.0.6\,H_2O.0.09\,Et_2O$: C, 64.53; H, 7.00; N, 10.35; S, 4.74; $H_2O$, 1.51; $Et_2O$, 0.97. Found: C, 64.50; H, 7.12; N, 10.41; S, 5.14; $H_2O$, 1.52; $Et_2O$, 0.97. The absolute stereochemistry of cycloprop[d]indolo[2,1-a][2]

benzazepine-5-carboxamide, 8-cyclohexyl-N-[(dimethylamino)sulfonyl]-1,1a,2,12b-tetrahydro-11-methoxy-1a-[(3-methyl-3,8-diazabicyclo[3.2.1]oct-8-yl)carbonyl]-, (1aR,12bS)-rel-(−)- is as drawn above, and was determined from an x-ray crystal structure obtained on the (R)-camphorsulfonic acid salt.

Additionally, the following salts were prepared: hydrochloride, phosphate, acetate, sulfate, camsylate, sodium, calcium, and magnesium. The hydrochloride salt had the following characteristics. DSC: small, broad endotherm from 25° C. to 75° C., and potential melt/degradation endotherm with peak at temperatures ranging between 253° C. and 258° C.; TGA: Early weight loss from 25° C. to 75° C. ranging between 0.003% and 1.5%, and degradation weight loss starting at approximately 200° C.

EXAMPLE 7

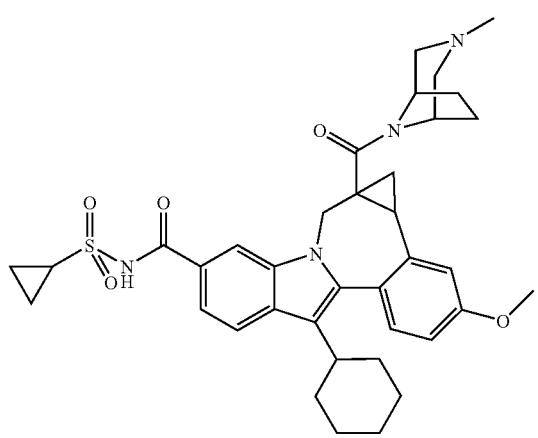

Cycloprop[d]indolo[2,1-a][2]benzazepine-5-carboxamide, 8-cyclohexyl-N-(cyclopropylsulfonyl)-1,1a,2,12,b-tetrahydro-11-methoxy-1a-[(3-methyl-3,8-diazabicyclo[3.2.1]oct-8-yl)carbonyl]-, (+/−)-. (+/−) 8-cyclohexyl-5-(cyclopropylsulfonylcarbamoyl)-1,1a,2,12b-tetrahydro-11-methoxy-cycloprop[d]indolo[2,1-a][2]benzazepine-1a-carboxylic acid (1 equiv) was combined with 3-methyl-3,8-diazabicyclo[3.2.1]octane (1.2 equiv), triethylamine (3 equiv) and TBTU (1.3 equiv) in anhydrous DMF and stirred at rt for approximately 2 h until the reaction was observed to go to completion by LCMS analysis. The product was then isolated by preparative reverse phase HPLC to provide the mono TFA salt of the desired title compound as a beige solid. LC/MS: Retention time: 2.986 min; m/e 657 (MH$^+$). The compound was observed to exist as inter-converting rotamers by $^1$H NMR (400 MHz, CHLOROFORM-D): δ ppm 0.22-0.36 (m, 1 H) H), 1.09-1.20 (m, J=8.06 Hz, 3 H), 1.18-1.30 (m, 2 H) 1.29-1.48 (m, 5 H), 1.48-1.67 (m, 1H), 1.68-1.86 (m, 3 H), 1.87-2.09 (m, 5 H), 2.11-2.40 (m, 1 H), 2.42-2.67 (m, 1 H), 2.67-2.88 (m, J=4.78 Hz, 1 H), 2.86-3.02 (m, 2 H), 3.02-3.28 (m, 2 H), 3.42-3.55 (m, 1 H), 3.55-3.77 (m, 2 H), 3.83-3.92 (m, 3 H), 3.93-4.15 (m, 1 H), 4.28-4.58 (m, 1 H), 4.61-4.99 (m, J=106.26 Hz, 1 H), 5.04-5.26 (m, 1 H), 6.90-7.03 (m, 1 H), 7.07-7.15 (m, J=2.52 Hz, 1 H), 7.27-7.36 (m, 1 H), 7.42-7.68 (m, 1 H), 7.82-7.96 (m, J=8.56 Hz, 1 H), 8.01-8.18 (m, 1 H).

EXAMPLE 8

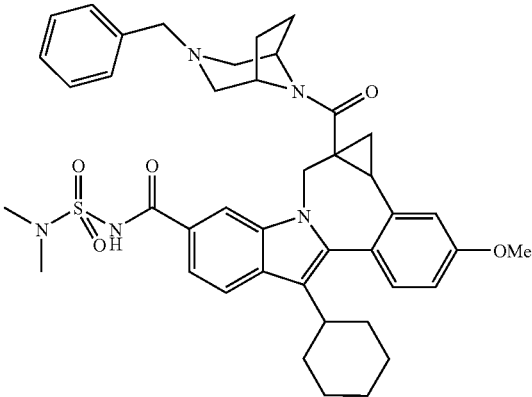

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[3-(phenylmethyl)-3,8-diazabicyclo[3.2.1]oct-8-yl]carbonyl]-, (+/−)-. To a solution of cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (40 mg, 0.0725 mmol) in DMSO (1.0 mL), TBTU (35 mg, 0.109 mmol) and DIPEA (0.076 mL, 0.435 mmol) were added. The reaction mixture was stirred at rt. for 15 min. The mixture from the preparation of benzyl 3,8-diazabicyclo[3.2.1]octane-3-carboxylate described above was then added and the reaction was stirred at rt overnight. It was then concentrated and the residue was purified by preparative reverse phase HPLC to give the product as a light yellow solid, (12.5 mg, 20% yield). MS m/z 736(MH$^+$), Retention time: 2.631 min. 1H NMR (500 MHz, MeOD) δ ppm 0.20 (m, 0.16 H) 1.11-2.25 (m, 15.84 H) 2.57 (m, 0.16 H) 2.70 (m, 0.84 H) 2.85 (m, 0.16 H) 2.80-3.60 (m, 11.84 H) 3.65 (d, J=15.26 Hz, 0.84 H) 3.92 (s, 3 H) 4.22 (d, J=14.95 Hz, 0.16 H) 4.33-4.76 (m, 3 H) 4.96 (m, 0.16 H) 5.08-5.33 (m, 0.84 H) 6.97-7.10 (m, 1 H) 7.17 (d, J=2.44 Hz, 0.16 H) 7.22 (d, J=2.44 Hz, 0.84 H) 7.28-7.42 (m, 1 H) 7.43-7.74 (m, 6 H) 7.87-7.96 (m, 1 H) 7.99-8.19 (m, 1 H).

EXAMPLE 9

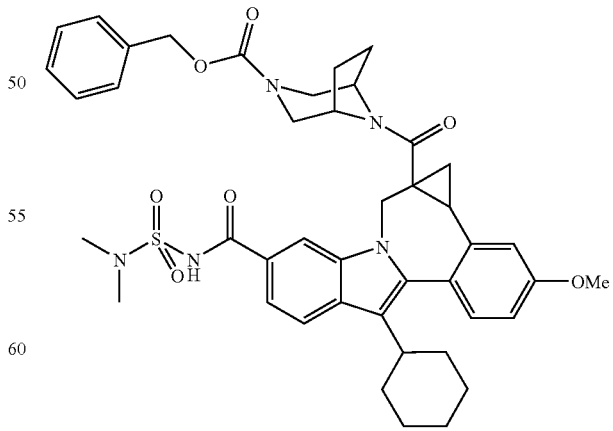

3,8-Diazabicyclo[3.2.1]octane-3-carboxylic acid, 8-[[8-cyclohexyl-5-[[[(dimethylamino)sulfonyl]amino]carbonyl]-

1,12b-dihydro-]11-methoxycycloprop[d]indolo[2,1-a][2]benzazepin-1a(2H)-yl]carbonyl]-, phenylmethyl ester, (+/−)-. To a solution of cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (40 mg, 0.0725 mmol) in DMSO (1.0 mL), TBTU (35 mg, 0.109 mmol) and DIPEA (0.076 mL, 0.435 mmol) were added. The reaction mixture was stirred at rt for 15 min. The mixture from the preparation of benzyl 3,8-diazabicyclo[3.2.1]octane-3-carboxylate was then added and the reaction was stirred at rt. overnight. It resultant mixture was then concentrated in-vacuo and the residue was purified by preparative reverse phase HPLC to give the product as a light yellow solid, (42 mg, 74% yield). MS m/z 780(MH$^+$), Retention time: 3.070 min. 1H NMR (500 MHz, MeOD) δ ppm 0.14 (m, 0.22 H) 1.06-2.20 (m, 15.78 H) 2.51 (m, 0.22 H) 2.58-3.23 (m, 9.78 H) 3.54-4.07 (m, 6.78 H) 4.16 (d, J=14.65 Hz, 0.22 H) 4.31-4.59 (m, br, 1 H) 4.96 (m, 0.22 H) 5.02-5.23 (m, 2.78 H) 6.94-7.07(m, 1 H) 7.16 (d, J=2.44 Hz, 0.22 H) 7.21 (s, 0.78 H) 7.26-7.45 (m, 6 H) 7.50-7.65(m, H) 7.82-8.04 (m, 1.78 H) 8.10 (s, 0.22 H).

EXAMPLE 10

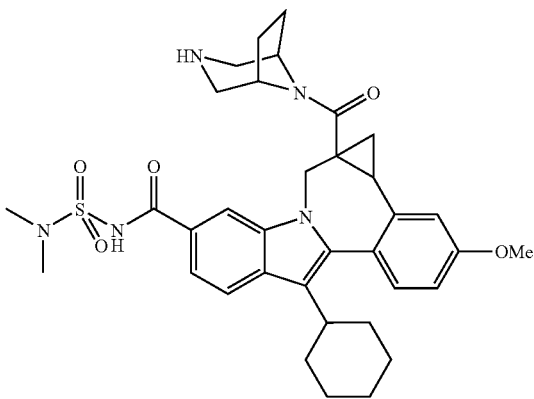

Cycloprop[d]indolo[2,1-a][2]benzazepine-5-carboxamide, 8-cyclohexyl-1a-(3,8-diazabicyclo[3.2.1]oct-8-ylcarbonyl)-N-[(dimethylamino)sulfonyl]-1,1a,2,12b-tetrahydro-11-methoxy-, (+/−)-. To a solution of 3,8-diazabicyclo[3.2.1]octane-3-carboxylic acid, 8-[[8-cyclohexyl-5-[[[(dimethylamino)sulfonyl]amino]carbonyl]-1,12b-dihydro-11-methoxycycloprop[d]indolo[2,1-a][2]benzazepin-1a(2H)-yl]carbonyl]-, phenylmethyl ester (360 mg, 0.462 mmol) in methanol/ethyl acetate (20 mL/20 mL), 10% Pd on carbon (40 mg) was added. The reaction mixture was stirred under a hydrogen atmosphere (1 atm) overnight. The mixture then filtered through celite, and the filtrand washed with methanol and ethyl acetate. The combined filtrates were concentrated to give the product as a yellow solid, (275 mg, 92% yield). MS m/z 646 (MH$^+$), Retention time: 2.983 min. 1H NMR (500 MHz, MeOD) δ ppm 0.20 (m, 0.2 H) 1.12-2.29 (m, 15.8 H) 2.52-2.86 (m, 1.2 H) 2.99 (m, 0.8 H) 3.02 (s, 4.8 H) 3.03 (s, 1.2 H) 3.09-3.49 (m, 5 H) 3.68 (d, J=15.26 Hz, 0.8 H) 3.91 (s, 2.4 H) 3.92 (s, 0.6 H) 4.03-4.26 (m, 0.4 H) 4.62-4.85 (m, 1 H) 5.17 (d, J=13.71 Hz, 0.8 H) 6.99-7.11 (m, 1 H) 7.19 (s, 0.2 H) 7.23 (s, 0.8 H) 7.32-7.40 (m, 1 H) 7.59 (d, J=8.24 Hz, 0.8 H) 7.63 (d, J=8.24 Hz, 0.2 H) 7.89-7.96 (m, 1 H) 7.98 (s, 0.8 H) 8.09 (s, 0.2 H).

EXAMPLE 11

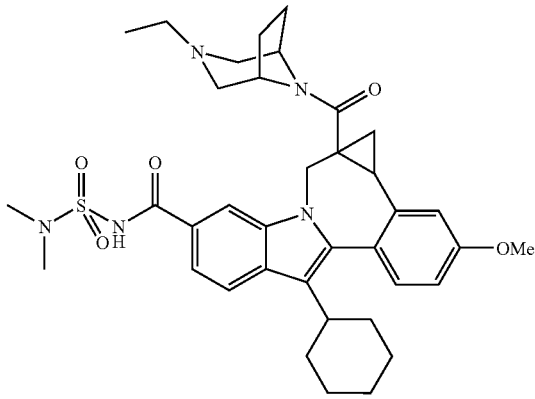

Cycloprop[d]indolo[2,1-a][2]benzazepine-5-carboxamide, 8-cyclohexyl-N-[(dimethylamino)sulfonyl]-1a-[(3-ethyl-3,8-diazabicyclo[3.2.1]oct-8-yl)carbonyl]-1,1a,2,12b-tetrahydro-11-methoxy-, (+/−)-. To a solution of (+/−) cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-(3,8-diazabicyclo[3.2.1]oct-8-yl)carbonyl]- (30 mg, 0.0465 mmol) in methanol (2 mL), acetaldehyde (0.013 mg, 0.232 mmol), ZnCl$_2$ (19 mg, 0.14 mmol) and Na(CN)BH$_3$ (8.8 mg, 0. 14 mmol) were added. The resultant mixture was stirred at rt overnight, during which time a precipitate formed. This solid was removed by filtration, and the filtrate concentrated under vacuum. The residue was then purified by preparative reverse phase HPLC to provide the TFA salt of the title compound as a light yellow solid, (35 mg, 96% yield). MS m/z 674 (MH$^+$), Retention time: 3.013 min. 1H NMR (500 MHz, MeOD) δ ppm 0.22 (m, 0.16 H) 1.09-2.29 (m, 18.84 H) 2.59 (m, 0.16 H) 2.70 (m, 0.84 H) 2.86 (m, 0.16 H) 2.97-3.03 (m, 5.88 H) 3.03 (s, 0.96 H) 3.11-3.81 (m, 7 H) 3.92 (s, 2.52 H) 3.93 (s, 0.48 H) 4.22 (d, J=14.95 Hz, 0.16 H) 4.39 (s, br, 0.84 H) 4.60-4.85 (m, 1.16 H) 5.20 (d, J=14.64 Hz, 0.84 H) 7.01-7.09 (m, 1 H) 7.20 (d, J=2.75 Hz, 0.16 H) 7.22 (d, J=2.44 Hz, 0.84 H) 7.33-7.38 (m, 1 H) 7.59 (dd, J=8.39, 1.37 Hz, 0.84 H) 7.63 (dd, J=8.55, 1.53 Hz, 0.16 H) 7.90-7.96 (m, 1 H) 8.02 (s, 0.84 H) 8.09 (s, 0.16 H).

EXAMPLE 12

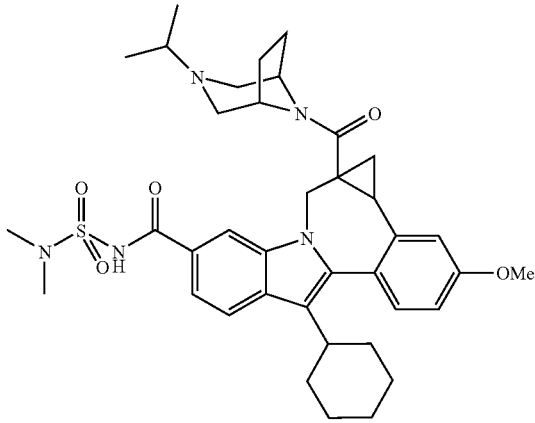

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[3-(1-methylethyl)-3,8-diazabicyclo[3.2.1]oct-8-yl]carbonyl]-, (+/−)-. To a solution of (+/−) cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-(3,8-diazabicyclo[3.2.1]oct-8-yl)carbonyl]- (30 mg, 0.0465 mmol) in methanol (2 mL), acetone (0.010 mg, 0.14 mmol) and $ZnCl_2$ (19 mg, 0.14 mmol) were added. The reaction mixture was heated at 50° C. for 1 hr. Then $Na(CN)BH_3$ (8.8 mg, 0.14 mmol) was added, and the reaction was maintained at 50° C. overnight, during which time a precipitate formed. This material was removed by filtration, and the filtrate was then concentrated in-vacuo. The resultant residue was then purified by Preparative HPLC column to give the TFA salt of the title compound as a light yellow solid, (35 mg, 94% yield). MS m/z 688 (MH−), Retention time: 3.011 min. 1H NMR (500 MHz, MeOD) δ ppm 0.21 (m, 0.19 H) 1.11-2.24 (m, 21.81 H) 2.58 (m, 0.19 H) 2.72 (m, 0.81 H) 2.85 (m, 0.19 H) 2.93-3.03 (m, 5.67 H) 3.03 (s, 1.14 H) 3.14-3.73 (m, 6 H) 3.91 (s, 2.43 H) 3.93 (s, 0.57 H) 4.22 (d, J=14.95 Hz, 0.19 H) 4.39 (s, br, 0.81 H) 4.58-4.80 (m, br, 1 H) 4.84 (m, 0.19 H) 5.19 (d, J=15.26 Hz, 0.81 H) 6.99-7.09 (m, 1 H) 7.20 (d, J=2.44 Hz, 0.19 H) 7.23 (d, J=2.44 Hz, 0.81 H) 7.31-7.39 (m, 1 H) 7.58 (d, J=8.55 Hz, 0.81 H) 7.63 (d, J=8.55 Hz, 0.19 H) 7.93 (d, J=8.24 Hz, 1 H) 8.01 (s, 0.81 H) 8.11 (s, 0.19 H).

EXAMPLE 13

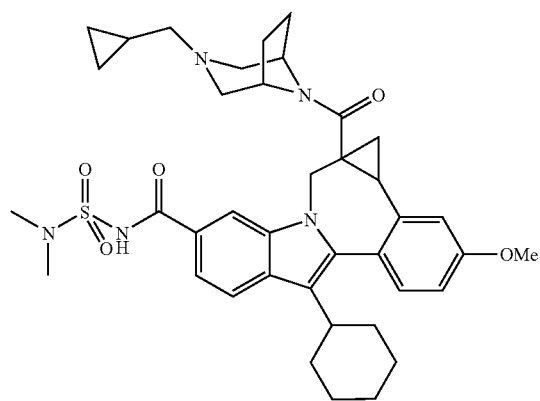

Cycloprop[d]indolo[2,1-a][2]benzazepine-5-carboxamide, 8-cyclohexyl-1a-[[3-(cyclopropylmethyl)-3,8-diazabicyclo[3.2.1]oct-8-yl]carbonyl]-N-[(dimethylamino)sulfonyl]-1,1a,2,12b-tetrahydro-11-methoxy-, (+/−)-. To a solution of (+/−) cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-(3,8-diazabicyclo[3.2.1]oct-8-yl)carbonyl]- (20 mg, 0.031 mmol) in methanol (2 mL), cycloporpanecarboxaldehyde (0.007 mg, 0.093 mmol), $ZnCl_2$ (12.7 mg, 0.093 mmol) and $Na(CN)BH_3$ (5.8 mg, 0.093 mmol) were added. The mixture was stirred at rt. for 2 hr, after which an insoluble solid was removed by filtration. The filtrate was concentrated in-vacuo, and the resultant residue purified by preparative reverse phase HPLC to give the TFA salt of the title compound as light yellow solid,(10 mg, 40% yield). MS m/z 700 (MH+), Retention time: 3.033 min. 1H NMR (500 MHz, MeOD) δ ppm 0.21 (m, 0.18 H) 0.47 (s, br, 2 H) 0.69-0.85 (m, 2 H) 0.93-2.29 (m, 16.82 H) 2.58 (m, 0.18 H) 2.71 (m, 0.82 H) 2.86 (m, 0.18 H) 2.94-3.80 (m, 13.82 H) 3.91 (s, 2.46 H) 3.93 (s, 0.54 H) 4.23 (d, J=14.95 Hz, 0.18 H) 4.41 (s, br, 0.82 H) 4.61-4.79 (m, 1 H) 4.98 (m, 0.18 H) 5.19 (d, J=14.35 Hz, 0.82 H) 7.01-7.09 (m, 1 H) 7.19 (d, J=2.75 Hz, 0.18 H) 7.22 (d, J=2.44 Hz, 0.82 H) 7.32-7.39 (m, 1 H) 7.58 (d, J=8.24 Hz, 0.82 H) 7.63 (d, J=8.24 Hz, 0.18 H) 7.90-7.96 (m, 1 H) 8.02 (s, 0.82 H) 8.09 (s, 0.18 H).

EXAMPLE 14

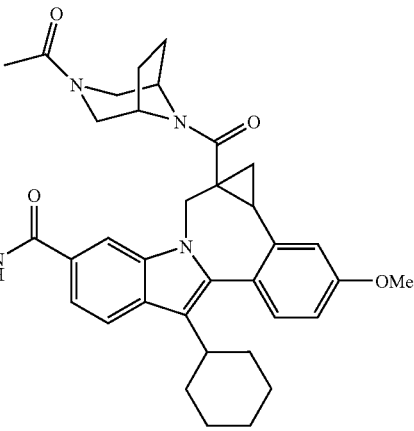

Cycloprop[d]indolo[2,1-a][2]benzazepine-5-carboxamide, 1a-[(3-acetyl-3,8-diazabicyclo[3.2.1]oct-8-yl)carbonyl]-8-cyclohexyl-N-[(dimethylamino)sulfonyl]-1,1a,2,12b-tetrahydro-11-methoxy-, (+/−)-. TBTU (15 mg, 0.0465 mmol) and DIPEA (0.027 mL, 0.155 mmol) were added to a solution of acetic acid (3 mg, 0.0465 mmol) in DMSO (1.0 mL), and the mixture was stirred at rt for 15 min. (+/−) Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-(3,8-diazabicyclo[3.2.1]oct-8-yl)carbonyl]- (20 mg, 0.031 mmol) was then added and the reaction was stirred at rt overnight. It was then concentrated, and the residue was purified by Preparative HPLC column to provide the title compound as a light yellow solid, (7 mg, 33% yield). MS m/z 688 (MH+), Retention time: 3.278 min. 1H NMR (500 MHz, MeOD) δ ppm 0.18 (m, 0.2 H) 1.07-2.27 (m, 18.8 H) 2.55 (m, 0.2 H) 2.72 (m, 0.8 H) 2.86 (m, 0.2 H) 2.95-3.08 (m, 6.8 H) 3.15-3.78 (m, 5 H) 3.91 (s, 2.4 H) 3.93 (s, 0.6 H) 4.05-4.29 (m, 1 H) 4.40-4.59 (m, 1 H) 4.93 (m, 0.2 H) 5.16 (m, 0.8 H) 6.99-7.10 (m, 1 H) 7.19 (m, 0.2 H) 7.23 (d, J=2.14 Hz, 0.8 H) 7.30-7.41 (m, 1 H) 7.59 (d, J=8.85 Hz, 0.8 H) 7.64 (d, J=8.24 Hz, 0.2 H) 7.86-8.06 (m, 1.8 H) 8.13 (s, 0.2 H).

EXAMPLE 15

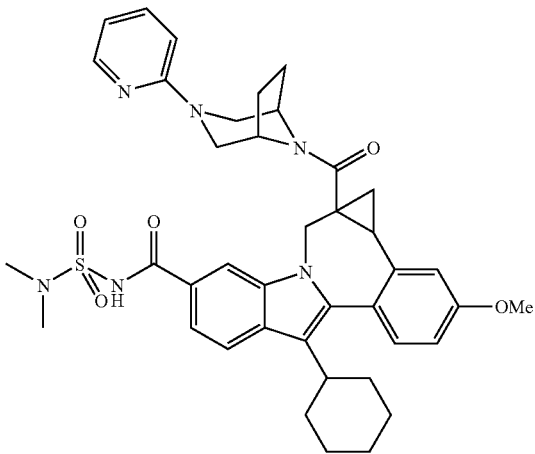

Cycloprop[d]indolo[2,1-a][2]benzazepine-5-carboxamide, 8-cyclohexyl-N-[(dimethylamino)sulfonyl-1,1a,2,12b-tetrahydro-11-methoxy-1a-[[3-(2-pyridinyl)-3,8-diazabicyclo[3.2.1]oct-8-yl]carbonyl]-, (+/−)-. In a microwave reaction tube, (+/−) cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-(3,8-diazabicyclo[3.2.1]oct-8-yl)carbonyl]- (20 mg, 0.031 mmol), Pd$_2$(dba)$_3$ (0.6 mg, 2 mol %), 1,3-bis(diphenylphosphino)propane (0.5 mg, 4 mol %), sodium t-butoxide (8.9 mg, 0.093 mmol) and 2-bromopyridine (0.006 mL, 0.062 mmol) were added under nitrogen. The reaction tube was then sealed and dioxane (1 mL) was added, and the reaction mixture was then heated at 70° C. in an oil bath overnight. The reaction was then filtered and concentrated, and the residue was purified by Preparative HPLC column to give the TFA salt of the title compound as an off-white solid, (2.2 mg, 7.5% yield). MS m/z 723 (MH$^+$), Retention time: 3.048 min. 1H NMR (500 MHz, MeOD) δ ppm 0.25 (m, 0.2 H) 1.11-2.23 (m, 15.8 H) 2.60 (m, 0.2 H) 2.76 (m, 0.8 H) 2.79-3.10 (m, 7 H) 3.13-4.00 (m, 8 H) 4.27 (d, J=15.26 Hz, 0.2 H) 4.46 (s, br, 0.8 H) 4.63-4.81 (m, 1 H) 4.99 (m, 0.2 H) 5.26 (d, J=15.26 Hz, 0.8 H) 7.02-7.16 (m, 2 H) 7.20-7.27 (m, 1 H) 7.32-7.68 (m, 3 H) 7.77 (d, J=7.93 Hz, 0.2 H) 7.85-8.18 (m, 3.8 H).

EXAMPLE 16

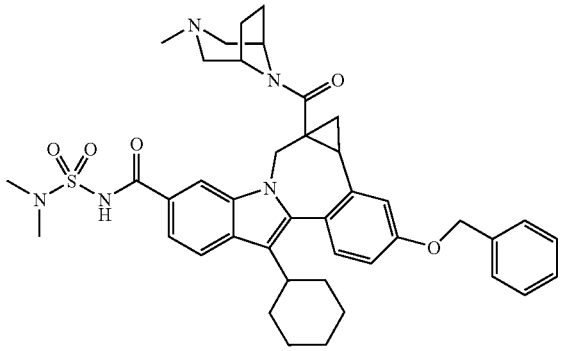

Cycloprop[d]indolo[2,1-a][2]benzazepine-5-carboxamide, 8-cyclohexyl-N-[(dimethylamino)sulfonyl]-1,1a,2,12b-tetrahydro-1a-[(3-methyl-3,8-diazabicyclo[3.2.1]oct-8-yl)carbonyl-]1-(phenylmethoxy)-, (+/−)-. (+/−) Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-(phenylmethoxy)-, (496 mg, 0.79 mMol) was dissolved in 7 ml of DMF and TBTU (392 mg, 1.22 mMol) added and the reaction was stirred under nitrogen for 1 hour at room temperature after which DMAP (525 mg, 4.29 mMol) was added followed by 3-methyl-3,8-diaza-bicyclo[3.2.1]octane dihydrochloride (196 mg, 0.98 mMol). The reaction was stirred at room temperature under a nitrogen atmosphere for 17 hours and then poured in to 100 ml of water. The aqueous mixture was extracted with ethyl acetate. The organic extract was washed twice with water, then brine and dried over magnesium sulfate. Removal of volatiles in vacuuo gave 615 mg of crude product which was adsorbed onto 1.5 of silica gel and chromatographed on 18 of silica gel eluting with 3% methanol in dichloromethane. The pure product fractions combined and volatiles removed in vacuuo to yield 216 mg (37%) of a nearly colorless amorphous solid. 1H NMR (500 MHz, CHLOROFORM-D) δ ppm 0.27 (t, J=5.80 Hz, 0.4 H) 1.14-1.30 (m, 2.9H) 1.30-1.48 (m, 3.7 H) 1.57 (d, J=15.26 Hz, 2.3 H) 1.63-1.87 (m, 11.2 H) 1.85-2.20 (m, 8.4 H) 2.30 (s, 1.3 H) 2.39 (s, 0.9 H) 2.69 (s, 1.2 H) 2.79 (s, 1.2 H) 2.85-3.01 (m, 1.9 H) 3.01-3.11 (m, 6.0 H) 3.25-3.51 (m, 1.8 H) 3.59 (d, J=15.26 Hz, 1.2 H) 4.14 (d, J=14.95 Hz, 0.4 H) 4.40 (s, 0.9 H) 4.75 (d, J=13.73 Hz, 0.4 H) 5.07-5.21 (m, 2.8 H) 6.92-7.11 (m, 1.5 H) 7.21 (d, J=2.75 Hz, 1.0 H) 7.27-7.49 (m, 7.0 H) 7.53 (d, J=7.93 Hz, 0.6 H) 7.87 (dd, J=8.55, 4.88 Hz, 1.0 H) 7.91-8.03 (m,0.9 H) 8.83 (s, 0.2 H) 9.67 (s, 0.3 H).

EXAMPLE 17

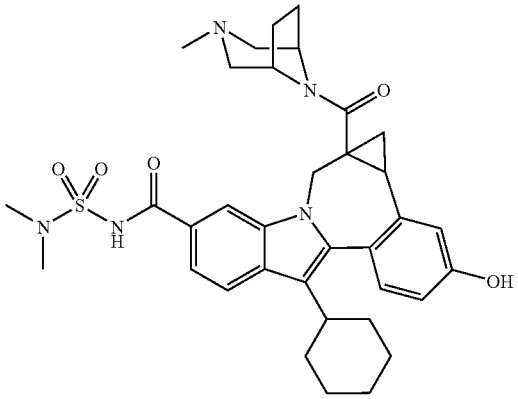

Cycloprop[d]indolo[2,1-a][2]benzazepine-5-carboxamide, 8-cyclohexyl-N-[(dimethylamino)sulfonyl]-1,1a,2,12b-tetrahydro-11-hydroxy-la-[(3-methyl-3,8-diazabicyclo[3.2.1]oct-8-yl)carbonyl]-, (+/−)-. (+/−) Cycloprop[d]indolo[2,1-a][2]benzazepine-5-carboxamide, 8-cyclohexyl-N-[(dimethylamino)sulfonyl]-1,1a,2,12b-tetrahydro-1a-[(3-methyl-3,8-diazabicyclo[3.2.1]oct-8-yl)carbonyl]-11-(phenylmethoxy)- (189 mg, 0.26 mMol) was dissolved in a mixture of 5 ml methanol and 2 ml of inhibitor free THF using heat. Upon cooling some material precipitated out. Aqueous 1N hydrochloric acid (0.3 ml, 0.3 mMol) was added to aid dissolution. The reaction was placed under a nitrogen atmosphere prior to the addition of 20% palladium hydroxide on carbon (46 mg). The reaction was run under hydrogen at atmospheric pressure (balloon) and room temperature for 6.75 hours. The reaction was filtered through a plug of ceilite. The volatiles of the filtrate were removed in vacuuo to yield 161 mg (92%) product as a pale yellow solid. 1H NMR (500

MHz, DMSO-D6) δ ppm 0.01 (t, J=5.34 Hz, 0.3 H) 0.39 (s, 0.3 H) 1.08-1.60 (m, 6.6 H) 1.62-1.83 (m, 2.9 H) 1.82-2.20 (m, 6.3H) 2.58-2.84 (m, 4.9 H) 2.84-2.96 (m, 6.9 H) 3.07-3.19 (m, 1.0 H) 3.20-3.29 (m, 1.6 H) 3.34 (s, 10.0H, H2O) 3.42 (s, 0.9 H) 3.58 (d, J=14.65 Hz, 0.8 H) 4.13 (d, J=14.95 Hz, 0.4 H) 4.31-4.62 (m, 0.8 H) 4.91 (d, J=14.95 Hz, 0.3 H) 4.98-5.21 (m, 0.7 H) 6.85 (t, J=8.55 Hz, 1.1 H) 6.99 (s, 1.0 H) 7.09-7.25 (m,1.0 H) 7.62 (d, J=20.14 Hz, 1.0 H) 7.72-7.91 (m, 1.0 H) 7.92-8.29 (m, 0.9 H) 9.92 (s, 1.0 H) 10.16 (d, J=56.15 Hz, 0.8 H) 11.63 (d, J=10.68 Hz, 0.9 H).

EXAMPLE 18

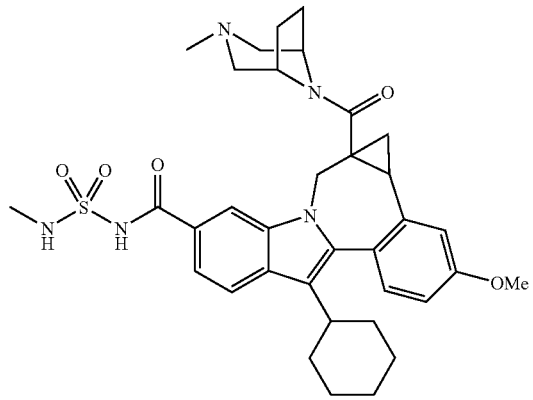

Cycloprop[d]indolo[2,-a][2]benzazepine-5-carboxamide, 8-cyclohexyl-1,1a,2,12b-tetrahydro-11-methoxy-N-[(methylamino)sulfonyl]-1a-[(3-methyl-3,8-diazabicyclo[3.2.1]oct-8-yl)carbonyl]-, (−)-. A solution of cycloprop[d]indolo[2,1-a][2]benzazepine-1a(2H)-carboxylic acid, 8-cyclohexyl-5-[[[(methylamino)sulfonyl]amino]carbonyl]-1,12b-dihydro-11-methoxy- (158 mg, 0.29 mmol), 3-methyl-3,8-diaza-bicyclo[3.2.1]octane dihydrochloride (59 mg, 0.29 mmol), diisopropyl ethyl amine (0.15 mL), and TBTU (112 mg, 0.35 mmol) in DMF (1.5 mL) was stirred for 1 hr at 22° C. and purified by prep HPLC to afford the title compound as a pale yellow solid (150 mg, 80.1%). ESI-MS m/e 646 (MH+), 1H NMR (500 MHz, MeOD) δ ppm 0.93-2.08 (m, 16 H) 2.49-2.53 (m, 1 H) 2.55 (s, 3 H) 2.60-2.93 (m, 4 H) 3.15 (s, 3 H) 3.24 (m, 2 H) 3.73 (s, 3 H) 3.88-4.18 (m, 1 H) 4.41-4.56 (m, 1 H) 4.86-5.03 (m, 1 H) 6.86 (d, J=8.24 Hz, 1 H) 6.97-7.06 (m, 1 H) 7.09-7.20 (m, 1 H) 7.37-7.49 (m, 1 H) 7.73 (d, J=8.24 Hz, 1 H) 7.77-7.94 (m, 1 H).

EXAMPLE 19

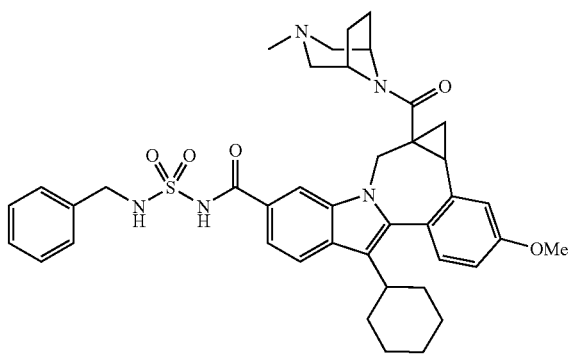

Cycloprop[d]indolo[2,1-a][2]benzazepine-5-carboxamide, 8-cyclohexyl-1,1a,2,12b-tetrahydro-11-methoxy-1a-[(3-methyl-3, 8-diazabicyclo[3.2.1]oct-8-yl)carbonyl]-N-[[(phenylmethyl)amino]sulfonyl]-, (+/−)-. (+/−) 8-cyclohexyl-N-((benzylamino)sulfonyl)-1a-((3-methyl-3,8-diazabicyclo[3.2.1]oct-8-yl)carbonyl)-11-(methyloxy)-1,1a,2,12b-tetrahydrocyclopropa[d]indolo[2,1-a][2]benzazepine-5-carboxamide was prepared in a similar fashion to that described for the synthesis of (−) 8-cyclohexyl-N-((methylamino)sulfonyl)-1a-((3-methyl-3,8-diazabicyclo[3.2.1]oct-8-yl)carbonyl)-11-(methyloxy)-1,1a,2,12b-tetrahydrocycloprop[d]indolo[2,1-a][2]benzazepine-5-carboxamide starting from (+/−) Cycloprop[d]indolo[2,1-a][2]benzazepine-1a(2H)-carboxylic acid, 8-cyclohexyl-5-[[[(benzylamino)sulfonyl]amino]carbonyl]-1,12b-dihydro-11-(methoxy)-12-(methoxy)-, methyl ester. ESI-MS m/e 722 (MH+), 1H NMR (500 MHz, MeOD) δ ppm 1.14-2.20 (m, 16 H) 2.56-3.08 (m, 7 H) 3.39-3.72 (m, 3 H) 3.89-3.96 (m, 3 H) 4.21-4.37 (m, 3 H) 4.60-4.74 (m, 1 H) 5.11-5.22 (m, 1 H) 7.06 (dd, J=8.55, 2.44 Hz, 1 H) 7.17-7.24 (m, 2 H) 7.28 (t, J=7.63 Hz, 2 H) 7.33-7.43 (m, 3 H) 7.45-7.56 (m, 1 H) 7.86-8.00 (m, 2 H).

EXAMPLE 20

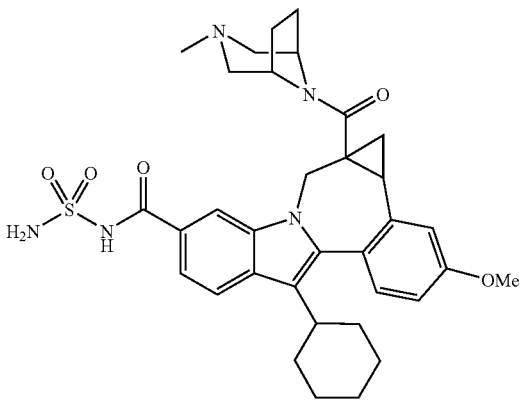

Cycloprop[d]indolo[2,1-a][2]benzazepine-5-carboxamide, N-(aminosulfonyl)-8-cyclohexyl-1,1a,2,12b-tetrahydro-11-methoxy-1a-[(3-methyl-3,8-diazabicyclo[3.2.1]oct-8-yl)carbonyl]-, (+/−)-. 10% Palladium on carbon (40 mg, 0.038 mmol) was added to a solution of (+/−) 8-cyclohexyl-N-((benzylamino)sulfonyl)-1a-((3-methyl-3,8-diazabicyclo[3.2.1]oct-8-yl)carbonyl)-11-(methyloxy)-1,1a,2,12b-tetrahydrocyclopropa[d]indolo[2,1-a][2]benzazepine-5-carboxamide(+/−)(20 mg, 0.028 mmol) in EtOH (10 mL) and the reaction mixture was sequentially subjected to a vacuum and then flushed with nitrogen three times before being placed under a hydrogen atomosphere (1 atm). The reaction mixture was stirred at rt for two days before being filtered through a pad of celite and concentrated. The residue was purified by preparative HPLC (Acetonitrile/H2O with a TFA buffer) to yield the title compound as a white film. ESI-MS m/e 632 (MH+), 1H NMR (500 MHz, MeOD) δ ppm 1.13-2.23 (m, 16 H) 2.48-3.11 (m, 9 H) 3.54-3.75 (m, 1 H) 3.86-3.97 (m, 3 H) 4.15-4.37 (m, 1 H) 4.62 (s, 1 H) 5.19 (s, 1 H) 7.05 (s, 1 H) 7.16-7.24 (m, 1 H) 7.31-7.39 (m, 1 H) 7.55-7.67 (m, 1 H) 7.88-7.97 (m, 1 H) 7.99-8.12 (m, 1 H).

Examples 20-31 were analyzed by the following LC/MS method: Analysis Conditions: Column: PHENOMENNEX-LUNA 3.0×50 mm S10; Mobile Phase: (A) 10:90 methanol-water; (B) 90:10 methanol-water; Buffer: 0.1% TFA; Gradient Range: 0-100% B; Gradient Time: 2 min; Flow Rate: 4 mL/min; Analysis Time: 3 min; Detection: Detector 1: UV at 220 nm; Detector 2: MS (ESI+).

EXAMPLE 21

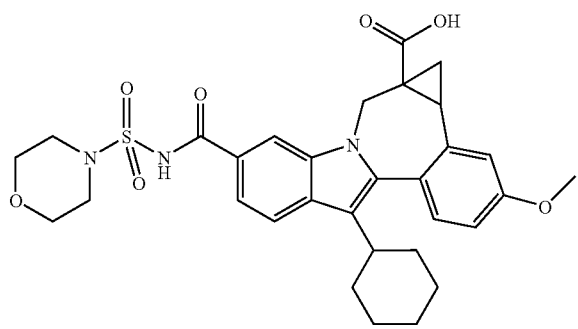

(+/−)-8-Cyclohexyl-5-(morpholinosulfonylcarbamoyl)-1,1a,2,12b-tetrahydro-11-methoxy-cycloprop[d]indolo[2,1-a][2]benzazepine-1a-carboxylic acid. The product was purified by prep HPLC and isolated as a beige solid. LC/MS: Retention time: 1.968 min; m/e 460 (MH+). $^1$H NMR (400 MHz, CDCl$_3$): The compound was observed to exist as inter-converting rotamers.

EXAMPLE 22

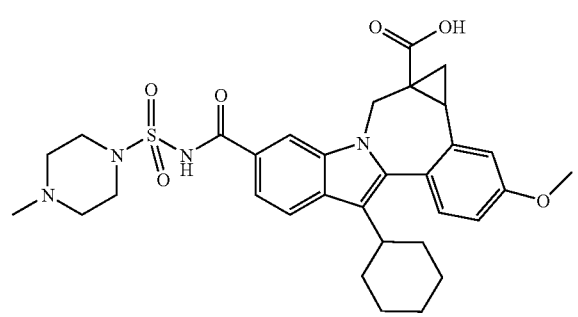

(+/−)-8-Cyclohexyl-5-(4-ethylpiperazin-1-ylsulfonylcarbaoyl)-1,1a,2,12b-tetrahydro-11-methoxy-cycloprop[d]indolo[2,1-a][2]benzazepine-1a-carboxylic acid. The product was purified by prep HPLC and isolated in mono TFA salt form as a beige solid. LC/MS: Retention time: 1.687 min; m/e 607 (MH+). $^1$H NMR (400 MHz, CDCl$_3$): The compound was observed to exist as inter-converting rotamers.

EXAMPLE 23

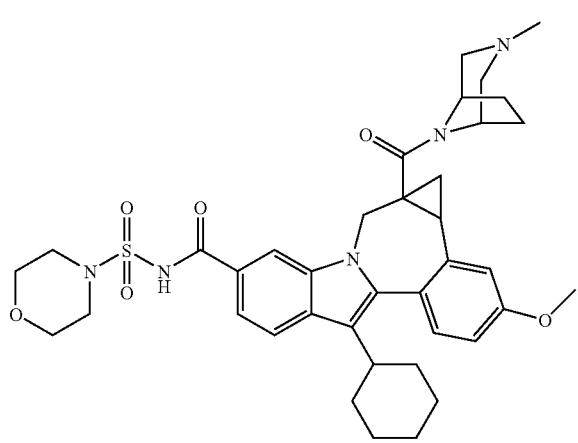

(+/−)-8-Cyclohexyl-N-4-(morpholinosulfonyl)-1,1a,2,12b-tetrahydro-11-methoxy-1a-(3-methyl-3,8-diazabicyclo[3.2.1]octane-8-carbonyl)cycloprop[d]indolo[2,1-a][2]benzazepine-5-carboxamide. The product was purified by prep HPLC and isolated as the TFA salt. LC/MS: Retention time: 1.770 min; m/e 702 (MH+). The compound was observed to exist as inter-converting rotamers by 1H NMR (500 MHz, CHLOROFORM-D): δ ppm 1.14-1.59 (m, 7 H), 1.69-1.88 (m, 3 H), 1.87-2.15 (m, 6 H,), 2.49-2.66 (m, 1 H), 2.80-3.02 (m, 3 H), 3.05-3.32 (m, 1 H), 3.41-3.55 (m, 5 H), 3.58-3.68 (m, J=15.56 Hz, 1 H), 3.70-3.81 (m, 4 H), 3.83-3.93 (m, 3 H), 3.94-4.14 (m, 1 H), 4.43-4.71 (m, 3 H), 4.75-4.87 (m, 1 H), 5.18 (s, 1 H), 6.90-7.02 (m, 1 H), 7.07-7.15 (m, J=2.75 Hz, 1 H), 7.27-7.36 (m, J=9.16, 9.16 Hz, 1 H), 7.37-7.60 (m, 1 H), 7.83-7.95 (m, J=8.39, 8.39 Hz, 1 H), 8.03 (s, 1 H), 9.47 (s, 1 H).

EXAMPLE 24

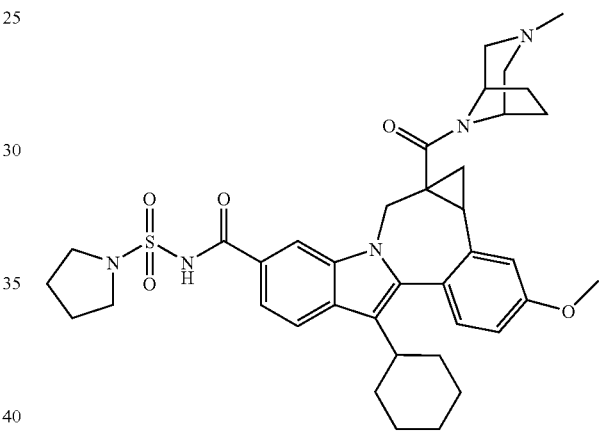

(+/−)-8-Cyclohexyl-N-(pyrrolidin-1-ylsulfonyl)-1,1a,2,12b-tetrahydro-11-methoxy-1a-(3-methyl-3,8-diazabicyclo[3.2.1]octane-8-carbonyl)-cycloprop[d]indolo[2,1-a][2]benzazepine-5-carboxamide. The product was purified by prep HPLC and isolated as the TFA salt. LC/MS: Retention time: 2.873 min; m/e 686 (MH+). The compound was observed to exist as inter-converting rotamers by 1H NMR (400 MHz, CHLOROFORM-D): δ ppm 1.12-1.30 (m, 3 H), 1.29-1.45 (m, 3 H), 1.45-1.60 (m, 2 H), 1.71-1.86 (m, 3 H), 1.86-1.98 (m, J=6.17, 6.17 Hz, 6 H), 1.97-2.12 (m, J=23.42 Hz, 3 H), 2.12-2.32 (m, 1 H), 2.56-2.72 (m, 1 H), 2.80-2.88 (m, J=4.78 Hz, 1 H), 2.88-3.02 (m, 2 H), 3.07-3.23 (m, 1 H), 1 H), 3.45-3.52 (m, 1 H), 3.51-3.60 (m, 4 H), 3.60-3.74 (m, 2 H), 3.85-3.93 (m, 3 H), 4.02-4.18 (m, 1 H), 4.50-4.64 (m, 1 H), 4.78-4.92 (m, 1 H), 5.10-5.26 (m, 1 H), 6.90-7.02 (m, 1 H), 7.07-7.16 (m, J=2.52 Hz, 1 H), 7.26-7.34 (m, J=9.19, 9.19 Hz, 1 H), 7.48-7.64 (m, 1 H), 7.82-7.97 (m, J=9.19, 9.19 Hz, 1 H), 8.08-8.27 (m, 1 H), 9.52 (s, 1 H).

EXAMPLE 25

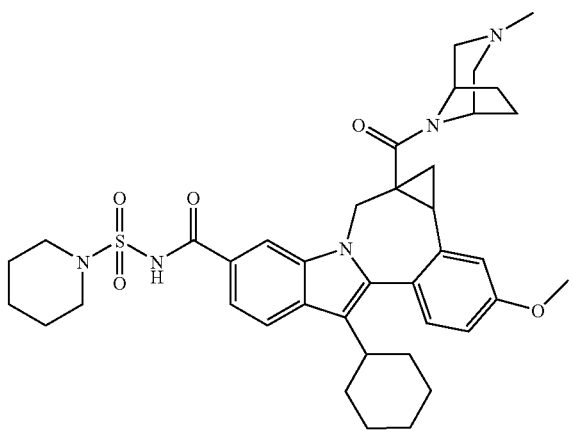

(+/−)-8-Cyclohexyl-N-(piperidin-1-ylsulfonyl)-1,1a,2,12b-tetrahydro-11-methoxy-1a-(3-methyl-3, 8-diazabicyclo[3.2.1]octane-8-carbonyl)cycloprop[d]indolo[2,1-a][2]benzazepine-5-carboxamide. The product was purified by prep HPLC and isolated as the TFA salt. LC/MS: Retention time: 1.882 min; m/e 700 (MH$^+$). The compound was observed to exist as inter-converting rotamers by 1H NMR (400 MHz, CHLOROFORM-D): δ ppm 1.17-1.30 (m, 2 H), 1.30-1.46 (m, J=14.23, 6.92 Hz, 4 H), 1.47-1.61 (m, J=11.33 Hz, 4 H), 1.61-1.72 (m, J=4.03 Hz, 4 H), 1.71-1.86 (m, 3 H), 1.86-2.11 (m, J=10.32 Hz, 6 H), 2.21-2.38 (m, 1 H), 2.51-2.68 (m, 1 H), 2.77-3.02 (m, 3 H), 3.33-3.47 (m, 4 H), 3.47-3.52 (m, 1 H), 3.58-3.73 (m, 2 H), 3.86-3.93 (m, 3 H), 3.93-4.13 (m, 1 H), 4.57-4.77 (m, 2 H), 5.06-5.23 (m, 1 H), 6.91-7.02 (m, 1 H), 7.06-7.16 (m, J=2.52 Hz, 1 H), 7.26-7.33 (m, 1 H), 7.37-7.56 (m, 1 H), 7.82-7.94 (m, 1 H), 7.98-8.12 (m, 1 H), 9.03 (s, 1 H).

EXAMPLE 26

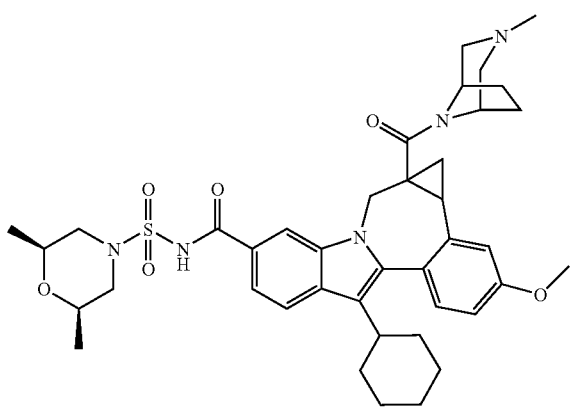

(+/−)-8-Cyclohexyl-N-((2S,6R)-2,6-dimethylmorpholinosulfonyl)-1,1a,2,12b-tetrahydro-11-methoxy-1a-(3-methyl-3,8-diazabicyclo[3.2.1]octane-8-carbonyl)cycloprop[d]indolo[2,1-a][2]benzazepine-5-carboxamide. The product was purified by prep HPLC and isolated as the TFA salt. LC/MS: Retention time: 2.911 min; m/e 730 (MH$^+$). The compound was observed to exist as inter-converting rotamers by 1H NMR (400 MHz, CHLOROFORM-D): δ ppm 1.13-1.23 (m, 5 H), 1.22-1.31 (m, J=5.29 Hz, 1 H), 1.31-1.47 (m, J=7.30, 7.30 Hz, 3 H), 1.47-1.62 (m, 3 H), 1.74-1.91 (m, J=20.90 Hz, 1 H), 1.91-2.10 (m, 2 H), 2.70-2.92 (m, 4 H), 3.02-3.12 (m, 1 H), 3.18-3.39 (m, 6 H), 3.44-3.52 (m, 3 H), 3.58-3.79 (m, 8 H), 3.90 (s, 3 H), 3.92-4.01 (m, 1 H), 4.00-4.11 (m, 1 H), 4.30-4.47 (m, 1 H), 4.80-4.93 (m, 1 H), 5.09-5.23 (m, 1 H), 6.92-7.02 (m, 2 H), 7.08-7.14 (m, J=2.52 Hz, 1 H), 7.29 (d, J=8.31 Hz, 1 H), 7.85-7.93 (m, 1 H), 7.94-8.02 (m, 1 H), 8.85 (s, 1 H).

EXAMPLE 27

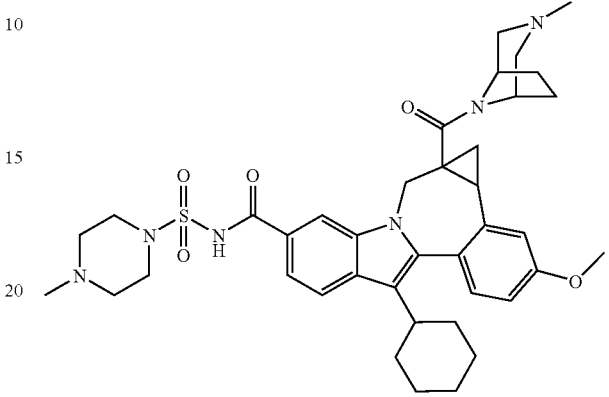

(+/−)-8-Cyclohexyl-N-4-(4-methylpiperazin-1-ylsulfonyl)-1,1a,2,12b-tetrahydro-11-methoxy-1a-(3-methyl-3,8-diazabicyclo[3.2.1]octane-8-carbonyl)cycloprop[d]indolo[2,1-a][2]benzazepine-5-carboxamide. The product was purified by prep HPLC and isolated as bis-TFA salt. LC/MS: Retention time: 1.563 min; m/e 715 (MH$^+$). The compound was observed to exist as inter-converting rotamers by 1H NMR (500 MHz, CHLOROFORM-D): δ ppm 0.23-0.33 (m, 1 H), 1.14-1.30 (m, 2 H), 1.28-1.46 (m, 3 H), 1.45-1.61 (m, 1 H), 1.63-1.86 (m, 3 H), 1.85-2.09 (m, 5 H), 2.50-2.66 (m, 1 H), 2.77-2.90 (m, 4 H), 2.88-3.17 (m, 4 H), 3.44-3.54 (m, 2 H), 3.52-3.75 (m, 5 H), 3.84-3.94 (m, 3 H), 3.95-4.19 (m, 4 H), 4.31-4.52 (m, 1 H), 4.55-4.70 (m, 1 H), 4.73-4.87 (m, 1 H), 5.00-5.23 (m, 1 H), 6.89-7.05 (m, 2 H), 7.05-7.15 (m, 1 H), 7.25-7.32 (m, 1 H), 7.45-7.64 (m, 1 H), 7.78-7.91 (m, 1 H), 7.95-8.13 (m, 1 H).

EXAMPLE 28

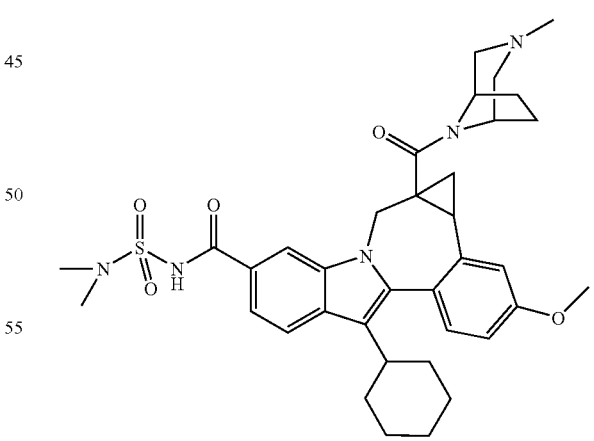

(+/−)-8-Cyclohexyl-N-(isopropylsulfonyl)-1,1a,2,12b-tetrahydro-11-methoxy-1a-(3-methyl-3,8-diazabicyclo[3.2.1]octane-8-carbonyl)cycloprop[d]indolo[2,1-a][2]benzazepine-5-carboxamide. The product was purified by prep HPLC and isolated in mono TFA salt form as a beige solid. LC/MS: Retention time: 1.818 min; m/e 659 (MH$^+$). The title compound was observed to exist as inter-converting rotamers by 1H NMR (400 MHz, CHLOROFORM-D): δ ppm 1.11-

1.29 (m, 2 H), 1.28-1.66 (m, 8 H), 1.67-1.87 (m, 3 H), 1.86-2.11 (m, 5 H), 2.12-2.42 (m, 2 H), 2.43-2.72 (m, 2 H), 2.72-3.04 (m, 4 H), 3.05-3.30 (m, J=7.55, 4.28 Hz, 2 H), 3.31-3.57 (m, 2 H), 3.57-3.78 (m, J=18.63 Hz, 2 H), 3.85-3.93 (m, 3 H), 3.96-4.15 (m, 2 H), 4.37-4.76 (m, J=71.51 Hz, 1 H), 5.04-5.25 (m, 1 H), 6.86-7.02 (m, 1 H), 7.07-7.16 (m, J=2.52 Hz, 1 H), 7.26-7.36 (m, J=8.31, 8.31 Hz, 1 H), 7.44-7.69 (m, 1 H), 7.90 (d, J=8.56 Hz, 1 H), 8.00-8.29 (m, J=48.09 Hz, 1 H), 9.33 (s, 1 H).

EXAMPLE 29

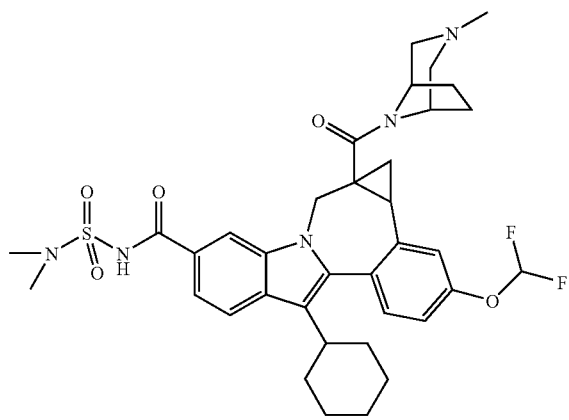

(+/−)-8-Cyclohexyl-N-(N,N-dimethylsulfamoyl)-1,1a,2,12b-tetrahydro-11-difluoromethoxy-1a-(3-methyl-3,8-diazabicyclo[3.2.1]octane-8-carbonyl)-cycloprop[d]indolo[2,1-a][2]benzazepine-5-carboxamide. The product was prepared by difluoromethylation (ClCHF$_2$, 1N NaOH, acetone-isopropanol, rt) of corresponding phenolic derivative and was purified by prep HPLC and isolated in mono TFA salt form as a beige solid. LC/MS: Retention time: 1.798 min; m/e 696 (MH$^+$). The title compound was observed to exist as inter-converting rotamers by 1H NMR (500 MHz, CHLOROFORM-D): δ ppm 0.25-0.81 (m, 3 H), 0.81-1.33 (m, 6 H), 1.29-1.64 (m, 4 H), 1.78 (s, 2 H), 1.85-2.17 (m, J=4.58 Hz, 4 H), 2.36-2.59 (m, 2 H), 2.79 (t, J=11.90 Hz, 2 H), 2.84-2.93 (m, 1 H), 2.97-3.10 (m, 5 H), 3.08-3.23 (m, 1 H), 3.45 (s, 1 H), 4.40 (s, 1 H), 5.07 (s, 1 H), 6.44-6.66 (m, 1 H), 6.73-6.86 (m, J=14.34 Hz, 1 H), 7.17 (d, J=1.83 Hz, 1 H), 7.28 (dd, J=8.55, 2.44 Hz, 1 H), 7.42-7.60 (m, 2 H), 7.92 (d, J=8.55 Hz, 1 H), 8.09 (s, 1 H), 8.91 (s, 1 H).

EXAMPLE 30

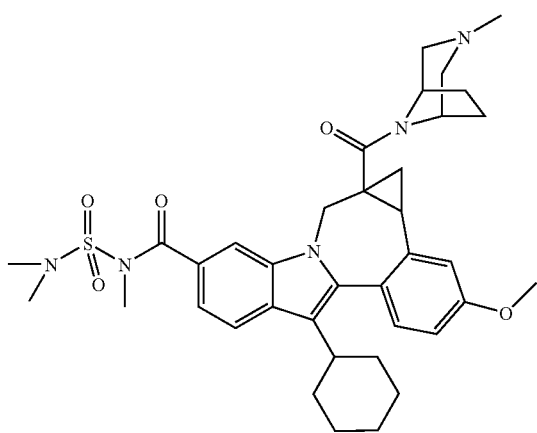

(+/−)-8-Cyclohexyl-N-(N,N-dimethylsulfamoyl)-1,1a,2,12b-tetrahydro-11-methoxy-1a-methyl-3,8-diazabicyclo[3.2.1]octane-8-carbonyl)cycloprop[d]indolo[2,1-a][2]benzazepine-N-methyl-5-carboxamide. The product was prepared by N-methylation of (+/−)-8-cyclohexyl-N-(N,N-dimethylsulfamoyl)-1,1a,2,12b-tetrahydro-11-methoxy-1a-(3-methyl-3,8-diazabicyclo[3.2.1]octane-8-carbonyl)cycloprop[d]indolo[2,1-a][2]benzazepine-5-carboxamide under Mitsonobu conditions (Ph$_3$P, DEAD, MeOH-THF, 0-23° C.), and was purified by prep HPLC and isolated in mono TFA salt form as a beige solid. LC/MS: Retention time: 1.828 min; m/e 674 (MH$^-$). The title compound was observed to exist as inter-converting rotamers by 1H NMR (400 MHz, CHLOROFORM-D): δ ppm 1.12-1.62 (m, 6 H), 1.65-2.32 (m, 8 H), 2.46 (d, J=5.29 Hz, 2 H), 2.69-2.91 (m, 3 H), 2.90-2.99 (m, 7 H), 2.96-3.19 (m, 2 H), 3.25-3.34 (m, 3 H), 3.33-3.43 (m, 1 H), 3.49 (s, 1 H), 3.63 (d, J=15.36 Hz, 1 H), 3.67-3.84 (m, J=1.51 Hz, 1 H), 3.89 (s, 3 H), 3.93-4.20 (m, 1 H), 4.44-4.67 (m, 1 H), 5.09-5.27 (m, 1 H), 6.92-7.02 (m, J=8.69, 2.64 Hz, 1 H), 7.06-7.14 (m, J=2.52 Hz, 1 H), 7.26-7.33 (m, 2 H), 7.64 (s, 1 H), 7.89 (d, J=8.31 Hz, 1 H).

EXAMPLE 31

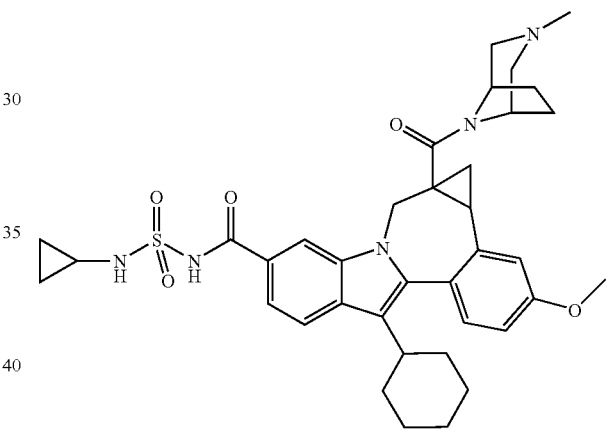

(+/−)-8-Cyclohexyl-N-(N-cyclopropylsulfamoyl)-1,1a,2,12b-tetrahydro-11-methoxy-1a-(3-methyl-3,8-diazabicyclo[3.2.1]octane-8-carbonyl)cycloprop[d]indolo[2,1-a][2]benzazepine-N-methyl-5-carboxamide. The product was purified by prep HPLC and isolated in mono TFA salt form as a beige solid. LC/MS: Retention time: 2.751 min; m/e 672 (MH$^+$). The title compound was observed to exist as inter-converting rotamers by 1H NMR (400 MHz, CHLOROFORM-D): δ ppm 0.55-0.96 (m, 3 H), 1.05-1.59 (m, 6 H), 1.60-2.19 (m, 8 H), 2.22-2.45 (m, 2 H), 2.44-2.81 (m, 6 H), 2.81-3.09 (m, 4 H), 3.36-3.52 (m, J=25.68 Hz, 1 H), 3.59-3.80 (m, 2 H), 3.82-3.94 (m, 3 H), 3.97-4.19 (m, 1 H), 5.14-5.29 (m, 1 H), 5.99 (s, 1 H), 6.90-7.02 (m, J=8.44, 2.90 Hz, 1 H), 7.06-7.14 (m, J=2.52 Hz, 1 H), 7.26-7.35 (m, 1 H), 7.53-7.71 (m, 1 H), 7.93 (d, J=8.56 Hz, 1 H), 8.23 (s, 1 H), 9.95 (s, 1 H).

Examples 32-36 were analyzed by the following LC/MS method: Start % B: 0; Final % B: 100; Gradient time: 3 min; Stop time: 4 min; Flow rate: 4 ml/min; Wavelenth: 220; Solvent A: 10% MeOH/90% H$_2$O/0.1% Trifluoroacetic Acid; Solvent B: 10% H$_2$O/90% MeOH/0.1% Trifluoroacetic Acid; Column: XBridge 4.6×50 mm S5.

EXAMPLE 32

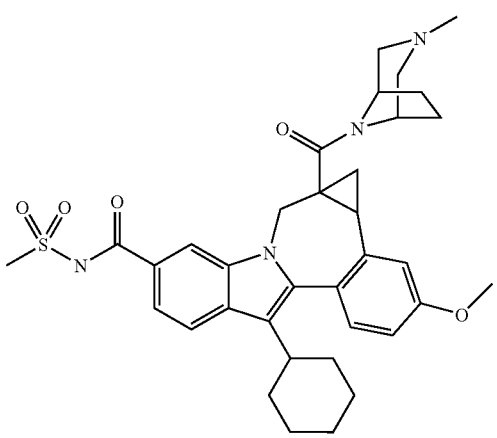

(+/−)-8-cyclohexyl-N-(methylsulfonyl)-1,1a,2,12b-tetrahydro-11-methoxy-1a-(3-methyl-3,8-diazabicyclo[3.2.1]octane-8-carbonyl)cycloprop[d]indolo[2,1-a][2]benzazepine-5-carboxamide. A mixture of indole carboxylic acid-cyclopropylester (1.3 g, 2.83 mmol) and CDI (0.64 g, 3.97 mmol) in THF (20 mL) was heated at 50° C. for 0.5 h, cooled down and added methylsulfonamide (0.4 g, 4.2 mmol) and DBU (0.264 mL, 1.77 mmol). The mixture was stirred for 20 h and diluted with EtOAc, washed with cold 1N HCl (2×), brine, dried (MgSO4), removed the solvent and purified by flash (Biotage 40 M) to afford the compound 1-2 (1.28 g, 85%) as a pale yellow solid. LC-MS retention time: 3.51; MS m/z 537 (M+H). The sulfonamide was observed to exist as inter-converting rotamers. The major isomer: $^1$H NMR (400 MHz, CHLOROFORM-D) δ ppm 1.11-2.17 (m, 12 H), 2.84-2.98 (m, 2 H), 3.43 (d, J=14.86 Hz, 1 H), 3.49 (s, 3 H), 3.55 (s, 3 H), 3.89 (s, 3 H), 5.40 (d, J=15.11 Hz, 1 H), 6.91-6.96 (m, 1 H), 7.13 (d, J=2.52 Hz, 1 H), 7.22-7.27 (m, 1 H), 7.39 (dd, J=8.31, 1.51 Hz, 1 H), 7.85 (d, J=8.81 Hz, 1 H), 8.23 (d, J=1.26 Hz, 1 H), 8.75 (s, 1 H).

To a solution of the sulfonamide-ester (1.28 g, 2.4 mmol) in THF (5 mL) and MeOH (5 mL) was added NaOH (1N, 12 mL, 12 mmol). After being stirred at room temperature for 3 h, the mixture was diluted with EtOAc, washed with cold 1N HCl, brine, dried (MgSO4), and removed the solvent in vacuo to afford the acid as a beige solid (1.20 g, 96%). LC-MS retention time: 3.46; MS m/z 523 (M+H). Compound 1-2 was observed to exist as inter-converting rotamers (~1/1) $^1$H NMR (400 MHz, CHLOROFORM-D).

To a mixture of the acid (0.060 g, 0.11 mmol) and 3-methyl-3,8-diazabicyclo[3.2.1]octane bishydrochloric acid salt (0.034 g, 0.17 mmol) in DMC (1.5 mL) was added Et$_3$N (0.096 mL, 0.69 mmol) and HBTU (0.065 g, 0.17 mmol). The mixture was stirred at room temperature for 0.5 h, diluted with MeOH, removed the solvent. The residue was dissolved in methanol, filtered, and purified by prep-HPLC to afford A TFA salt of the product (0.0378 g, 82%) in TFA salt. LC-MS retention time: 2.96; MS m/z 631 (M+H). The product was observed to exist as inter-converting rotamers $^1$H NMR (400 MHz, CHLOROFORM-D) δ ppm 1.04-1.61 (m, 8 H), 1.68-2.38 (m, 10 H), 2.48-3.03 (m, 6 H), 3.09-3.20 (m, 1 H) 3.30,-3.78 (m, 2 H), 3.41 (s, 3 H), 3.88 (s, 3 H), 4.05 (d, J=14.10 Hz, 1 H), 5.06-5.28 (m, 1 H), 6.97 (dd, J=8.81, 2.27 Hz, 1 H), 7.11 (d, J=2.27 Hz, 1 H), 7.24-7.34 (m, 1 H), 7.54-7.73 (m, 1 H), 7.82-7.94 (m, J=7.18, 5.41 Hz, 1 H), 8.17 (s, 1 H).

EXAMPLE 33

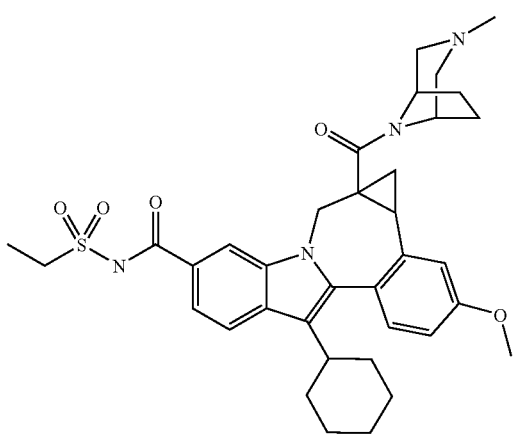

(+/−)-8-cyclohexyl-N-(ethylsulfonyl)-1,1a,2,12b-tetrahydro-11-methoxy-1a-(3-methyl-3,8-diazabicyclo[3.2.1]octane-8-carbonyl)cycloprop[d]indolo[2,1-a][2]benzazepine-5-carboxamide. In a manner similar to that above, the product was prepared: sulfonamide (0.47 g, 44%); LC-MS retention time: 3.54; MS m/z 551 (M+H); acid (0.43 g, 94%); LC-MS retention time: 3.49; MS m/z 537 (M+H). A TFA salt of the product was prepared (0.0378 g, 71%). LC-MS retention time: 3.028 MS m/z 645 (M+H). The product was observed to exist as inter-converting rotamers, the major isomer: $^1$H NMR H NMR (500 MHz, ppm 1.12-2.37 (m, 19 H), 2.51-2.66 (m, 1 H), 2.69-3.03 (m, 4 H), 3.08-3.22 (m, 1 H), 3.21-3.83 (m, 8 H), 3.90 (s, 3 H), 5.11-5.28 (m, 1 H), 6.87-6.95 (m, 1 H), 6.97-7.00 (m, 1 H), 7.12 (d, J=2.14 Hz, 1 H), 7.30 (d, J=8.85 Hz, 1 H), 7.88-7.96 (m, 1 H), 8.08 (s, 1 H).

EXAMPLE 34

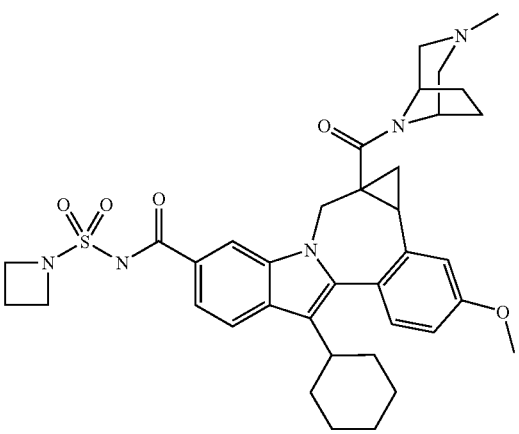

(+/−)-8-Cyclohexyl-N-(azetidin-1-ylsulfonyl)-1,1a,2,12b-tetrahydro-11-methoxy-1a-(3-methyl-3,8-diazabicyclo[3.2.1]octane-8-carbonyl)-cycloprop[d]indolo[2,1-a][2]benzazepine-5-carboxamide. In a manner similar to that above, the product was prepared: sulfonamide (0.96 g, 59%); LC-MS retention time: 3.58; MS m/z 578 (M+H). The compound was observed to exist as inter-converting rotamers (3/4). The major isomer: ¹H NMR (400 MHz, CHLOROFORM-D) δ ppm 1.16-1.59 (m, 4 H), 1.72 (dd, J=9.44, 4.15 Hz, 3 H), 1.88-2.12 (m, 4 H), 2.24-2.36 (m, 2 H), 2.75-2.97 (m, 2 H), 3.44 (d, J=14.86 Hz, 1 H), 3.56 (s, 3 H), 3.89 (s, 3 H), 4.09 (d, 1 H), 4.24-4.37 (m, 4 H), 5.41 (d, J=14.86 Hz, 1 H), 6.92-6.96 (m, 1 H), 7.13 (d, J=2.01 Hz, 1 H), 7.24-7.30 (m, 1 H), 7.39 (dd, J=8.31, 1.51 Hz, 1 H), 7.84-7.88 (m, 1 H), 8.24 (d, J=1.51 Hz, 1 H); acid (0.93 g, 100%); LC-MS retention time: 3.5 1; MS m/z 564 (M+H). Compound was observed to exist as inter-converting rotamers (~3/4). The major isomer: ¹H NMR (400 MHz, ppm 0.34-0.42 (m, 1 H), 1.15-2.10 (m, 11 H), 2.22-2.38 (m, 2 H), 2.65-2.78 (m, 1 H), 2.84-2.94 (m, J=3.02 Hz, 1 H), 3.84 (s, 3 H), 4.03 (d, J=15.11 Hz, 1 H), 4.21-4.43 (m, 4 H), 5.34 (d, J=14.86 Hz, 1 H), 6.87 (dd, J=8.56, 2.77 Hz, 1 H), 6.98 (d, J=2.52 Hz, 1 H), 7.21 (d, J=8.31 Hz, 1 H), 7.69-7.75 (m, 1 H), 7.86-7.90 (m, 1 H), 8.13 (s, 1 H). A TFA salt of the product was prepared: LC-MS retention time: 3.51; MS m/z 672 (M+H). The title compound was observed to exist as inter-converting rotamers in ¹H NMR (400 MHz, CHLOROFORM-D): ¹H NMR (400 MHz, ppm 1.02-1.63 (m, 8 H), 1.72-2.36 (m, 10 H), 2.47-3.23 (m, 6 H), 3.45 (d, J=29.46 Hz, 2 H), 3.59-3.75 (m, 2 H), 3.89 (s, 3 H), 4.12-4.38 (m, 4 H), 4.38-4.98 (m, 2 H), 5.12-5.30 (m, 1 H), 6.90-7.03 (m, 2 H), 7.12 (d, J=2.52 Hz, 1 H), 7.27-7.35 (m, J=9.06, 9.06 Hz, 1 H), 7.59-7.75 (m, 1 H), 7.84-7.96 (m, 1 H).

EXAMPLE 35

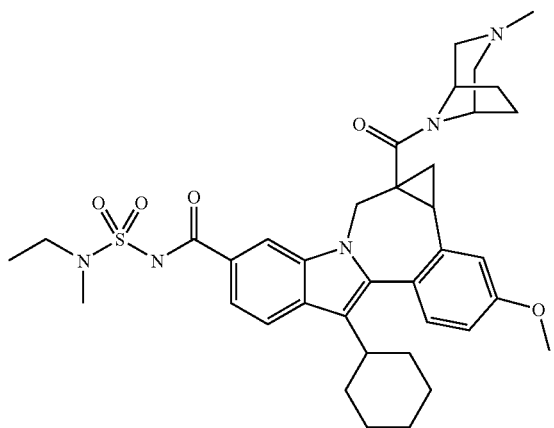

(+/−)-8-Cyclohexyl-N-(N-ethyl-N-methylaminosulfonyl)-1,1a,2,12b-tetrahydro-11-methoxy-1a-(3-methyl-3,8-diazabicyclo[3.2.1]octane-8-carbonyl)-cycloprop[d]indolo[2,1-a][2]benzazepine-5-carboxamide. Prepared from the acid in similar method as described above. Sulfonamide (0.109 g, 67%). LC-MS retention time: 3.60; MS m/z 580 (M+H). Compound was observed to exist as inter-converting rotamers (~5/4). The major isomer: ¹H NMR (400 MHz, ppm 1. 16-2.09 (m, 14 H), 2.73-2.93 (m, 2 H), 3.07 (s, 3 H), 3.31-3.52 (m, 3 H), 3.76 (s, 3.88 (s, 3 H), 4.05-4.10 (m, 1 H), 5.40 (d, J=15.11 Hz, 1 H), 6.88-6.93 (m, 1 H), 7.13 (d, J=2.27 Hz, 1 H), 7.22-7.29 (m, 1 H), 7.33-7.42 (m, 1 H), 7.82-7.86 (m, 1 H), 8.19 (d, J=1.51 Hz, 1 H). Acid (0.108 g, 100%). LC-MS retention time: 3.55; MS m/z 566 (M+H). A TFA salt of the product was prepared (0.0437 g, 54%). LC-MS retention time: 3.10; MS m/z 674 (M+H). 1H NMR (500 MHz, ppm 1.14-1.62 (m, 6 H), 1.22 (t, J=7.17 Hz, 3 H), 1.69-2.21 (m, 10 H), 2.25-3.31 (m, 11 H), 3.02 (s, 3 H), 3.43 (q, J=7.02 Hz, 2 H), 3.55-3.80 (m, 1 H), 3.89 (s, 3 H), 5.08-5.29 (m, 1 H), 6.93-7.00 (m, 1 H), 7.11 (d, J=2.44 Hz, 1 H), 7.28-7.31 (m, 1 H), 7.39-7.56 (m, 1 H), 7.85-7.91 (m, 1 H), 8.04 (s, 1 H).

EXAMPLE 36

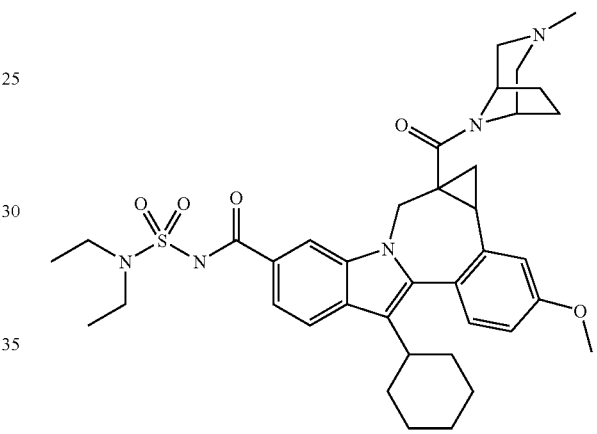

(+/−)-8-Cyclohexyl-N-(N-ethyl-N-methylaminosulfonyl)-1,1a,2,12b-tetrahydro-11-methoxy-1a-(3-methyl-3,8-diazabicyclo[3.2.1]octane-8-carbonyl)-cycloprop[d]indolo[2,1-a][2]benzazepine-5-carboxamide. Prepared from the acid in similar method as described above. Sulfonamide (0.127 g, 67%); LC-MS retention time: 3.64; MS m/z 594 (M+H). Compound was observed to exist as inter-converting rotamers: ¹H NMR (400 MHz, ppm 1.11-2.13 (m, 18 H), 2.64 (dd, J=10.07, 6.80 Hz, 1 H), 2.84-2.96 (m, 1 H), 3.34-3.67 (m, 4 H), 3.75 (s, 3 H), 3.88 (s, 3 H), 4.03-4.10 (m, 1 H), 5.40 (d, J=15.36 Hz, 1 H), 6.90-6.95 (m, 1 H), 7.13 (d, J=2.01 Hz, 1 H), 7.21-7.29 (m, 1 H), 7.33-7.39 (m, 1 H), 7.83 (d, J=8.06 Hz, 1 H), 8.20 (d, J=1.26 Hz, 1 H). Acid: (0.126 g, 100%). LC-MS retention time: 3.57; MS m/z 580 (M+H). A TFA salt of the product was prepared (0.431 g, 52%). LC-MS retention time: 3.18; MS m/z 688 (M+H). ¹H NMR (400 MHz, CHLOROFORM-D) d ppm 1.13-1.55 (m, 6 H), 1.21 (t, J=7.18 Hz, 6H), 2.31-3.55 (m, 11 H), 2.41-3.29 (m, 10 H), 3.49 (q, J=7.05 Hz, 4 H), 3.59-3.67 (m, 1 H), 3.89 (s, 3 H), 5.02-5.29 (m, 1 H), 6.97 (dd, J=8.81, 2.27 Hz, 1 H), 7.10 (d, J=2.52 Hz, 1 H), 7.28 (d, J=8.56 Hz, 1 H), 7.36-7.49 (m, 1 H), 7.83-7.91 (m, 1 H), 7.95-8.06 (m, 1 H).

EXAMPLE 37

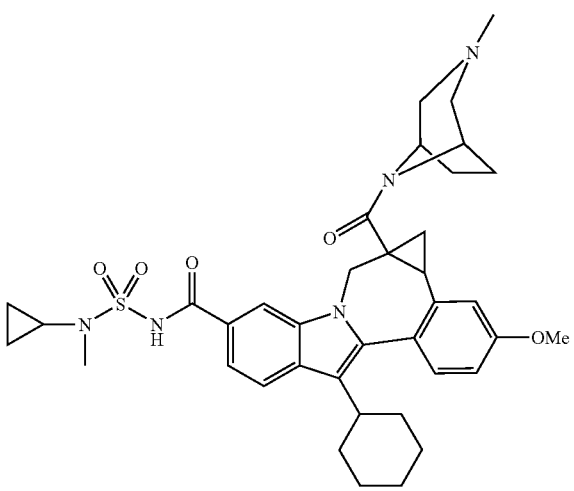

Neat 2-(1H-Benzotriazol-1-yl)-1,1,3,3-tetramethyluronium tetrafluoroborate (0.0535 g, 0.167 mmol) was added to stirred mixture of Compound 1-4 (0.0774 g, 0.128 mmol), 3-methyl-3,8-diazabicyclo[3.2.1]octane, 2HCl (0.026.4 g, 0.128 mmol) and TEA (0.071 ml, 0.512 mmol) in DCM (2 ml) under nitrogen. The mixture was stirred at rt for 1 h and quenched with MeOH (0.5 ml) and then evaporated to dryness and purified by reverse-phase HPLC to afford isolated in mono TFA salt form of the product (0.0613 g, 60%)) as a beige solid. LC/MS: m/e 686 (MH+). LC/MS method: Start % B: 0, Final % B: 100; Gradient time: 3 min; Stop time: 4 min; Flow rate: 4 ml/min; Wavelenth: 220; Solvent A: 10% MeOH/90% H$_2$O/0.1% Trifluoroacetic Acid; Solvent B: 10% H$_2$O/90% MeOH/0.1% Trifluoroacetic Acid; Column: XBridge 4.6×50 mm S5.

EXAMPLE 38

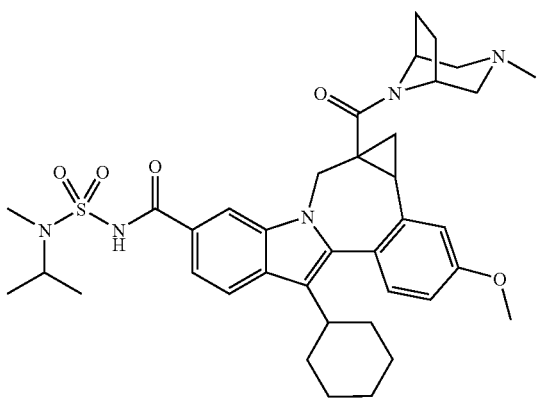

The TFA salt of the amide (0.0465 g 56%) was made from the acid (0.060 g, 0.104 mmol) and amine using HBTU and TEA in methylene chloride. LC-MS retention time: 3.146 min; MS m/z (M+H) 688. LC/MS method: Start % B: 0, Final % B: 100; Gradient time: 3 min; Stop time: 4 min; Flow rate: 4 ml/min; Wavelenth: 220; Solvent A: 10% MeOH/90% H$_2$O/0.1% Trifluoroacetic Acid; Solvent B: 10% H$_2$O/90% MeOH/0.1% Trifluoroacetic Acid; Column: XBridge 4.6×50 mm S5. 1H NMR existed rotomers, The major form: 1H NMR (400 MHz, CHLOROFORM-d) ppm 1.14-1.18 (m, 6H) 1.19-2.12 (m, 16 H) 2.19-3.77 (m, 9H) 2.95 (s, 3 H) 3.89 (s, 3 H) 3.95-5.02 (m, 4 H) 5.03-5.24 (m, 1 H) 6.97 (dd, J=8.81, 2.77 Hz, 1 H) 7.11 (d, J=2.52 Hz, 1 H) 7.28 (d, J=8.56 Hz, 1 H) 7.40-7.64 (m, 1 H) 7.88 (d, J=8.31 Hz, 1 H) 8.07 (br. s., 1 H).

We claim:
1. A compound of formula I

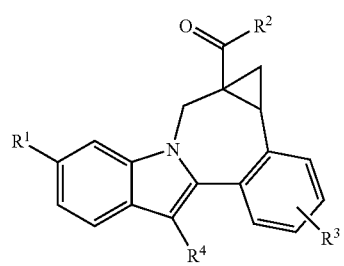

where:
$R^1$ is CO$_2$R$^5$ or CONR$^6$R$^7$;
$R^2$ is

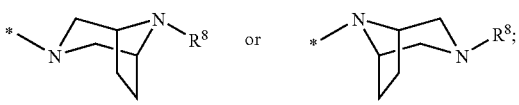

$R^3$ is hydrogen, halo, alkyl, alkenyl, hydroxy, benzyloxy, alkoxy, or haloalkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, (R$^9$)$_2$NSO$_2$, or (R$^{10}$)SO$_2$;
$R^7$ is hydrogen or alkyl;
$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;
$R^9$ is hydrogen, alkyl, or cycloalkyl; and
$R^{10}$ is azetidinyl, pyrrolidinyl, piperidinyl, piperazinyl, morpholinyl, thiomorpholinyl, homopiperidinyl, or homomorpholinyl and is substituted with 0-3 alkyl substituents;
or a pharmaceutically acceptable salt thereof.
2. A compound claim 1 where:
$R^3$ is hydrogen, halo, alkyl, alkenyl, hydroxy, benzyloxy, or alkoxy;
$R^8$ is hydrogen, alkyl, cycloalkyl, (cycloalkyl)alkyl, alkylcarbonyl, alkoxycarbonyl, benzyl, benzyloxycarbonyl, or pyridinyl;
$R^9$ is hydrogen or alkyl; and
$R^{10}$ is azetidinyl, pyrrolidinyl, piperidinyl, piperazinyl, N-(alkyl)piperazinyl, morpholinyl, thiomorpholinyl, homopiperidinyl, or homomorpholinyl.
3. A compound of claim 1 where $R^1$ is CONR$^6$R$^7$; $R^6$ is alkylSO$_2$, cycloalkylSO$_2$, haloalkylSO$_2$, (R$^9$)$_2$NSO$_2$, or (R$^{10}$)SO$_2$; and R$^7$ is hydrogen.

4. A compound of claim 1 where $R^3$ is hydrogen.
5. A compound of claim 1 where $R^3$ is methoxy.
6. A compound of claim 1 where $R^4$ is cyclohexyl.
7. A compound of claim 1 where $R^6$ is alkylSO$_2$, (R$^9$)$_2$NSO$_2$ or (R$^{10}$)SO$_2$.
8. A compound of claim 1 according to the following stereochemistry.

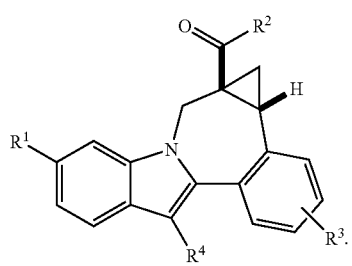

9. A compound of claim 1 according to the following stereochemistry.

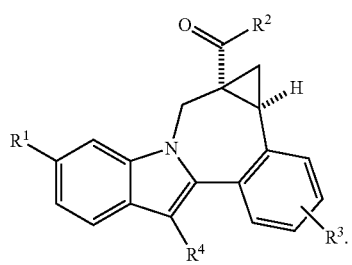

10. A compound of claim 1 selected from the group consisting of

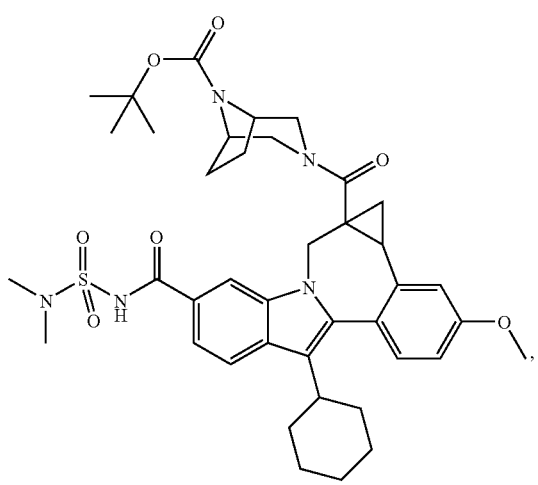

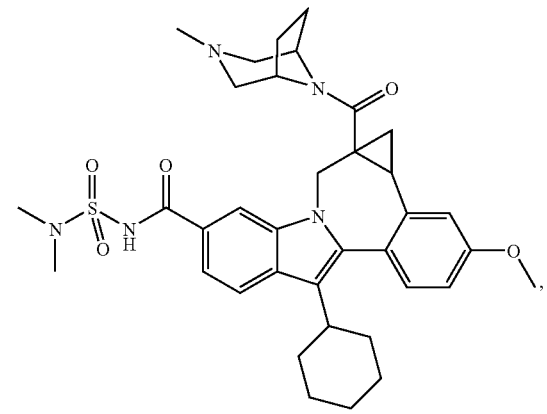

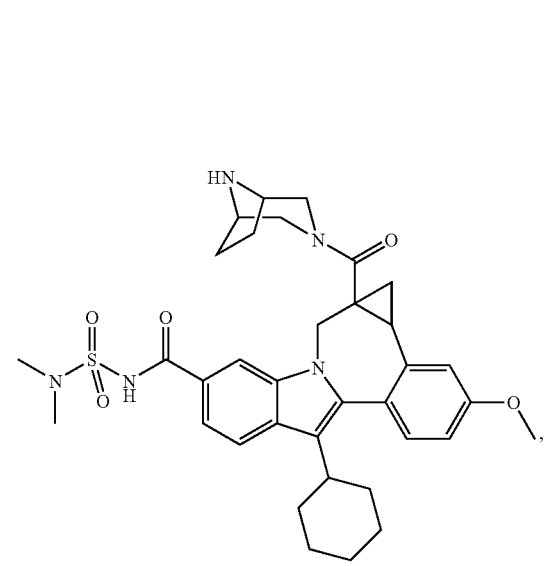

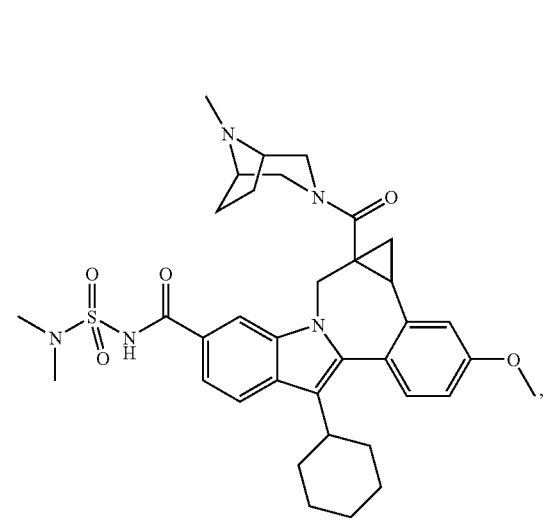

131 -continued
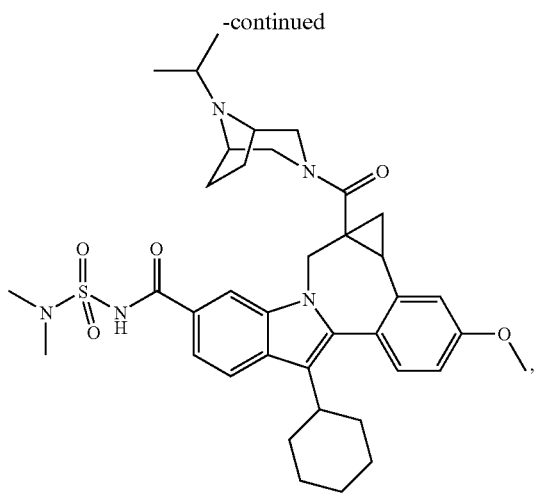
132 -continued
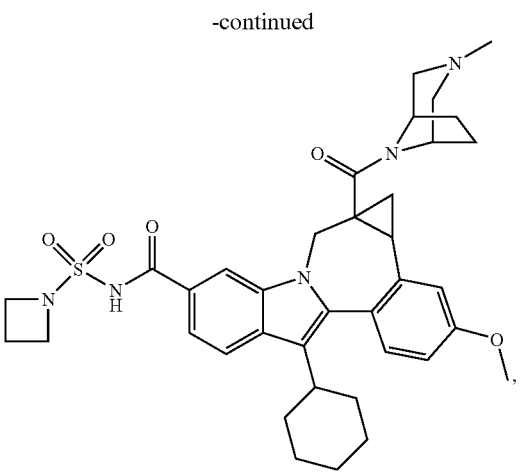
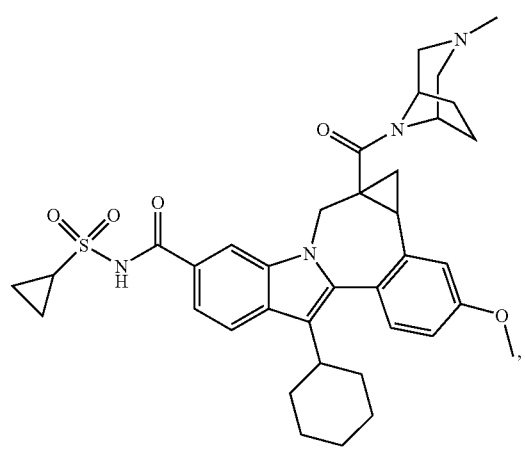
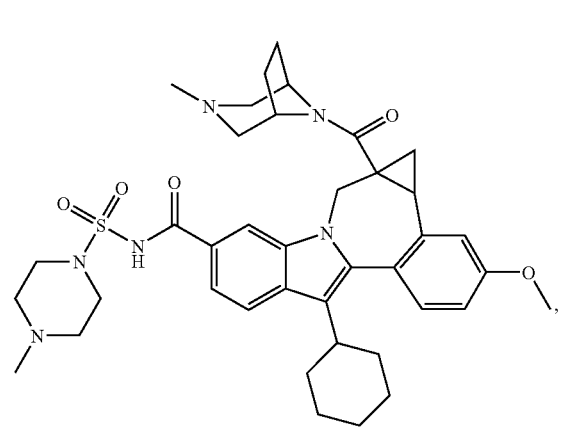
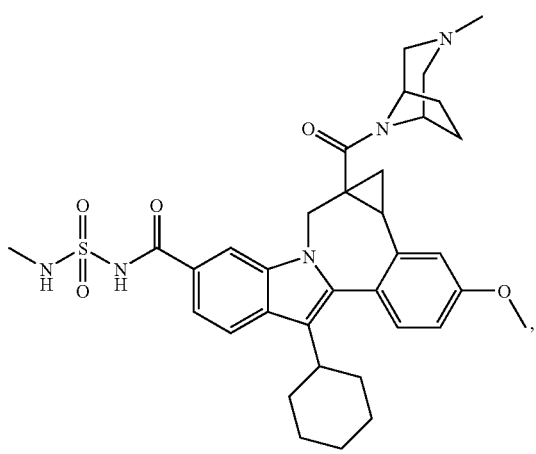

133
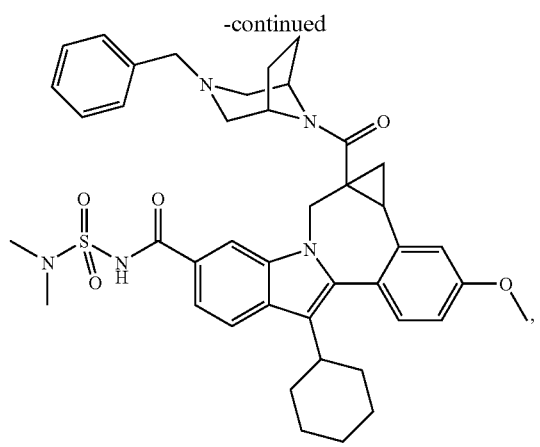
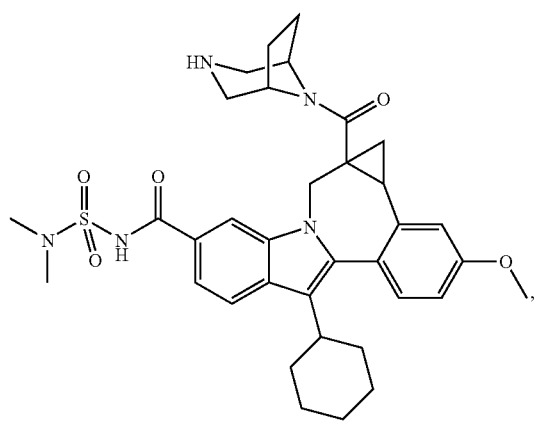
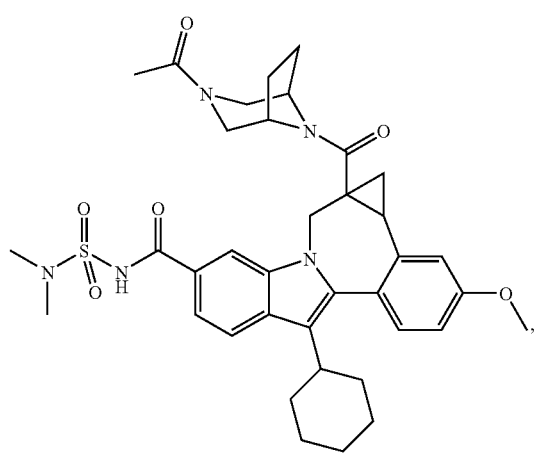
134
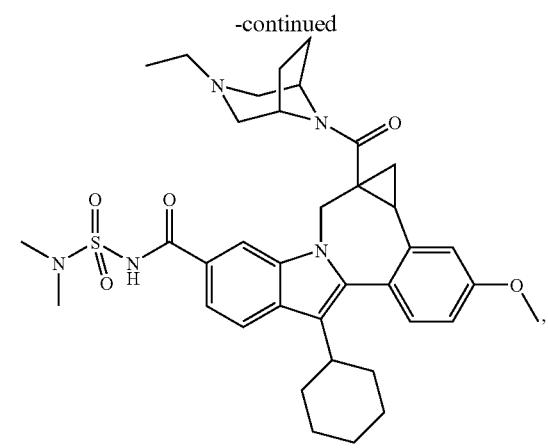
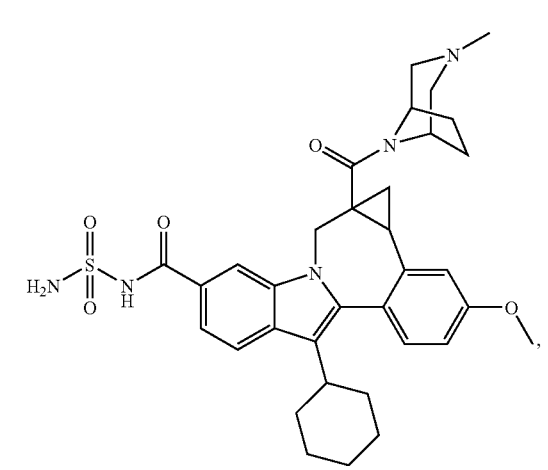

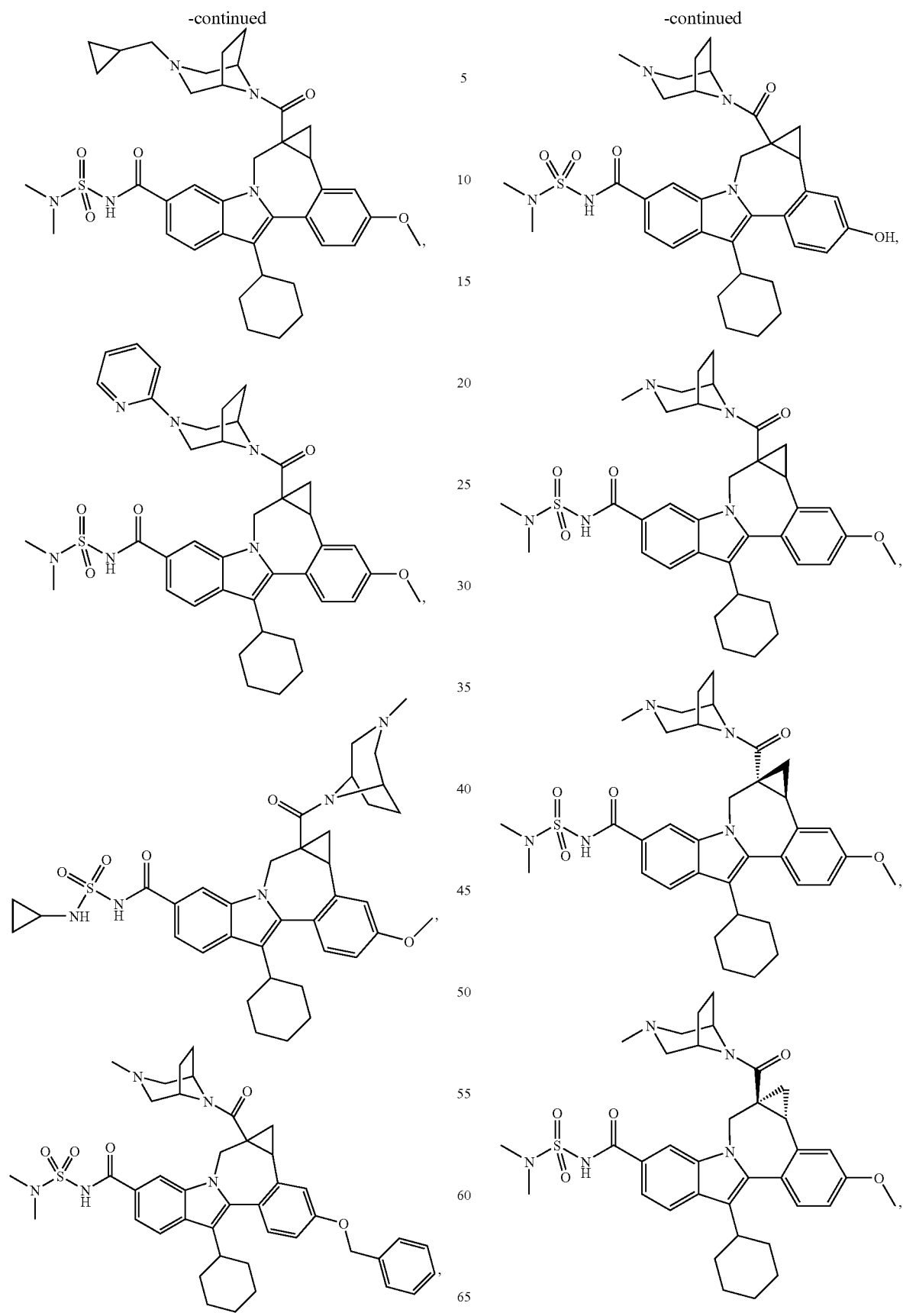

137
-continued
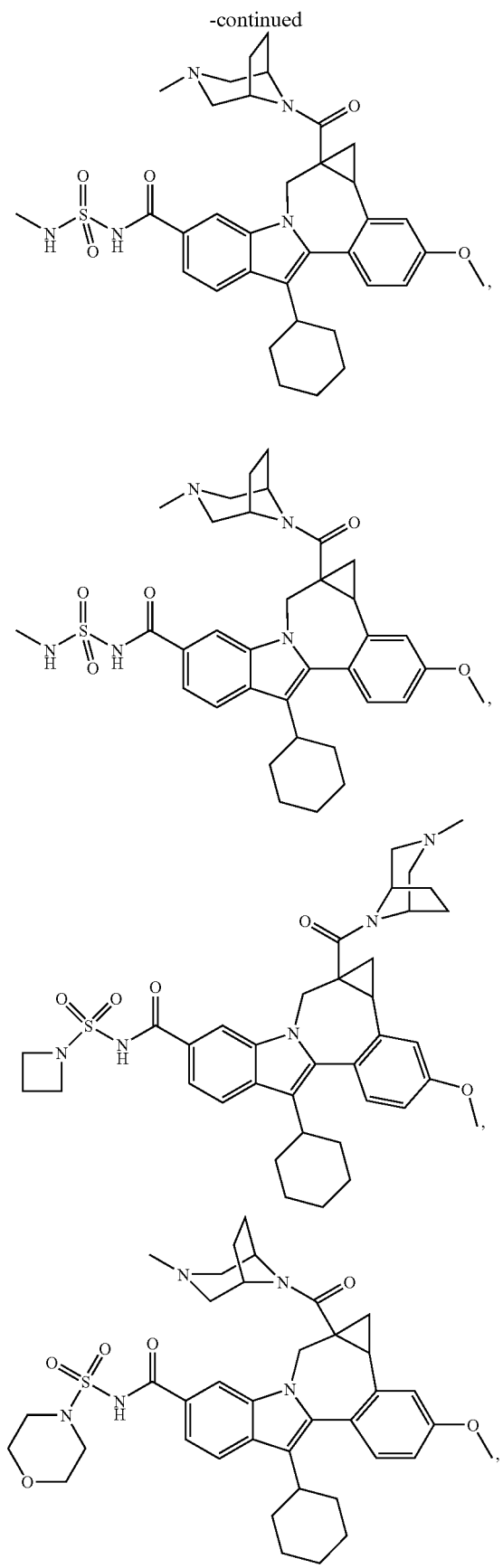
138
-continued
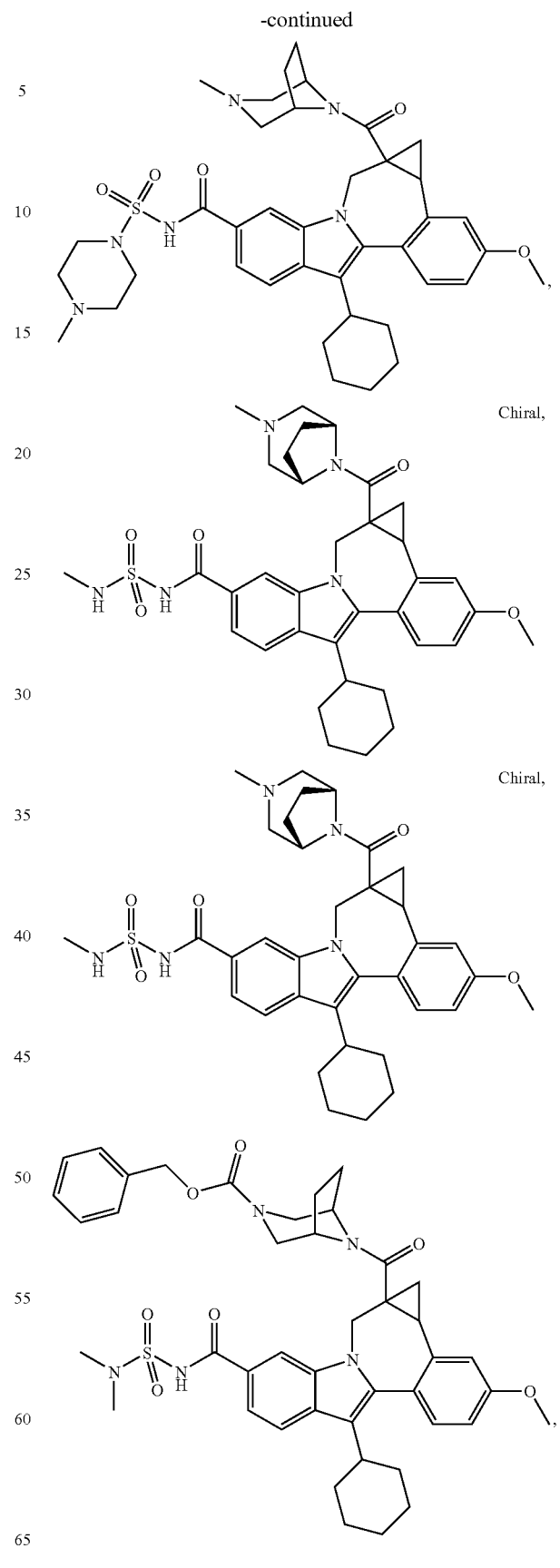

139
-continued
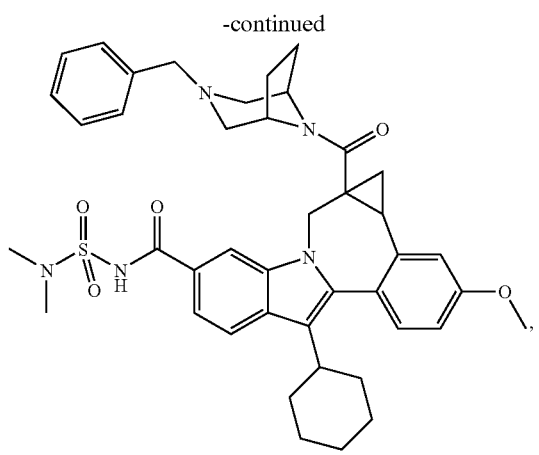
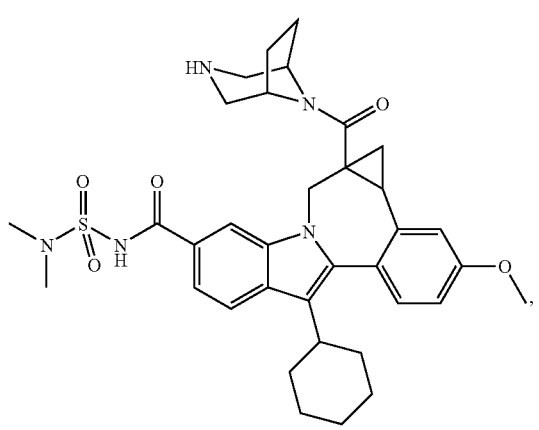
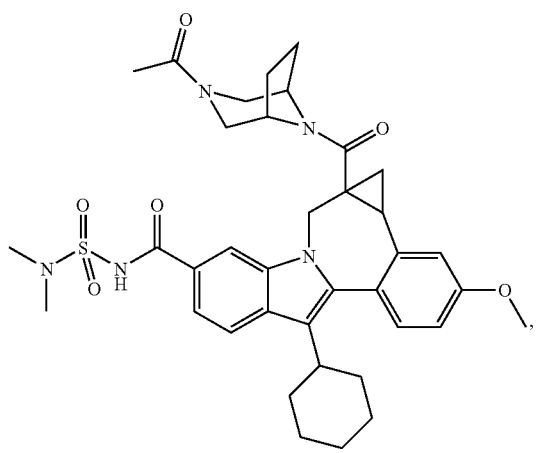
140
-continued
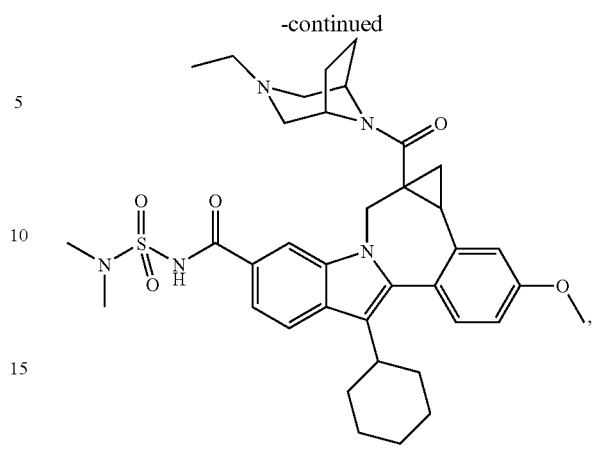
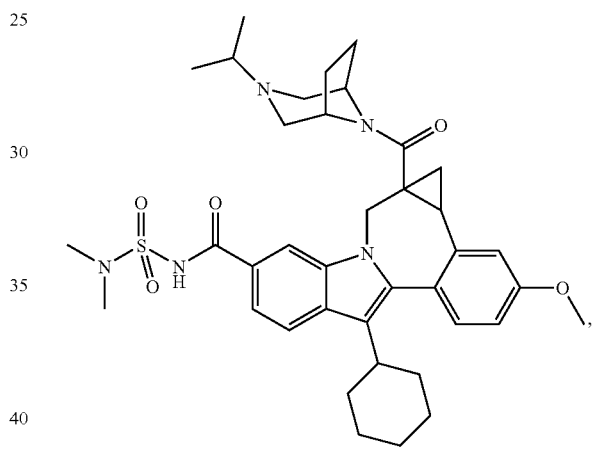
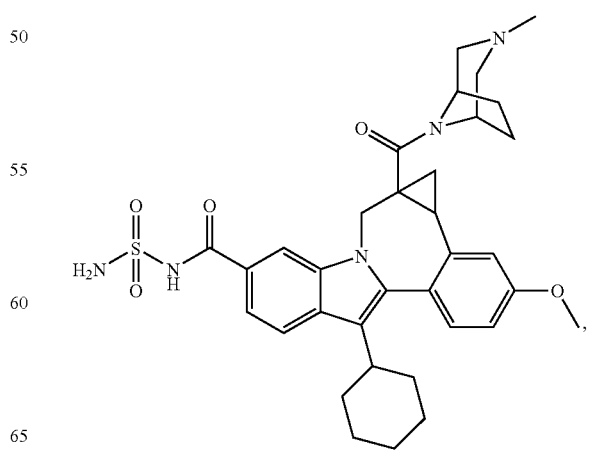

141
-continued
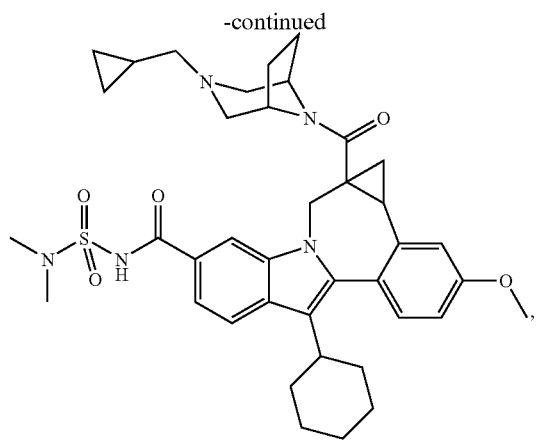
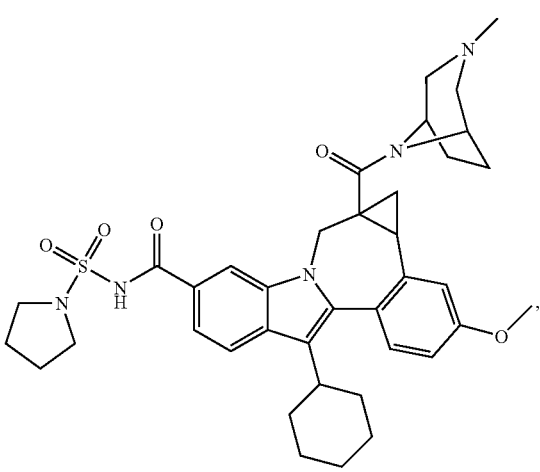
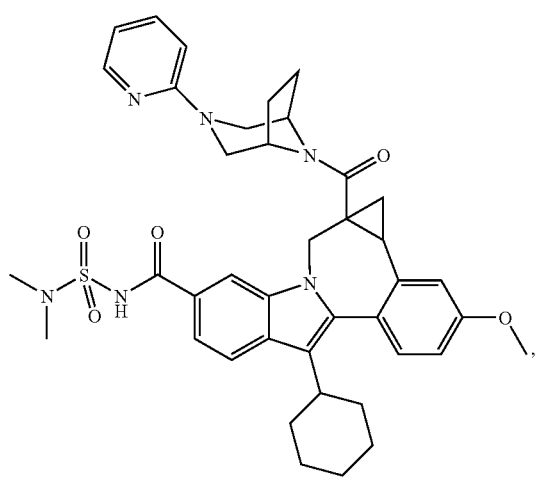
142
-continued
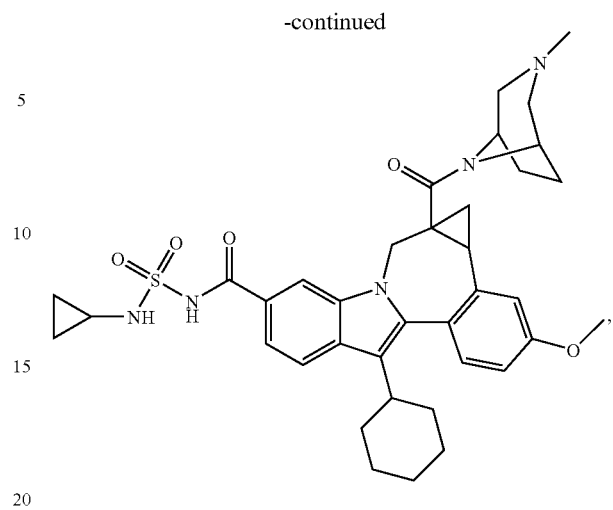
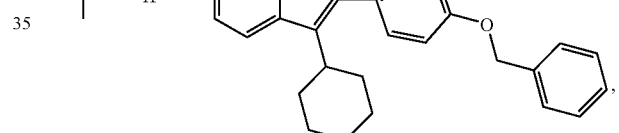
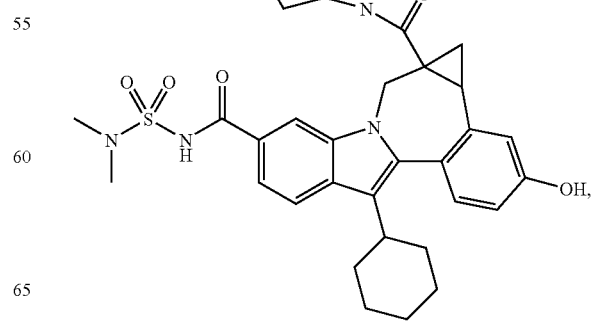

143
-continued
144
-continued
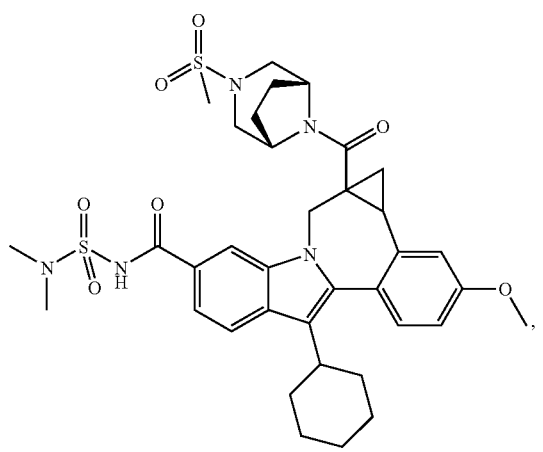
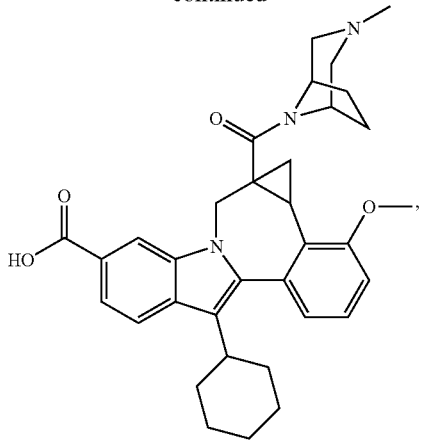

145
-continued
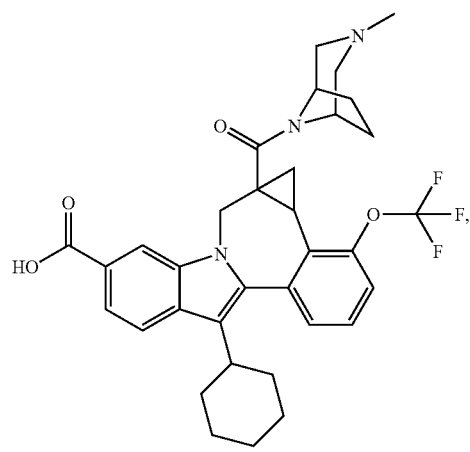
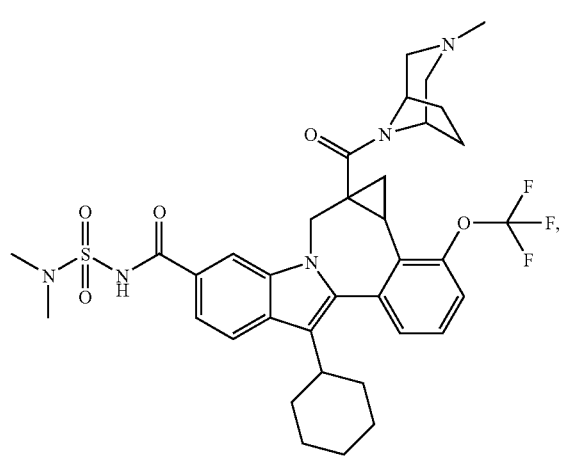
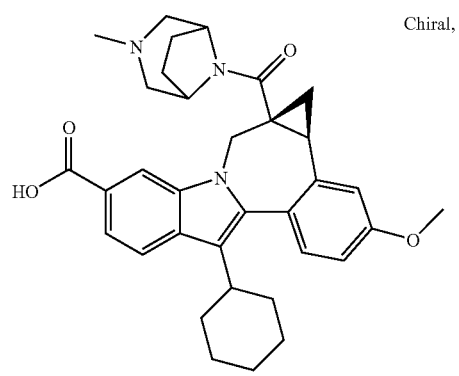
146
-continued Chiral,
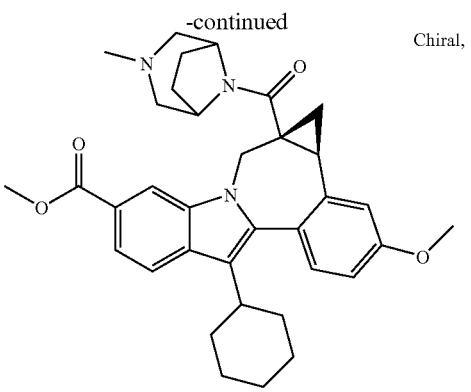
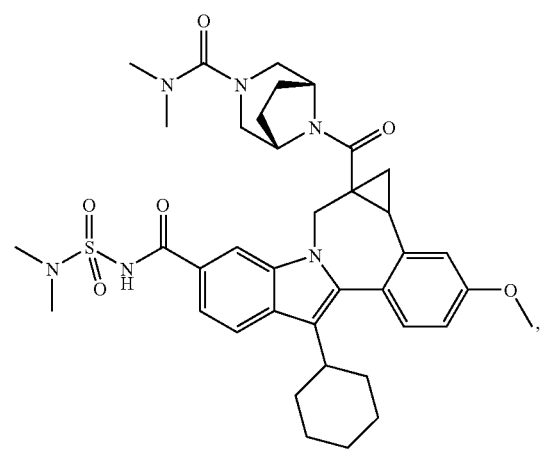
Chiral,
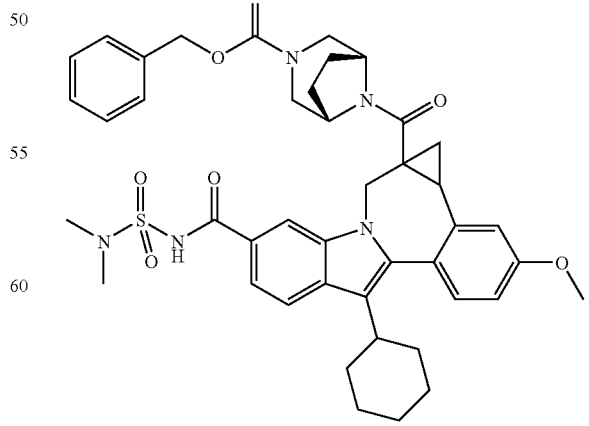
Chiral,

147
-continued
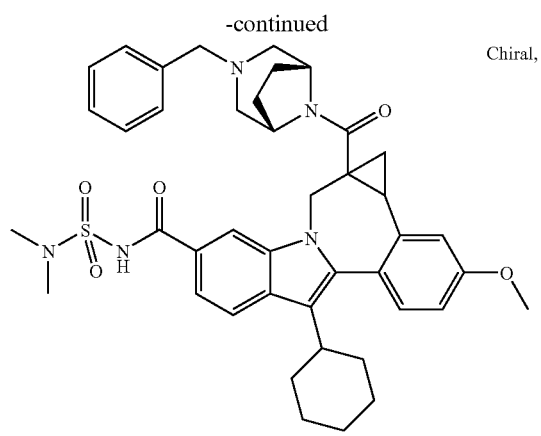
Chiral,
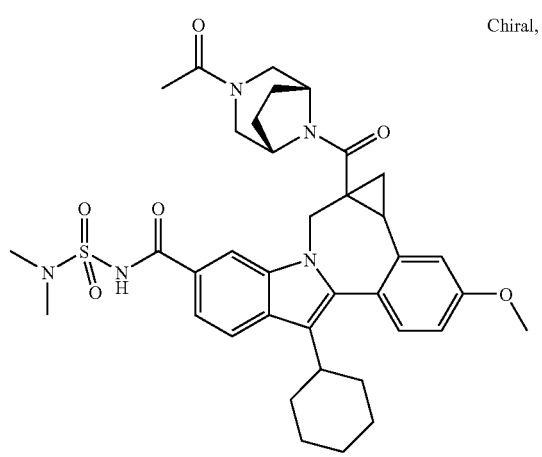
Chiral,
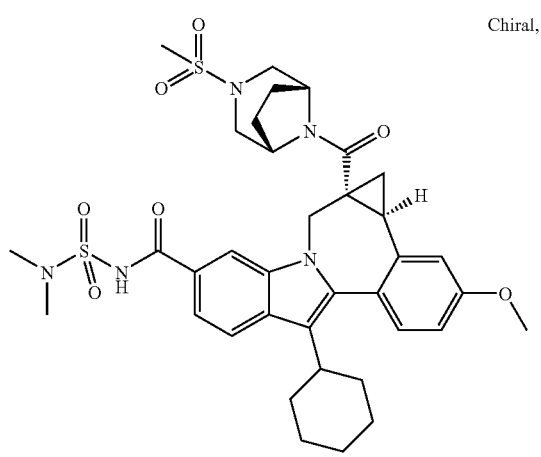
Chiral,
148
-continued
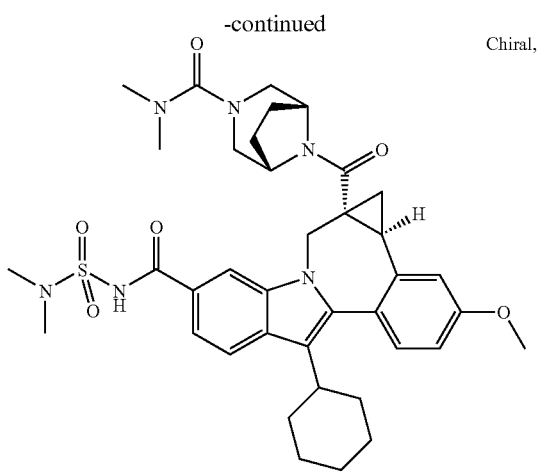
Chiral,
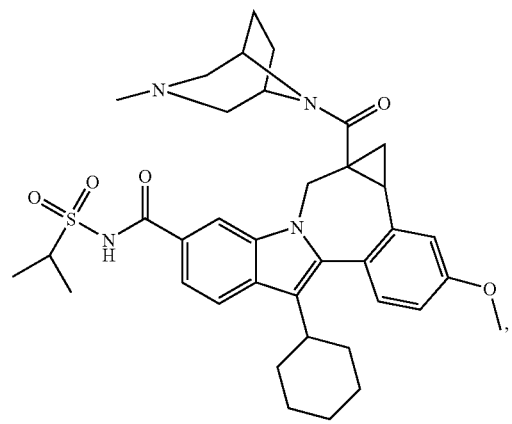
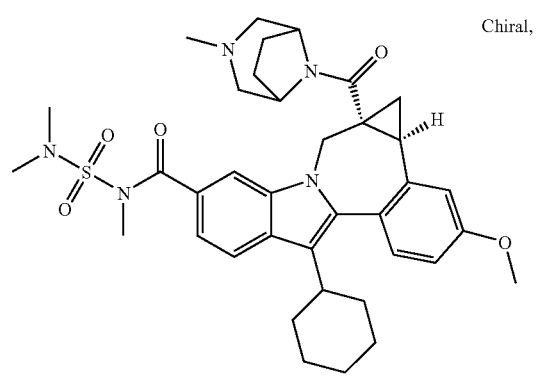
Chiral,

149
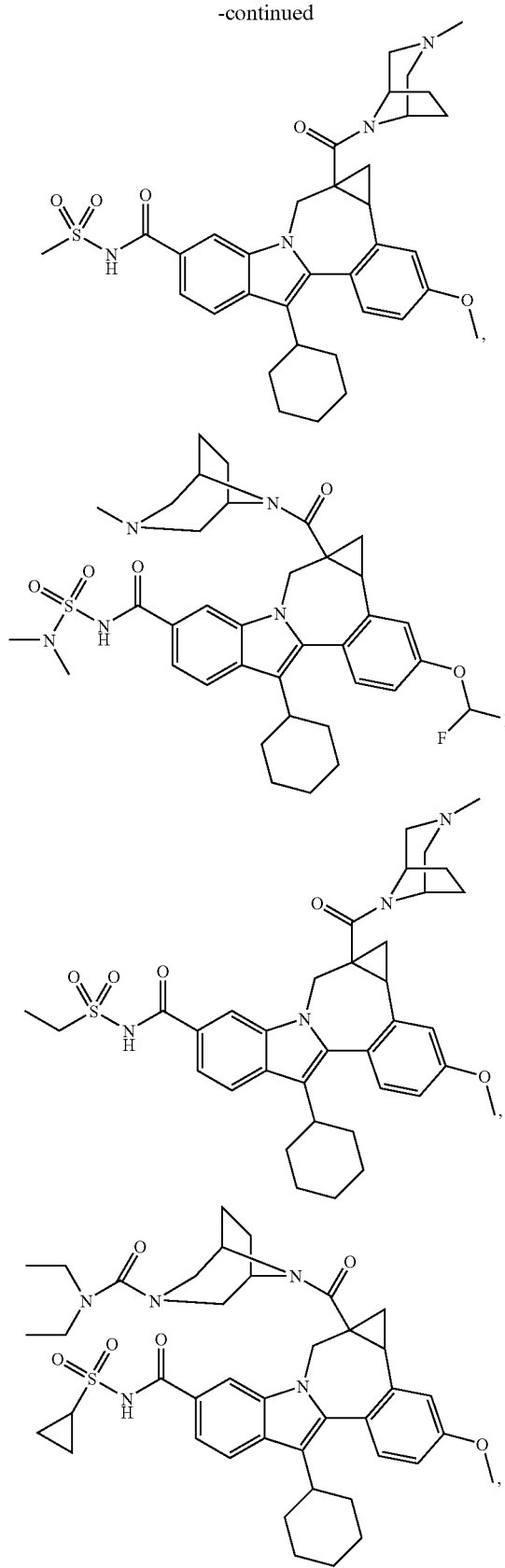
150
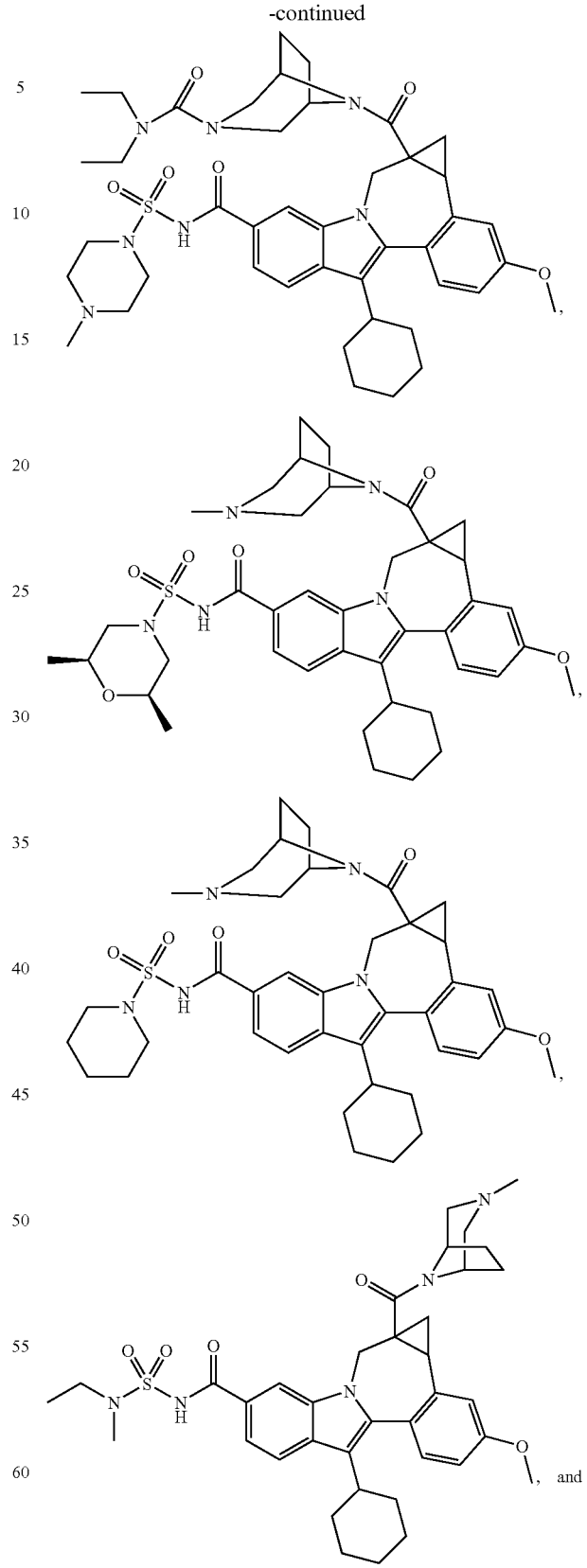

-continued

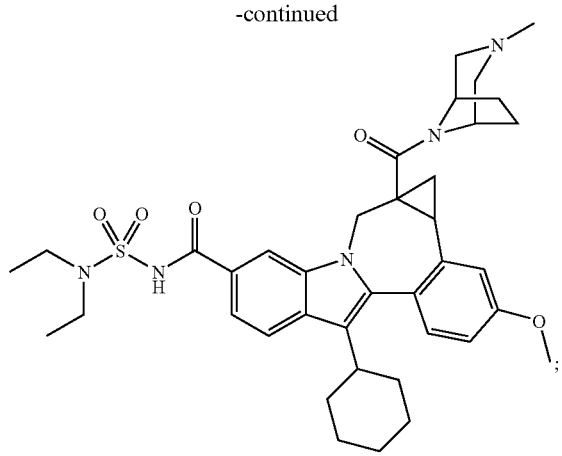

or a pharmaceutically acceptable salt thereof.

11. The compound of claim 1

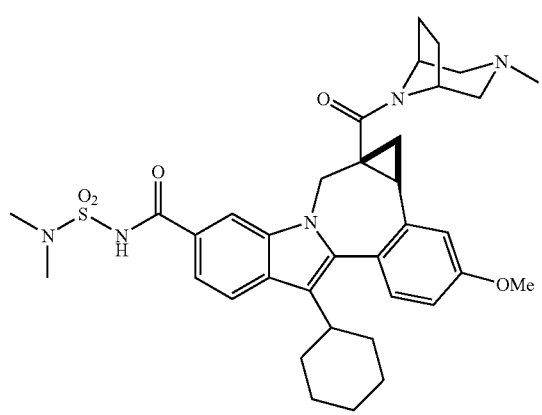

or a pharmaceutically acceptable salt thereof.

12. The compound of claim 11 where the salt is hydrochloride.

13. The compound of claim 1

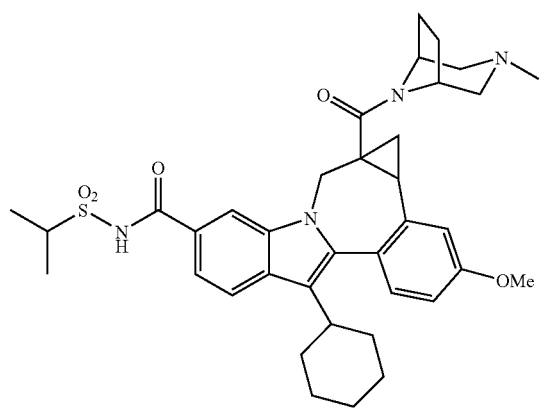

or a pharmaceutically acceptable salt thereof.

14. A composition comprising a compound of claim 1, or a pharmaceutically acceptable salt thereof, and a pharmaceutically acceptable carrier.

15. The composition of claim 14 wherein the compound of claim 1 is

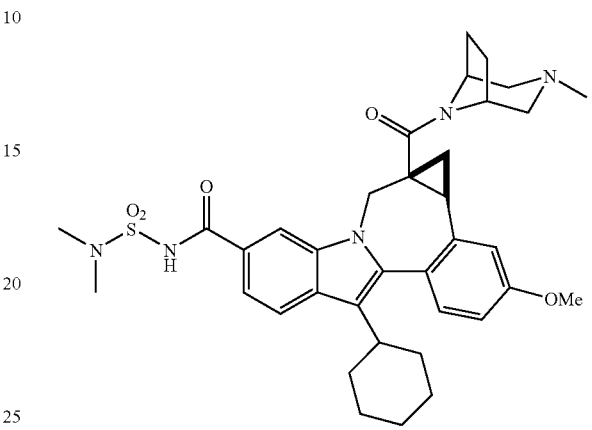

or a pharmaceutically acceptable salt thereof.

16. A method of treating hepatitis C infection comprising administering a therapeutically effective amount of a compound of claim 1 to a patient.

17. The method of claim 15 wherein the compound of claim 1 is

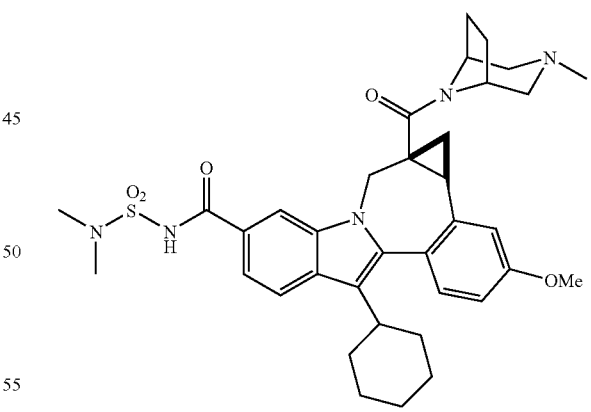

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,456,166 B2 | Page 1 of 1 |
| APPLICATION NO. | : 11/743921 | |
| DATED | : November 25, 2008 | |
| INVENTOR(S) | : John A. Bender et al. | |

It is certified that error appears in the above-identified patent and that said Letters Patent is hereby corrected as shown below:

<u>In the Claims:</u>

Claim 1:

Column 128, line 26, change "$R^1$is $CO_2R^5$or" to -- $R^1$ is $CO_2R^5$ or --.

Claim 2:

Column 128, line 55, after "compound", insert -- of --.

Signed and Sealed this
Fourth Day of March, 2014

Michelle K. Lee
*Deputy Director of the United States Patent and Trademark Office*